US008158856B2

(12) United States Patent
De Block et al.

(10) Patent No.: US 8,158,856 B2
(45) Date of Patent: Apr. 17, 2012

(54) STRESS RESISTANT PLANTS

(75) Inventors: Marc De Block, Merelberke (BE);
Michael Metzlaff, Tervuren (BE);
Veronique Gossele, Ghent (BE)

(73) Assignee: Bayer CropScience NV, Diegem (BE)

( * ) Notice: Subject to any disclaimer, the term of this patent is extended or adjusted under 35 U.S.C. 154(b) by 693 days.

(21) Appl. No.: 12/293,738

(22) PCT Filed: Mar. 16, 2007

(86) PCT No.: PCT/EP2007/002433
§ 371 (c)(1),
(2), (4) Date: Sep. 19, 2008

(87) PCT Pub. No.: WO2007/107326
PCT Pub. Date: Sep. 27, 2007

(65) Prior Publication Data
US 2009/0320154 A1      Dec. 24, 2009

Related U.S. Application Data

(60) Provisional application No. 60/784,179, filed on Mar. 21, 2006.

(30) Foreign Application Priority Data

Mar. 21, 2006   (EP) ..................................... 06075671
Mar. 22, 2006   (EP) ..................................... 06075700

(51) Int. Cl.
*A01H 5/00*      (2006.01)
*A01H 5/10*      (2006.01)
*C12N 15/82*     (2006.01)
(52) U.S. Cl. ........................................ 800/288; 435/419
(58) Field of Classification Search .................... 800/289
See application file for complete search history.

(56) References Cited

U.S. PATENT DOCUMENTS

2005/0267023 A1*   12/2005   Sinclair et al. .................. 514/12

FOREIGN PATENT DOCUMENTS

| EP | 1551964 | * | 2/2004 |
|---|---|---|---|
| JP | 2004 261136 | | 9/2004 |
| JP | 2004-261136 | * | 9/2004 |
| WO | WO 89/03887 | | 5/1989 |
| WO | WO 89/10396 | | 11/1989 |
| WO | WO 92/13956 | | 8/1992 |
| WO | WO 96/06932 | | 3/1996 |
| WO | WO 97/13865 | | 4/1997 |
| WO | WO 00/04173 | | 1/2000 |
| WO | WO 2004/016726 | | 2/2004 |
| WO | WO 2004/090140 | | 10/2004 |
| WO | WO 2006/032469 | | 3/2006 |

OTHER PUBLICATIONS

Ashihara et al., Plant Science (2005), vol. 169, pp. 107-114.*
Joshi et al (The Journal of Biological Chemistry vol. 237, No. 3, Mar. 1962).*
Gupta et al (PNAS, vol. 90, p. 1629-1633, Feb. 1993).*
Uchimiya et al (Molecular Breeding 9: 25-31 2002).*
Zhao, Hui-Wu et al., "Construction of a Trehalose-6-Phosphate Synthase Gene Driven by Drought-Responsive Promoter and Expression of Drought-Resistance in Transgenic Tobacco," The National Laboratory of Protein Engineering and Plant Genetic Engineering, College of Life Sciences, Peking University, Beijing 100871, China, vol. 42 (6); pp. 616-619. English Translation included.
Accession No. XP_444840 "hypothetical protein CAGL0A01716g [*Candida glabrata* CBS138]." (2004).
Accession No. XP_456073 "unnamed protein product [*Kluyveromyces lactis*]" (2004).
Accession No. NP_986013 "AFR466Cp [*Ashbya gossypii* ATCC 10895]." (2004).
Accession No. XP_888958 "hypothetical protein CaO19_6684 [*Candida albicans* SC5314]." (2005).
Accession No. XP500320 "hypothetical protein [*Yarrowia lipolytica*]." (2004).
Accession No. XP389372 "hypothetical protein FG09196.1 [*Gibberella zeae* PH-1]."
Accession No. XP_749509 "isochorismatase family hydrolase [*Aspergillus fumigatus* Af293]."(2005).
Accession No. XP_712112 "hypothetical protein CaO19.13976 [*Candida albicans* SC5314]." (2004).
Accession No. BAE56421 "unnamed protein product [*Aspergillus oryzae*]." (2005).
Accession No. XP_567125 "nicotinamidase [*Cryptococcus neoformans* var. *neoformans* JEC21]." (2005).
Accession No. XP_964547 "hypothetical protein NCU00713 [*Neurospora crassa* OR74A]." (2003).
Accession No. XP_712135 "hypothetical protein CaO19.14000 [*Candida albicans* SC5314]."(2004).
Accession No. XP_448179 "unnamed protein product [*Candida glabrata*]." (2004).
Accession No. XP_453643 "unnamed protein product [*Kluyveromyces lactis*]."(2004).
Accession No. NP_987024 "AGR358Wp [*Ashbya gossypii* ATCC 10895]." (2004).
Accession No. XP_500272 "hypothetical protein [*Yarrowia lipolytica*]." (2004).
Accession No. XP_722371 "hypothetical protein CaO19.9035 [*Candida albicans* SC5314]." (2004).
Accession No. XP_456405 "hypothetical protein DEHA0A01969g [*Debaryomyces hansenii* CBS767]." (2004).
Accession No. BAE61562 "unnamed protein product [*Aspergillus oryzae*]." (2005).
Accession No. XP_759702 "hypothetical protein UM03555.1 [*Ustilago maydis* 521]." (2003).

(Continued)

*Primary Examiner* — Anne Grunberg
*Assistant Examiner* — Lee Visone
(74) *Attorney, Agent, or Firm* — Hunton & Williams LLP

(57) ABSTRACT

Stress tolerance in plants and plant cells is achieved by using nucleotide sequences encoding enzymes involved in the NAD salvage synthesis pathway and/or the NAD de novo synthesis pathway from fungal or yeast like organisms other than *Saccharomyces cereviseae*, e.g., for overexpression in plants.

7 Claims, No Drawings

OTHER PUBLICATIONS

Accession No. EAL18079 "hypothetical protein CNBK1000 [*Cryptococcus neoformans* var. *neoformans* B-3501A]." (2004).
Accession No. NP_587771 "glutamine-dependent NAD(+) synthetase (predicted) [*Schizosaccharomyces pombe*]." (2002).
Accession No. XP_681472 "hypothetical protein AN8203.2 [*Aspergillus nidulans* FGSC A4]." (2005).
Accession No. XP_959191 "hypothetical protein NCU04648 [*Neurospora crassa* OR74A]"(2003).
Accession No. XP_567726 "NAD+ synthase (glutamine-hydrolyzing) [*Cryptococcus neoformans* var. *neoformans* JEC21]."(2005).
Accession No. EAQ90706 "conserved hypothetical protein [*Chaetomium globosum* CBS 148.51]."(2004).
Accession No. XP_387574 "hypothetical protein FG07398.1 [*Gibberella zeae* PH-1]." (2008).
Accession No. XP_748008 "glutamine dependent NAD+ synthetase [*Aspergillus fumigatus* Af293]."(2005).
Accession No. XP_361704 "hypothetical protein MGG_04178 [*Magnaporthe grisea* 70-15]."(2005).
Accession No. Q06178 "Nicotinamide-nucleotide adenylyltransferase 1 (NAD(+)pyrophosphorylase 1) (NAD(+) diphosphorylase 1) (NMN adenylyltransferase 1)." (1997).
Accession No. XP_444815 "hypothetical protein CAGL0A01023g [*Candida glabrata* CBS138]." (2004).
Accession No. NP_986687 "AGR022Cp [*Ashbya gossypii* ATCC 10895]."(2004).
Accession No. XP_453005 "unnamed protein product [*Kluyveromyces lactis*]." (2004).
Accession No. XP_458184 "hypothetical protein DEHA0C12639g [*Debaryomyces hansenii* CBS767]." (2004).
Accession No. XP_718656 "hypothetical protein CaO19.7499 [*Candida albicans* SC5314]." (2004).
Accession No. XP_504391 "hypothetical protein [*Yarrowia lipolytica*]." (2004).
Accession No. NP_592856 "nicotinamide mononucleotide (NMN) adenylyltransferase (predicted) [*Schizosaccharomyces pombe*]."(2002).
Accession No. XP_762639 "hypothetical protein UM06492.1 [*Ustilago maydis* 521]." (2003).
Accession No. XP_571297 "nicotinate-nucleotide adenylyltransferase [*Cryptococcus neoformans* var. *neoformans* JEC21]." (2005).
Accession No. BAE57070 "unnamed protein product [*Aspergillus oryzae*]."(2005).
Accession No. XP_750776 "nicotinamide mononucleotide adenylyl transferase [*Aspergillus fumigatus* Af293]." (2005).
Accession No. XP_659349 "hypothetical protein AN1745.2 [*Aspergillus nidulans* FGSC A4]." (2005).
Accession No. XP_389652 "hypothetical protein FG09476.1 [*Gibberella zeae* PH-1]." (2008).
Accession No. XP_957634 "hypothetical protein NCU04019 [*Neurospora crassa* OR74A]." (2003).
Accession No. XP_363364 "hypothetical protein MGG_01290 [*Magnaporthe grisea* 70-15]." (2005).
Accession No. XP_758179 "hypothetical protein UM02032.1 [*Ustilago maydis* 521]."(2003).
Accession No. EAQ85219 "hypothetical protein CHGG_09233 [*Chaetomium globosum* CBS 148.51]." (2004).
Accession No. CAA85352 "putative nicotinate phosphorybosyltranferase [*Saccharomyces cerevisiae*]."(1994).
Accession No. XP_448893 "unnamed protein product [*Candida glabrata*]." (2004).
Accession No. XP_453357 "unnamed protein product [*Kluyveromyces lactis*]." (2004).
Accession No. NP_983562 "ACR160Cp [*Ashbya gossypii* ATCC 10895]." (2004).
Accession No. XP_462577 "hypothetical protein DEHA0G25201g [*Debaryomyces hansenii* CBS767]."(2004).
Accession No. XP_889008 "hypothetical protein CaO19_7176 [*Candida albicans* SC5314]." (2005).
Accession No. XP_500338 "hypothetical protein [*Yarrowia lipolytica*]." (2004).
Accession No. XP_746744 "nicotinate phosphoribosyltransferase [*Aspergillus fumigatus* Af293]." (2005).
Accession No. BAE64333 "unnamed protein product [*Aspergillus oryzae*]." (2005).
Accession No. XP_965789 "hypothetical protein NCU00649 [*Neurospora crassa* OR74A]." (2003).
Accession No. EAQ93453 "hypothetical protein CHGG_01688 [*Chaetomium globosum* CBS 148.51]." (2004).
Accession No. XP_682385 "hypothetical protein AN9116.2 [*Aspergillus nidulans* FGSC A4]." (2005).
Accession No. AAN74808 "Npt1p [*Gibberella moniliformis*]."(1999).
Accession No. Q9UTK3 "Probable nicotinate phosphoribosyltransferase (NAPRTase)."(2002).
Accession No. XP_361075 "hypothetical protein MGG_13498 [*Magnaporthe grisea* 70-15]." (2005).
Accession No. EAL18922 "hypothetical protein CNBI1830 [*Cryptococcus neoformans* var. *neoformans* B-3501A]." (2004).
Accession No. XP_568039 "nicotinate phosphoribosyltransferase [*Cryptococcus neoformans* var. *neoformans* JEC21]." (2005).
Accession No. XP_760597 "hypothetical protein UM04450.1 [*Ustilago maydis* 521]." (2003).
Accession No. NP_011524 "Nicotinic acid mononucleotide adenylyltransferase, involved in NAD(+) salvage pathway; Nma2p [*Saccharomyces cerevisiae*]."(1997).
An, et al. (1996) The Plant Cell 8: 15-30.
Anderson, et al. (2003) Nature 423: 181-185.
Harpster, et al. (1988) Mol. Gen. Genet. 212: 182-190.
Gallo, et al. (2004) Nicotinamide Clearance by Pnc1 Directly Regulates Sir2-Mediated Silencing and Longevity, Molecular and Cellular Biology.
Hudspeth, et al. (1989) Plant Mol Biol 12: 579-589.
Hunt, et al. (Jul. 2004) "NAD—new roles in signaling and gene regulation in plants." New Phytologist 163(1): 31-44.
Keil, et al. (1989) EMBO J 8: 1323-1330.
Keller, et al. (1988) EMBO J 7: 3625-3633.
Keller, et al. (1989) Genes Devel. 3: 1639-1646.
Peleman, et al. (1989) Gene 84: 359-369.
Uchimiya, et al. (2002) Molecular Breeding 9: 25-31.
Uchimiya, et al. (Apr. 10-15, 2003) Keystone Symposium on Plant Biology: Functions and Control of Cell Death, Snowbird Utah.
Wang, et al. (2003) Planta 218: 1-14.

* cited by examiner

SEQUENCE LISTING

```
<160> NUMBER OF SEQ ID NOS: 66

<210> SEQ ID NO 1
<211> LENGTH: 211
<212> TYPE: PRT
<213> ORGANISM: Candida glabrata

<400> SEQUENCE: 1

Met Lys Thr Leu Leu Val Ile Asp Val Gln Asn Asp Phe Ile Thr Pro
1               5                   10                  15

Asp His Ser Met Tyr Val Pro Gln Gly Glu Glu Val Val Ser Pro Ile
            20                  25                  30

Val Glu Leu Met Lys Asp Pro Gln Trp His Arg Val Val Val Ser Arg
        35                  40                  45

Asp Trp His Pro Gln Asn His Ile Ser Phe Ala Lys Asn His Gly Val
    50                  55                  60

Glu Asp Tyr Thr Glu Thr Thr Tyr Lys Ser Pro Arg Pro Gly Asp Asp
65                  70                  75                  80

Ser Thr Gln Pro Ala Thr Leu Trp Pro Val His Cys Val Gln Asn Thr
                85                  90                  95

Arg Gly Ala Gln Leu Ala Pro Asp Ile Leu Glu Leu Val Asn Ser Lys
            100                 105                 110

His Ile Lys Ile Val Asp Lys Gly Tyr Leu Ser Asn Cys Glu Tyr Tyr
        115                 120                 125

Ser Ala Phe Asn Asp Thr Trp Glu Trp His Lys Thr Glu Leu Asp Glu
    130                 135                 140
```

```
Tyr Leu Lys Lys His His Thr Thr Glu Val Tyr Val Gly Leu Ala
145                 150                 155                 160

Leu Asp Phe Cys Val Lys Asn Thr Ala Ile Ser Ala Ala Lys Leu Gly
            165                 170                 175

Tyr Asp Thr Thr Ile Leu Lys Asp Tyr Thr Lys Pro Ile Tyr Thr Asp
            180                 185                 190

Glu Asp His Gln Gln Gln Leu Glu Lys Asp Leu Lys Glu His Asn Val
            195                 200                 205

Lys Val Lys
        210

<210> SEQ ID NO 2
<211> LENGTH: 218
<212> TYPE: PRT
<213> ORGANISM: Kluyveromyces lactis

<400> SEQUENCE: 2

Met Gly Ala Arg Ala Leu Leu Val Ile Asp Ile Gln Asn Asp Phe Leu
1               5                   10                  15

Pro Pro Lys Gly Ser Leu Ala Val Gln Asp Gly Asp Thr Ile Ile Asp
            20                  25                  30

Pro Val Ile Gln Leu Leu Gln Asp Gln Asp Trp Asp Cys Val Ala Met
            35                  40                  45

Thr Lys Asp Trp His Pro Pro Asp His Ile Ser Phe Ala Lys Asn His
    50                  55                  60

Gly Leu Pro Asp Phe Ser Ser Phe Thr Tyr Asp Ser Pro Val Pro Gly
65              70                  75                  80

Ser Thr Glu Lys Gln Ser Ala Thr Leu Trp Pro Val His Cys Val Gln
                85                  90                  95

Glu Thr Trp Gly Ser Glu Val Pro Glu Lys Leu Leu Ala Glu Ile Leu
            100                 105                 110

Lys Leu Lys Val Pro His Lys Ile Val Asn Lys Gly Tyr Leu Ser Asp
            115                 120                 125

Arg Glu Tyr Tyr Ser Gly Phe Asn Asp Ile Trp Asn Asp His His Thr
130                 135                 140

Glu Leu Asp Ala Phe Phe Lys Glu Asn Asp Val Thr Glu Ile Tyr Val
145                 150                 155                 160

Val Gly Leu Ala Phe Asp Phe Cys Val Lys Asn Ser Ala Ile Ser Ala
                165                 170                 175

Ala Asn Leu Gly Tyr His Val Thr Ile Leu Lys Asp Tyr Thr Lys Ala
            180                 185                 190

Ile Ala Asn Asp Leu Gln Ser Ile Glu Ser Phe Ile Gln Glu Leu Ala
            195                 200                 205

Lys Asn Glu Val Ser Val Gln Glu Ser Ile
        210                 215

<210> SEQ ID NO 3
<211> LENGTH: 218
<212> TYPE: PRT
<213> ORGANISM: Eremothecium gossypii

<400> SEQUENCE: 3

Met Ser Lys Ala Leu Ile Val Val Asp Val Gln Asn Asp Phe Ala Asp
1               5                   10                  15

Ala Arg Gly Ala Leu Ala Val Pro Gly Ala His Glu Ile Val Gln Pro
            20                  25                  30
```

-continued

```
Leu Ala Glu Leu Ala Gln Asp Pro Arg Trp Ala Tyr Val Ala Met Thr
             35                  40                  45

Arg Asp Trp His Pro Pro Asp His Val Ser Phe Ala Asp Thr His Gly
 50                  55                  60

Arg Pro Pro Phe Ser Pro Tyr Met Tyr His Pro Pro Gly Val Arg
 65                  70                  75                  80

Ala Pro Pro Gln Ala Gly Thr Leu Trp Pro Thr His Cys Val Gln Gly
                 85                  90                  95

Ser Trp Gly Ala Gln Leu Ala Pro Gln Leu Ala Ala Ala Arg Ser Leu
                100                 105                 110

Pro His Ser Val Val Asp Lys Gly Val Trp Pro Asp Arg Glu Cys Tyr
            115                 120                 125

Ser Ala Phe Glu Asp Ile Trp Ala Asp Arg Ser Ser Gly Leu Asp Gly
        130                 135                 140

Leu Leu Arg Ser His Gly Val Lys His Val Tyr Val Ala Gly Leu Ala
145                 150                 155                 160

Leu Asp Tyr Cys Val Lys Ser Thr Ala Ile Ser Ala Ala Arg Leu Gly
                165                 170                 175

Tyr Thr Thr Thr Ile Leu Leu Asp Tyr Thr Arg Ala Ile Ala Ala Asp
            180                 185                 190

Ala Gln Ser Met Ala Arg Leu Ser Ser Asp Leu Ala Gly His Gln Val
        195                 200                 205

Ala Leu Cys Glu Gly Ala Glu Pro Leu Pro
    210                 215

<210> SEQ ID NO 4
<211> LENGTH: 244
<212> TYPE: PRT
<213> ORGANISM: Candida albicans

<400> SEQUENCE: 4

Met Lys Lys Thr Ala Leu Ile Val Val Asp Leu Gln Glu Asp Phe Leu
  1               5                  10                  15

Pro Pro Asn Gly Ser Leu Ala Ile Lys Asn Gly Arg Ser Val Ile Pro
             20                  25                  30

Lys Ile Asn Gln Leu Leu Pro Ser Gln Asp Asn His Ser Lys Phe Asp
         35                  40                  45

Trp Ser Leu Ile Val Ala Thr Gln Asp Trp His Pro Pro Asn His Thr
 50                  55                  60

Ser Phe Ala Ser Gln His Glu Asn Val Ala Pro Phe Thr Glu Ile Glu
 65                  70                  75                  80

Phe Ile His Pro Glu Lys Lys Leu Asp Pro Lys Thr Asn Gln Pro Ile
                 85                  90                  95

Val Met Asn Gln Ile Val Trp Pro Asp His Cys Val Gln Gly Thr Lys
            100                 105                 110

Gly Ala Gln Leu Glu Pro Ser Phe Ala Asn Gln Phe Glu Lys Leu Thr
        115                 120                 125

Lys Gln Asp Asp Asn Asn Thr Ala Pro Cys Lys Ile Val Lys Lys Gly
    130                 135                 140

Tyr Leu Pro Asp Arg Glu Tyr Tyr Ser Cys Phe Gln Asp Cys Trp Gly
145                 150                 155                 160

Leu His His Thr Glu Leu Ile Asp Leu Leu His Glu Tyr Asp Ile Glu
                165                 170                 175

Asn Val Val Phe Val Gly Leu Ala Tyr Asp Phe Cys Val Leu Ser Ser
            180                 185                 190
```

```
Ala Ile Asp Ser Ala Lys Asn Gly Phe Lys Thr Phe Val Lys Asn
        195                 200                 205

Tyr Cys Glu Ser Val Tyr Pro Glu Lys Ile Asn Asp Thr Asp Lys Leu
210                 215                 220

Phe Ile Asp Asn Gly Val Thr Ile Val Asp Asn Asp Glu Lys Phe Asp
225                 230                 235                 240

Ser Leu Phe Lys
```

<210> SEQ ID NO 5
<211> LENGTH: 203
<212> TYPE: PRT
<213> ORGANISM: Yarrowia lipolytica

<400> SEQUENCE: 5

```
Met Ala Ala Leu Ile Ile Val Asp Leu Gln Asn Asp Phe Leu Pro Gly
1               5                   10                  15

Gly Ser Leu Ala Val Val Asp Gly Asn Asp Ile Ile Pro Ile Val Gln
            20                  25                  30

Lys Leu Ala Asp Ser Gly Lys Tyr Lys Phe Val Val Ala Thr Lys Asp
        35                  40                  45

Ser His Pro Gln Asp His Thr Ser Phe Ala Ala Asn His Gly Ala Glu
    50                  55                  60

Pro Phe Thr Ser Ile Thr Phe Lys His Pro Asn Ser Asp Lys Gln Val
65                  70                  75                  80

Asp His Thr Val Trp Pro Val His Cys Val Glu Gly Thr Ser Gly Ala
                85                  90                  95

Asp Tyr Pro Pro Ser Phe Asp Ser Ser Asn Val Gln Ala Leu Val Arg
            100                 105                 110

Lys Gly Tyr Leu Gln Asp Arg Glu Tyr Tyr Ser Gly Phe Glu Asp Val
        115                 120                 125

Trp Gly Ile His Lys Thr Glu Leu His Asp Leu Leu Gln Gln Asn Gly
    130                 135                 140

Val Thr Glu Val Asp Val Val Gly Leu Ala Phe Asp Tyr Cys Val Phe
145                 150                 155                 160

Asn Thr Ala Lys Asp Ala Ala Lys Arg Gly Tyr Lys Thr Thr Val Ile
                165                 170                 175

Arg Glu Ala Thr Lys Pro Val Asp Pro Ser Ser Glu Lys Lys Ile Val
            180                 185                 190

Ala Ser Leu Glu Glu Ala Gly Val His Val Val
        195                 200
```

<210> SEQ ID NO 6
<211> LENGTH: 223
<212> TYPE: PRT
<213> ORGANISM: Giberella zeae

<400> SEQUENCE: 6

```
Met Thr Ser Gln Lys Ser Phe Lys Pro Ala Leu Ile Ile Val Asp Phe
1               5                   10                  15

Gln Glu Asp Phe Cys Pro Pro Asn Gly Ser Leu Ala Val Pro Glu Gly
            20                  25                  30

Arg Thr Ile Ala Pro Thr Ile Asn Thr Leu Thr Ala Leu Pro Phe His
        35                  40                  45

Leu Ile Leu Ala Thr Lys Asp Phe His Pro Pro Ser His Ile Ser Phe
    50                  55                  60

Ala Ser Asn His Pro Ser Ser Thr Pro Tyr Thr Ser Thr Thr Thr Ile
65                  70                  75                  80
```

```
Thr His Pro Arg Asp Ser Ser Arg Ser Tyr Thr Thr Thr Leu Trp Pro
                85                  90                  95

Thr His Cys Val Gln Gly Thr Pro Gly Ala Asp Leu Val Pro Glu Leu
            100                 105                 110

Asp Val Ser Arg Leu His Ala Val Ile Glu Lys Gly Gln Asp Lys Arg
        115                 120                 125

Val Glu Met Tyr Ser Ala Phe Tyr Asp Pro Phe Arg Val Ser Asp Ser
    130                 135                 140

Gly Leu Ala Gly Met Leu Gly Glu Gln Asn Val Thr Asp Val Phe Val
145                 150                 155                 160

Val Gly Leu Ala Ala Asp Phe Cys Val Lys Ala Thr Ala Glu Asp Ala
                165                 170                 175

Val Lys Glu Gly Tyr Ser Thr Trp Ile Val Asn Glu Gly Thr Lys Pro
            180                 185                 190

Val Met Pro Asp Lys Trp Asp Glu Cys Arg Lys Gly Met Glu Asp Met
        195                 200                 205

Gly Ile Lys Phe Thr Ser Val Ala Asn Ala Val Asp Lys Phe Lys
    210                 215                 220

<210> SEQ ID NO 7
<211> LENGTH: 235
<212> TYPE: PRT
<213> ORGANISM: Aspergillus fumigatus

<400> SEQUENCE: 7

Met Lys Ala Ala Leu Ile Val Val Asp Met Gln Glu Asp Phe Cys Pro
1               5                   10                  15

Pro Asp Gly Ser Leu Ala Val Gln Gly Ala Arg Ser Ile Ala Pro Leu
            20                  25                  30

Ile Asn Ser Leu Leu Ala Asn Pro Gly Phe Val Ile Arg Val Ala Ser
        35                  40                  45

Gln Asp Tyr His Pro Arg Asp His Val Ser Phe Ala Ser Asn His Pro
    50                  55                  60

Glu Pro Asn Asn Arg Pro Phe Glu Ser Val Ile Gln Met Asn Asn Pro
65                  70                  75                  80

Ala Pro Gly Lys Glu Ser Glu Thr Lys Glu Gln Arg Leu Trp Pro Val
                85                  90                  95

His Cys Val Gly Gly Thr Lys Gly Ala Thr Ile Ile Pro Glu Ile Asp
            100                 105                 110

Ser Ser Lys Ile Asp Leu His Val Lys Lys Gly Met Asp Ser Arg Val
        115                 120                 125

Glu Met Tyr Ser Ala Phe Ser Asp Ala Phe Gly Asn Leu Asp Pro Ala
    130                 135                 140

Val His Thr Gln Ser Val Asp Val Asp Leu Lys Ala Val Leu Ala Glu
145                 150                 155                 160

Arg Gly Ile Thr His Val Phe Ser Ala Gly Ile Ala Gly Asp Tyr Cys
                165                 170                 175

Val Lys Tyr Thr Ala Met Asp Ala Ala Arg Ala Gly Phe Lys Ser Phe
            180                 185                 190

Leu Val Glu Asp Ala Thr Arg Ser Val Asp Ser Gly Ala Gly Trp Glu
        195                 200                 205

Glu Ala Arg Arg Glu Cys Glu Ala Ala Gly Val Ser Ile Ile Gln Ser
    210                 215                 220

Asp Gly Pro Glu Ile Ala Ala Leu Thr Ala Ser
225                 230                 235
```

<210> SEQ ID NO 8
<211> LENGTH: 165
<212> TYPE: PRT
<213> ORGANISM: Candida albicans

<400> SEQUENCE: 8

```
Met Lys Lys Thr Ala Leu Ile Val Val Asp Leu Gln Glu Asp Phe Leu
1               5                   10                  15

Pro Pro Asn Gly Ser Leu Ala Ile Lys Asn Gly Arg Ser Val Ile Pro
            20                  25                  30

Lys Ile Asn Gln Leu Leu Pro Ser Gln Asp Asn His Ser Lys Phe Asp
        35                  40                  45

Trp Ser Leu Ile Val Ala Thr Gln Asp Trp His Pro Pro Asn His Thr
    50                  55                  60

Ser Phe Ala Ser Gln His Glu Asn Val Ala Pro Phe Thr Glu Ile Glu
65                  70                  75                  80

Phe Ile His Pro Glu Lys Lys Leu Asp Pro Lys Thr Asn Gln Pro Ile
                85                  90                  95

Val Met Asn Gln Ile Val Trp Pro Asp His Cys Val Gln Gly Thr Lys
            100                 105                 110

Gly Ala Gln Leu Glu Pro Ser Phe Ala Asn Gln Phe Glu Lys Leu Thr
        115                 120                 125

Lys Gln Asp Asp Asn Asn Thr Ala Pro Cys Lys Ile Val Lys Lys Gly
    130                 135                 140

Tyr Leu Pro Asp Arg Glu Tyr Tyr Ser Cys Phe Gln Asp Cys Trp Gly
145                 150                 155                 160

Tyr Ile Ile Ser Asn
                165
```

<210> SEQ ID NO 9
<211> LENGTH: 234
<212> TYPE: PRT
<213> ORGANISM: Aspergillus oryzae

<400> SEQUENCE: 9

```
Met Lys Ala Ala Leu Val Val Asp Met Gln Glu Asp Phe Cys Pro
1               5                   10                  15

Pro Asn Gly Val Leu Pro Val Gln Glu Gly Arg Ala Ile Ala Pro Ile
            20                  25                  30

Ile Asn Glu Leu Leu Ala His Gln Gly Phe Ala Val Arg Val Ala Thr
        35                  40                  45

Gln Asp Tyr His Pro Val Asp His Ile Ser Phe Ala Asn Ser His Pro
    50                  55                  60

Arg Pro Asn Asn Arg Pro Phe Glu Ser Val Ile Thr Val Asn Asn Pro
65                  70                  75                  80

Ala Pro Gly Lys Glu His Glu Thr Lys Pro Gln Asn Leu Trp Pro Ala
                85                  90                  95

His Cys Val Gly Glu Thr Arg Gly Ala Glu Ile Ile Pro Glu Ile Gln
            100                 105                 110

Thr Asp Asn Ile Asp Leu Tyr Val Lys Lys Gly Met His Ser Gln Val
        115                 120                 125

Glu Met Tyr Ser Ala Phe Ala Asp Ala Phe Gly Asn Val Asp Pro Ser
    130                 135                 140

Ile Thr Asp Gln Ser Val Asp Ala Asp Leu Lys Asp Phe Leu Ala Ser
145                 150                 155                 160
```

```
Lys Gly Val Thr Asp Val Phe Val Gly Leu Ala Gly Asp Tyr Cys
            165                 170                 175

Val Lys His Thr Ala Ile Asp Ala Ala Arg Val Gly Phe Lys Ser Tyr
        180                 185                 190

Val Val Glu Asn Ala Ile Arg Cys Val Val Pro Gly Ser Gly Trp Asp
            195                 200                 205

Gly Ala Lys Arg Glu Leu Arg Glu Ala Gly Val Ser Ile Ile Gln Ser
            210                 215                 220

Asn Gly Pro Glu Ile Ser Gly Leu Ala Ile
225                 230
```

<210> SEQ ID NO 10
<211> LENGTH: 225
<212> TYPE: PRT
<213> ORGANISM: Cryptococcus neoformans

<400> SEQUENCE: 10

```
Met Ala Ser Met Pro Ala Ser Thr Ala Leu Ile Ile Val Asp Val Gln
1               5                   10                  15

Asn Asp Phe Leu Pro Pro Thr Gly Ser Leu Ala Val Pro Asn Gly Arg
            20                  25                  30

Glu Val Leu Pro Val Ile Thr Gly Leu Leu Asp Arg Lys Trp Asp Trp
        35                  40                  45

Ala Val Val Val Ser Gln Asp Tyr His Pro Lys Gly His Ile Ser
    50                  55                  60

Phe Ala Ser Ala His Pro Pro Asn Gln Ala Tyr Thr Gln Leu Pro Leu
65                  70                  75                  80

Val Asn Ala His Gly Glu Ser Tyr Ile Gln Thr Leu Trp Pro Asp His
                85                  90                  95

Cys Ile Gln Gly Thr Ala Gly Ala Asp Leu Glu Ser Gly Leu Ala Glu
            100                 105                 110

Val Leu Ala Lys Arg Gly Asp Gly Ile His Ser Lys Leu Glu Ala Tyr
        115                 120                 125

Ser Ala Phe Gln Glu Ile Val Pro Pro Lys Thr Ser Glu Leu Ala Glu
    130                 135                 140

Phe Leu Leu Ala Gln Gly Val Asn Lys Val Val Ile Ala Gly Val Ala
145                 150                 155                 160

Thr Asp Phe Cys Val Leu Gln Thr Ala Leu Ser Ser Ile Ser Ser Ser
                165                 170                 175

Phe Pro Thr Leu Leu Ile Ala Pro Ala Met Arg Ala Ile Ser Pro Glu
            180                 185                 190

Tyr Glu Ala Lys Thr Phe Glu Ala Val Glu Ser Leu Gly Gly Val Ile
        195                 200                 205

Leu Gly Arg Asn Gly Glu Glu Trp Lys Thr Lys Leu Ala Glu Trp Ile
    210                 215                 220

Arg
225
```

<210> SEQ ID NO 11
<211> LENGTH: 297
<212> TYPE: PRT
<213> ORGANISM: Neurospora crassa

<400> SEQUENCE: 11

```
Met Gly Phe Leu Glu Trp Leu Met Pro Pro Ser Ile Phe Asn Val Phe
1               5                   10                  15

Gln Thr Arg Leu Leu Glu Asn Gly Gln Gly Ala Gln Pro Glu Pro Asp
```

```
            20                  25                  30
Phe Arg Pro Ala Leu Leu Val Val Asp Met Gln Glu Asp Phe Cys Pro
         35                  40                  45

Pro Asn Gly Thr Leu Ala Val Thr Gly Gly Arg Ser Ile Thr Pro Leu
     50                  55                  60

Ile Asn Thr Leu Leu Ser Ser Pro Leu Phe Val Leu Arg Ile Ala Thr
 65                  70                  75                  80

Lys Asp Trp His Pro Pro Asn His Ile Ser Phe Ala Ser Asn His Asn
                 85                  90                  95

His Ala Ser Ser Pro Ser Pro Cys Cys Pro Asp Ser Ser Gly Lys Ala
             100                 105                 110

Ala Ile Pro Phe Leu Ser Thr Thr Val His Asn Pro His Asn Pro
         115                 120                 125

Ser Glu Ser Tyr Thr Thr Arg Leu Trp Pro Ser His Cys Ile Ala Asp
     130                 135                 140

Thr Pro Gly Ala Ser Leu Ile Pro Glu Leu Asp Val Ser Lys Ile Asp
145                 150                 155                 160

Gln Ile Leu Glu Lys Gly Thr Asn Arg Leu Val Glu Met Tyr Ser Ala
                 165                 170                 175

Phe Tyr Asp Pro Phe Thr Ser Pro Arg Val Ser Asp Ser Gly Leu Ala
             180                 185                 190

His Met Leu Arg Glu Ala Lys Val Thr His Val Tyr Val Val Gly Leu
         195                 200                 205

Ala Ala Asp Tyr Cys Val Trp Ser Thr Ala Met Asp Ala His Asn Glu
     210                 215                 220

Gly Phe Glu Thr Val Val Val Glu Gly Ala Thr Lys Pro Val Asp Glu
225                 230                 235                 240

Asp Gly Trp Arg Arg Cys Lys Glu Ala Leu Val Gly Glu Pro Gly Val
                 245                 250                 255

Arg Val Val Arg Trp Glu Gly Glu Val Arg Arg Leu Phe Pro Gly
             260                 265                 270

Gly Leu Val Thr Thr Thr Val Gly Ala Gly Asn Asp Glu Glu Val Val
         275                 280                 285

Glu Glu Glu Glu Glu Glu Glu Lys Ile
     290                 295

<210> SEQ ID NO 12
<211> LENGTH: 121
<212> TYPE: PRT
<213> ORGANISM: Candida albicans

<400> SEQUENCE: 12

Met Lys Lys Thr Ala Leu Ile Val Val Asp Leu Gln Glu Asp Phe Leu
 1               5                  10                  15

Pro Pro Asn Gly Ser Leu Ala Ile Lys Asn Gly Arg Ser Val Ile Pro
             20                  25                  30

Lys Ile Asn Gln Leu Leu Pro Ser Gln Asp Asn His Ser Lys Phe Asp
         35                  40                  45

Trp Ser Leu Ile Val Ala Thr Gln Asp Trp His Pro Pro Asn His Thr
     50                  55                  60

Ser Phe Ala Ser Gln His Glu Asn Val Ala Pro Phe Thr Glu Ile Glu
 65                  70                  75                  80

Phe Ile His Pro Glu Lys Lys Leu Asp Pro Lys Thr Asn Gln Pro Ile
                 85                  90                  95

Val Met Asn Gln Ile Val Trp Pro Asp His Cys Val Gln Gly Thr Lys
```

Gly Ala Gln Leu Glu Pro Ser Phe Ala
            115                 120

<210> SEQ ID NO 13
<211> LENGTH: 713
<212> TYPE: PRT
<213> ORGANISM: Candida glabrata

<400> SEQUENCE: 13

Met Ser His Leu Val Thr Leu Ala Thr Cys Ser Leu Asn Gln Trp Ala
1               5                   10                  15

Leu Asp Phe Glu Gly Asn Arg Asp Arg Ile Leu Glu Ser Ile Arg Ile
            20                  25                  30

Ala Lys Glu Arg Gly Ala Arg Leu Arg Val Gly Pro Glu Leu Glu Ile
        35                  40                  45

Ser Gly Tyr Gly Cys Leu Asp His Phe Leu Glu Asn Asp Val Cys Leu
    50                  55                  60

His Ser Trp Glu Met Tyr Ala Gln Ile Leu Lys Asn Pro Glu Thr His
65                  70                  75                  80

Gly Leu Ile Leu Asp Ile Gly Met Pro Leu His Lys Asn Val Arg
                85                  90                  95

Tyr Asn Cys Arg Leu Leu Ser Leu Asp Gly Lys Ile Leu Phe Ile Arg
                100                 105                 110

Pro Lys Ile Trp Leu Ala Asn Asp Gly Asn Tyr Arg Glu Met Arg Phe
            115                 120                 125

Phe Thr Pro Trp Met Lys Pro Gly Val Val Glu Leu Thr Leu Pro
    130                 135                 140

Pro Met Ile Gln Lys Ile Thr Gly Gln Lys Lys Val Pro Phe Gly Asp
145                 150                 155                 160

Ala Val Ile Asn Thr Leu Asp Thr Cys Ile Gly Ala Glu Thr Cys Glu
                165                 170                 175

Glu Val Phe Thr Pro Gln Ser Pro His Ile Ala Met Ser Leu Asp Gly
            180                 185                 190

Val Glu Ile Ile Thr Asn Ser Ser Gly Ser His His Glu Leu Arg Lys
        195                 200                 205

Leu Asn Lys Arg Leu Glu Leu Ile Leu Asn Gly Thr Gly Arg Cys Gly
    210                 215                 220

Gly Val Tyr Leu Tyr Ala Asn Gln Lys Gly Cys Asp Gly Asp Arg Leu
225                 230                 235                 240

Tyr Tyr Asp Gly Cys Ala Leu Ile Ala Ile Asn Gly Lys Ile Leu Ala
                245                 250                 255

Gln Gly Lys Gln Phe Ser Leu Asp Asp Val Glu Val Val Thr Ala Thr
            260                 265                 270

Val Asp Leu Glu Glu Val Arg Asn His Arg Ala Asn Val Met Ser Arg
        275                 280                 285

Gly Leu Gln Ser Ser Leu Ala Asp Leu Lys Tyr Glu His Ile Asp Val
    290                 295                 300

Glu Ile Glu Leu Ala Pro Arg Gly Ser Arg Phe Asn Pro Lys Ile Thr
305                 310                 315                 320

Pro Thr Lys Ser Arg Asp Val Tyr His Thr Pro Glu Glu Ile
                325                 330                 335

Ala Leu Gly Pro Ala Cys Trp Leu Trp Asp Tyr Ile Arg Arg Cys Asn
            340                 345                 350

Gly Thr Gly Tyr Phe Leu Pro Leu Ser Gly Gly Ile Asp Ser Cys Ala

```
                355                 360                 365
Thr Ala Met Ile Ile His Ser Met Cys Arg Leu Val His Lys Ala Cys
        370                 375                 380

His Glu Gly Asn Asp Leu Val Leu Lys Asp Ile Arg Arg Ile Thr Arg
385                 390                 395                 400

Ser Pro Asp Asp Trp Ile Pro Glu Asn Pro Gln Glu Ile Ala Asn Lys
                405                 410                 415

Met Phe His Thr Cys Phe Met Gly Thr Glu Asn Ser Ser Val Glu Thr
        420                 425                 430

Arg Ser Arg Ser Lys Gln Leu Ala Glu Lys Ile Gly Ser Tyr His Val
    435                 440                 445

Asp Leu Asn Met Asp Gly Leu Val Ser Ser Val Ser Leu Phe Glu
        450                 455                 460

Val Ala Thr Gly Arg Lys Pro Ile Phe Lys Ile Phe Gly Gly Ser Gln
465                 470                 475                 480

Ile Glu Asn Leu Ala Leu Gln Asn Ile Gln Ala Arg Leu Arg Met Val
                485                 490                 495

Leu Ala Tyr Leu Phe Ala Gln Leu Leu Pro Trp Val Arg Gly Ile Pro
        500                 505                 510

Asn Ser Gly Gly Leu Leu Val Leu Gly Ser Ala Asn Val Asp Glu Cys
    515                 520                 525

Leu Arg Gly Tyr Leu Thr Lys Tyr Asp Cys Ser Ser Ala Asp Val Asn
530                 535                 540

Pro Ile Gly Gly Ile Ser Lys Thr Asp Leu Lys Gly Phe Ile Lys Tyr
545                 550                 555                 560

Ala Ser Glu Glu Tyr Asp Met Pro Ile Leu Asp Glu Phe Leu Asn Ala
                565                 570                 575

Thr Pro Thr Ala Glu Leu Glu Pro Ile Thr Lys Asp Tyr Val Gln Ser
        580                 585                 590

Asp Glu Arg Asp Met Gly Met Thr Tyr Glu Glu Leu Ser Val Phe Gly
    595                 600                 605

Tyr Leu Arg Lys Val Glu Lys Cys Gly Pro Tyr Ser Met Phe Leu Lys
610                 615                 620

Leu Leu His Glu Trp Thr Pro Arg Leu Thr Pro Ala Gln Val Ala Glu
625                 630                 635                 640

Lys Val Lys Arg Phe Phe Phe Tyr Ala Ile Asn Arg His Lys Gln
                645                 650                 655

Thr Val Leu Thr Pro Ser Tyr His Ala Glu Gln Tyr Ser Pro Asp Asp
        660                 665                 670

Asn Arg Phe Asp Leu Arg Pro Phe Leu Ile Asn Pro Arg Phe Pro Trp
    675                 680                 685

Ala Ser Lys Lys Ile Asp Glu Val Val Lys Gln Cys Glu Gly His Ser
690                 695                 700

Ser Glu Ile Asp Phe Met Thr Ile Asp
705                 710

<210> SEQ ID NO 14
<211> LENGTH: 714
<212> TYPE: PRT
<213> ORGANISM: Kluyveromyces lactis

<400> SEQUENCE: 14

Met Ser Gln Leu Ile Thr Val Ala Thr Cys Asn Leu Asn Gln Trp Ala
1               5                   10                  15

Leu Asp Phe Glu Gly Asn Arg Asp Arg Ile Phe Glu Ser Ile Lys Ile
```

```
                    20                  25                  30
Ala Lys Glu Arg Gly Ala Lys Leu Arg Val Gly Pro Glu Leu Glu Ile
                35                  40                  45

Thr Gly Tyr Gly Cys Leu Asp His Phe Leu Glu Asp Val Phe Leu
    50                  55                  60

His Ser Trp Glu Met Tyr Gly Gln Ile Ile Lys Arg Pro Glu Thr His
65                      70                  75                  80

Gly Ile Leu Leu Asp Ile Gly Met Pro Val Met His Arg Asn Val Arg
                85                  90                  95

Tyr Asn Cys Arg Ile Leu Ser Leu Asp Gly Lys Ile Leu Phe Ile Arg
                100                 105                 110

Pro Lys Ile Trp Leu Ala Asn Asp Gly Asn Tyr Arg Glu Met Arg Phe
            115                 120                 125

Phe Thr Pro Trp Met Lys Ala His Thr Glu Glu Tyr Leu Leu Pro
            130                 135                 140

Pro Met Ile Gln Lys Leu Thr Gly Gln Tyr Arg Ile Pro Phe Gly Asp
145                 150                 155                 160

Ala Val Ile Ser Thr Leu Asp Thr Cys Ile Gly Ala Glu Thr Cys Glu
                165                 170                 175

Glu Leu Phe Thr Pro Gln Ser Pro His Ile Ala Met Ser Leu Asp Gly
            180                 185                 190

Val Glu Ile Phe Thr Asn Ser Ser Gly Ser His His Glu Leu Arg Lys
            195                 200                 205

Leu Asp Lys Arg Leu Asp Leu Ile Met Ser Ala Thr Arg Arg Cys Gly
    210                 215                 220

Gly Val Tyr Leu Tyr Ala Asn Gln Arg Gly Cys Asp Gly Asp Arg Leu
225                 230                 235                 240

Tyr Tyr Asp Gly Cys Ala Leu Ile Cys Val Asn Gly Ser Ile Val Ala
                245                 250                 255

Gln Gly Ser Gln Phe Cys Leu Lys Asp Val Glu Val Val Thr Ala Thr
            260                 265                 270

Val Asp Leu Glu Gln Val Arg Ser Tyr Arg Ser Thr Val Met Ser Arg
    275                 280                 285

Gly Leu Gln Ala Ser Leu Thr Glu Thr Lys Phe Lys Arg Ile Asp Val
    290                 295                 300

Glu Val Glu Leu Ala Thr Leu Asp Asp Arg Phe Asp Ser Thr Leu Val
305                 310                 315                 320

Pro Glu Lys Pro Arg Lys Ala Phe Tyr His Ile Pro Ser Glu Glu Ile
                325                 330                 335

Ala Leu Gly Pro Ala Cys Trp Leu Trp Asp Tyr Leu Arg Arg Cys Asn
                340                 345                 350

Gly Thr Gly Tyr Phe Leu Pro Leu Ser Gly Gly Ile Asp Ser Cys Ala
        355                 360                 365

Thr Ala Val Ile Val His Ser Met Cys Arg Leu Val Val Lys Glu Ala
            370                 375                 380

Ala Glu Gly Asn Gln Gln Val Ile Lys Asp Val Arg Arg Leu Ala Arg
385                 390                 395                 400

Met Asn Asp Glu Trp Ile Pro Lys Thr Pro Gln Glu Leu Ala Asn Lys
                405                 410                 415

Ile Phe Asn Thr Cys Phe Met Gly Thr Glu Asn Ser Ser Lys Glu Thr
            420                 425                 430

Arg Ser Arg Ala Lys Lys Leu Ala Glu His Ile Gly Ala Tyr His Val
    435                 440                 445
```

```
Asp Leu Asn Met Asp Ser Leu Val Ser Ser Met Val Thr Leu Phe Glu
            450                 455                 460

Val Thr Thr Gly Lys Arg Pro Ile Phe Lys Ile Phe Gly Gly Ser Gln
465                 470                 475                 480

Thr Glu Asn Leu Ala Leu Gln Asn Ile Gln Ala Arg Leu Arg Met Val
                485                 490                 495

Leu Ala Tyr Leu Phe Ala Gln Leu Leu Pro Trp Val Arg Ser Ile Pro
            500                 505                 510

Asn Ala Gly Gly Leu Leu Val Leu Gly Ser Ala Asn Val Asp Glu Cys
            515                 520                 525

Leu Arg Gly Tyr Leu Thr Lys Tyr Asp Cys Ser Ser Ala Asp Ile Asn
            530                 535                 540

Pro Ile Gly Gly Ile Ser Lys Thr Asp Leu Lys Lys Phe Ile Ala Tyr
545                 550                 555                 560

Ala Ser Lys Glu Phe Asp Leu Pro Ile Leu Glu Glu Phe Leu Asn Ala
                565                 570                 575

Thr Pro Thr Ala Glu Leu Glu Pro Ile Thr Lys Asn Tyr Val Gln Ser
                580                 585                 590

Asp Glu Ile Asp Met Gly Met Thr Tyr Glu Glu Leu Ser Val Phe Gly
            595                 600                 605

Tyr Leu Arg Lys Val Glu Lys Cys Gly Pro Phe Ser Met Tyr Leu Lys
            610                 615                 620

Leu Leu His Glu Trp Thr Pro Lys Leu Thr Pro Ala Gln Val Ala Glu
625                 630                 635                 640

Lys Val Lys Lys Phe Phe Phe Phe Tyr Ala Ile Asn Arg His Lys Gln
                645                 650                 655

Thr Val Leu Thr Pro Ser Tyr His Ala Glu Gln Tyr Ser Pro Asp Asp
                660                 665                 670

Asn Arg Phe Asp Leu Arg Pro Phe Leu Ile Asn Pro Arg Phe Pro Trp
            675                 680                 685

Ala Phe Lys Lys Ile Asp Asp Ala Val Ala Gln Ser Glu Gly Thr Leu
            690                 695                 700

Ser Gly Ala Leu Asp Val Met Thr Val Glu
705                 710

<210> SEQ ID NO 15
<211> LENGTH: 715
<212> TYPE: PRT
<213> ORGANISM: Eremothecium gossypii

<400> SEQUENCE: 15

Met Ser His Leu Ile Thr Leu Ala Thr Cys Asn Leu Asn Gln Trp Ala
1               5                   10                  15

Leu Asp Phe Glu Gly Asn Arg Asp Arg Ile Leu Glu Ser Ile Arg Ile
            20                  25                  30

Ala Lys Glu Lys Asn Ala Lys Leu Arg Val Gly Pro Glu Leu Glu Val
        35                  40                  45

Ser Gly Tyr Gly Cys Leu Asp His Phe Leu Glu Asp Val Tyr Leu
    50                  55                  60

His Ser Trp Glu Met Tyr Ala Gln Ile Leu Lys Asp Glu Lys Thr His
65                  70                  75                  80

Gly Ile Leu Leu Asp Ile Gly Met Pro Val His Lys Asn Val Arg
                85                  90                  95

Tyr Asn Cys Arg Val Leu Ser Leu Asp Gly His Ile Leu Phe Ile Arg
            100                 105                 110
```

```
Pro Lys Leu Trp Leu Ala Asn Asp Gly Asn Tyr Arg Glu Met Arg Phe
            115                 120                 125

Phe Thr Pro Trp Met Lys Pro Thr Val Val Glu Glu Phe Gln Leu Pro
        130                 135                 140

Pro Val Ile Gln Lys Ile Thr Gly Gln His Ile Ile Pro Phe Gly Asp
145                 150                 155                 160

Ala Val Ile Arg Thr Leu Asp Thr Cys Ile Gly Ala Glu Thr Cys Glu
                165                 170                 175

Glu Leu Phe Thr Pro Gln Ser Pro Asn Ile Ala Met Ser Leu Asp Gly
            180                 185                 190

Val Glu Ile Ile Thr Asn Ser Ser Gly Ser His His Glu Leu Arg Lys
        195                 200                 205

Leu His Lys Arg Leu Asp Leu Ile Leu Gly Ala Thr Gly Arg Cys Gly
210                 215                 220

Gly Val Tyr Leu Tyr Ala Asn Gln Arg Gly Cys Asp Gly Asp Arg Leu
225                 230                 235                 240

Tyr Tyr Asp Gly Cys Ala Leu Ile Ala Val Asn Gly Arg Val Val Ala
                245                 250                 255

Gln Gly Ser Gln Phe Ser Leu Arg Asp Val Glu Val Val Thr Ala Thr
            260                 265                 270

Val Asp Leu Gln Glu Val Arg Asp Tyr Arg Met Ser Val Met Ser Arg
        275                 280                 285

Gly Leu Gln Ala Val Ser Asn Asn Val Thr Phe Glu Arg Ile Gln Val
290                 295                 300

Pro Val Glu Leu Ala Ala Met Gln Asp Arg Phe Asn Pro Thr Ile Asn
305                 310                 315                 320

Leu Thr Lys Ala Lys Ala Pro Tyr Tyr His Ser Pro Glu Glu Glu Ile
                325                 330                 335

Ala Leu Gly Pro Ala Cys Trp Leu Trp Asp Tyr Leu Arg Arg Cys Arg
            340                 345                 350

Gly Thr Gly Tyr Phe Leu Pro Leu Ser Gly Gly Ile Asp Ser Cys Ala
        355                 360                 365

Thr Ala Val Ile Val His Ser Met Cys Arg Met Val Val Lys Glu Ala
370                 375                 380

Ser Glu Gly Asn Leu Gln Val Ile Ala Asp Ala Arg Arg Leu Ala Arg
385                 390                 395                 400

Ala Ser Asp Asp Trp Ile Pro Thr Asp Ala Arg Glu Phe Ala Asn Met
                405                 410                 415

Ile Phe His Thr Cys Phe Met Gly Thr Ala Asn Ser Thr Asn Glu Thr
            420                 425                 430

Arg Ser Arg Ala Lys Lys Leu Ala Glu His Leu Gly Ala Tyr His Val
        435                 440                 445

Asp Leu Asn Met Asp Ser Val Val Lys Ser Val Val Thr Leu Phe Glu
450                 455                 460

Val Thr Thr Gly Lys Arg Pro Ile Phe Lys Val Phe Gly Gly Ser Asn
465                 470                 475                 480

Ile Glu Asn Leu Ala Leu Gln Asn Ile Gln Ala Arg Leu Arg Met Val
                485                 490                 495

Leu Ala Tyr Leu Phe Ala Gln Leu Leu Pro Trp Val Arg Ser Ile Lys
            500                 505                 510

Asn Ser Gly Gly Leu Leu Val Leu Gly Ser Ala Asn Val Asp Glu Cys
        515                 520                 525

Leu Arg Gly Tyr Leu Thr Lys Tyr Asp Cys Ser Ser Ala Asp Ile Asn
530                 535                 540
```

Pro Ile Gly Gly Ile Ser Lys Lys Asp Leu Lys Asn Phe Ile Ser Tyr
545                 550                 555                 560

Ala Ser Lys Glu Phe Asp Leu Pro Ile Leu Arg Glu Phe Val Glu Ala
            565                 570                 575

Thr Pro Thr Ala Glu Leu Glu Pro Ile Thr Glu Asp Tyr Val Gln Ser
        580                 585                 590

Asp Glu Arg Asp Met Gly Met Thr Tyr Glu Glu Leu Ser Val Phe Gly
    595                 600                 605

Tyr Leu Arg Lys Val Glu Lys Cys Gly Pro Tyr Ser Met Phe Leu Lys
610                 615                 620

Leu Leu His Glu Trp Thr Pro Arg Leu Thr Pro Ser Glu Val Ala Glu
625                 630                 635                 640

Lys Val Lys Arg Phe Phe Tyr Phe Tyr Ala Ile Asn Arg His Lys Gln
                645                 650                 655

Thr Val Leu Thr Pro Ser Tyr His Ala Glu Gln Tyr Ser Pro Asp Asp
            660                 665                 670

Asn Arg Phe Asp Leu Arg Pro Phe Leu Ile Asp Pro Arg Phe Ser Trp
        675                 680                 685

Ala Ser Lys Lys Ile Asp Leu Val Val Lys Gln Cys Glu Gly Gly Pro
    690                 695                 700

Ser Thr Thr Gln Leu Asp Val Met Ser Val Asp
705                 710                 715

<210> SEQ ID NO 16
<211> LENGTH: 705
<212> TYPE: PRT
<213> ORGANISM: Yarrowia lipolytica

<400> SEQUENCE: 16

Met Gly His Tyr Val Thr Leu Ala Thr Cys Asn Leu Asn Gln Trp Ala
1               5                   10                  15

Leu Asp Phe Glu Gly Asn Arg Asp Arg Ile Leu Glu Ser Ile Arg Glu
            20                  25                  30

Ala Lys Arg Gln Gly Ala Ser Leu Arg Val Gly Pro Glu Leu Glu Ile
        35                  40                  45

Thr Gly Tyr Gly Cys Leu Asp His Phe Leu Glu Gly Asp Leu Tyr Leu
    50                  55                  60

His Ser Trp Glu Val Tyr Ala Glu Ile Leu Glu His Pro Asp Thr Ser
65              70                  75                  80

Asp Ile Ile Leu Asp Ile Gly Met Pro Val Met His Lys Asn Val Lys
                85                  90                  95

Tyr Asn Cys Arg Val Ile Ser Tyr Asn Arg Glu Ile Leu Leu Ile Arg
            100                 105                 110

Pro Lys Leu Ser Leu Ala Asn Asp Gly Asn Tyr Arg Glu Met Arg Tyr
        115                 120                 125

Phe Thr Pro Trp Pro Lys Ala Arg Tyr Val Glu Asp Tyr Thr Leu Pro
    130                 135                 140

Arg Phe Val Gln Asn Val Cys Ala Asn Glu Ser Ala Ile Val Pro Phe
145                 150                 155                 160

Gly Asp Cys Val Leu Ser Thr Lys Asp Ala Val Ile Gly Phe Glu Thr
                165                 170                 175

Cys Glu Glu Leu Phe Thr Pro Gln Ser Pro His Ile Gly Met Ser Leu
            180                 185                 190

Asp Gly Val Glu Ile Phe Thr Asn Ser Ser Gly Ser His His Glu Leu
        195                 200                 205

```
Arg Lys Leu Asn Thr Arg Met Glu Leu Ile Arg Glu Ala Thr Ala Lys
    210                 215                 220
Cys Gly Gly Ile Tyr Leu Tyr Ala Asn Gln Arg Gly Cys Asp Gly Asp
225                 230                 235                 240
Arg Leu Tyr Tyr Asp Gly Cys Ala Val Ile Ala Val Asn Gly Glu Val
                245                 250                 255
Val Ala Gln Gly Ser Gln Phe Ser Leu Asp Asp Val Glu Val Val Ser
                260                 265                 270
Ala Thr Leu Asp Leu Glu Ala Val Arg Ser Tyr Arg Ala Ser Lys Ile
            275                 280                 285
Ser Gln Cys Met Gln Ala Ala Asn Ser Pro Cys Tyr Ala Arg Val Thr
    290                 295                 300
Cys Lys Ala Glu Leu Ser Pro Ser Ser Val Thr Phe Asp Ser Glu Val
305                 310                 315                 320
Tyr Pro Thr Pro Thr Arg Glu Ile Arg Tyr His Ser Pro Glu Glu Glu
                325                 330                 335
Ile Ala Leu Gly Pro Ala Cys Trp Met Trp Asp Tyr Val Arg Arg Cys
                340                 345                 350
Arg Ala Ala Gly Phe Phe Val Pro Leu Ser Gly Ile Asp Ser Cys
            355                 360                 365
Ala Thr Ala Thr Ile Val Tyr Ser Met Cys Val Leu Val Ala Asp Ala
    370                 375                 380
Ala Asn Asn Gly Asn Glu Gln Val Ile Lys Asp Ala Arg Val Val Thr
385                 390                 395                 400
Gly Asp Pro Asp Phe Val Pro Thr Asp Pro Lys Glu Leu Cys Asn Arg
                405                 410                 415
Ile Phe His Thr Cys Phe Met Gly Thr Glu Asn Ser Ser Lys Asp Thr
                420                 425                 430
Arg Ser Arg Ala Lys Asp Leu Ala Ala Ala Ile Gly Ala Tyr His Thr
            435                 440                 445
Asp Leu Asn Met Asp Ser Val Val Ser Ala Val Arg Gly Leu Phe Glu
    450                 455                 460
Thr Val Thr Gly Lys Arg Pro Ile Phe Lys Val His Gly Gly Ser Ala
465                 470                 475                 480
Thr Glu Asn Leu Ala Leu Gln Asn Ile Gln Ala Arg Leu Arg Met Val
                485                 490                 495
Leu Ala Tyr Leu Phe Ala Gln Leu Leu Pro Trp Cys Arg Gly Arg Ala
                500                 505                 510
Gly Gly Leu Leu Val Leu Gly Ser Ala Asn Val Asp Glu Thr Leu Arg
            515                 520                 525
Gly Tyr Leu Thr Lys Tyr Asp Cys Ser Ser Ala Asp Ile Asn Pro Ile
    530                 535                 540
Gly Gly Ile Ser Lys Thr Asp Leu Lys Lys Phe Ile Ala Tyr Ala Glu
545                 550                 555                 560
His Lys Phe Asp Leu Pro Ile Leu Asn Asp Phe Leu Thr Ala Val Pro
                565                 570                 575
Thr Ala Glu Leu Glu Pro Ile Thr Lys Asp Tyr Val Gln Ser Asp Glu
                580                 585                 590
Val Asp Met Gly Met Thr Tyr Asp Glu Leu Ser Val Phe Gly Arg Leu
            595                 600                 605
Arg Lys Val Glu Lys Cys Gly Pro Tyr Ser Met Phe Ile Lys Leu Tyr
    610                 615                 620
His Glu Trp Thr Pro Arg Leu Ser Ala Glu Gln Ile Ala Ala Lys Val
```

```
                625                 630                 635                 640
Lys Arg Phe Phe Trp Phe Tyr Ala Val Asn Arg His Lys Thr Thr Val
                    645                 650                 655
Leu Thr Pro Ser Tyr His Ala Glu Gln Tyr Ser Pro Asp Asp Asn Arg
                660                 665                 670
Phe Asp Leu Arg Pro Phe Leu Ile Asn Pro Gly Phe Ser Trp Ala Ser
            675                 680                 685
Lys Lys Ile Asp Ala Ile Val Lys Ser Leu Glu Thr Lys Lys Lys Glu
        690                 695                 700
Asp
705

<210> SEQ ID NO 17
<211> LENGTH: 714
<212> TYPE: PRT
<213> ORGANISM: Candida albicans

<400> SEQUENCE: 17

Met Gly Asn Tyr Ile Thr Val Ala Thr Cys Asn Leu Asn Gln Trp Ala
1               5                   10                  15
Leu Asp Phe Glu Gly Asn Arg Asp Arg Ile Phe Glu Ser Ile Lys Glu
            20                  25                  30
Ala Lys Arg Gln Gly Ala Lys Leu Arg Val Gly Pro Glu Leu Glu Val
        35                  40                  45
Cys Gly Tyr Gly Cys Leu Asp His Phe Ala Glu Asn Asp Leu Tyr Arg
    50                  55                  60
His Ser Trp Glu Val Tyr Gly Glu Ile Leu Ser Asn Pro Glu Thr His
65                  70                  75                  80
Gly Ile Leu Leu Asp Ile Gly Ile Pro Ile Ile His Lys Ser Ile Lys
                85                  90                  95
Tyr Asn Cys Arg Ile Ile Ser Tyr Asn Gly Lys Ile Leu Leu Ile Arg
            100                 105                 110
Pro Lys Ile Tyr Leu Ala Asn Asp Gly Asn Tyr Arg Glu Met Arg Tyr
        115                 120                 125
Phe Thr Gly Trp Asn Arg Pro Lys Tyr His Glu Glu Tyr Gln Leu Pro
    130                 135                 140
Lys Phe Ile Ser Lys Ile Thr Gly Gln Ala Arg Val Pro Phe Gly Asp
145                 150                 155                 160
Cys Ile Val Gln Thr Leu Glu Thr Arg Leu Gly Cys Glu Thr Cys Glu
                165                 170                 175
Glu Leu Phe Thr Pro Glu Ser Pro His Ile Ala Met Ala Leu Asp Gly
            180                 185                 190
Val Glu Ile Phe Thr Asn Ser Ser Gly Ser His His Gly Leu Arg Lys
        195                 200                 205
Leu Asp Thr Arg Leu Lys Leu Ile Thr Glu Ala Thr Lys Lys Cys Gly
    210                 215                 220
Gly Ile Tyr Leu Tyr Ala Asn Gln Lys Gly Cys Asp Gly Asp Arg Leu
225                 230                 235                 240
Tyr Tyr Asp Gly Cys Ala Ser Ile Ile Val Asn Gly Asn Val Leu Ala
                245                 250                 255
Gln Ala Ser Gln Phe Ser Leu Lys Asp Val Glu Val Ile Ser Ala Thr
            260                 265                 270
Val Asp Leu Asp Asp Val Arg Ala Tyr Arg Asn Gln Lys Ser Ala Ser
        275                 280                 285
Val Gln Ala Val Asn Gln Ser Glu Lys Phe Lys Val Ile Tyr Thr Asp
```

-continued

```
            290                 295                 300
Val Glu Leu Ser Pro Ser Asp Tyr Val Phe Asp His Ser Ile Ile Pro
305                 310                 315                 320

Ser Lys Pro Gln Pro Ile Lys Tyr His Thr Pro Glu Glu Ile Ala
                325                 330                 335

Leu Gly Pro Ala Cys Trp Leu Trp Asp Tyr Leu Arg Arg Ser Lys Cys
                340                 345                 350

Gly Gly Tyr Phe Leu Pro Leu Ser Gly Gly Ile Asp Ser Cys Ala Thr
                355                 360                 365

Ala Val Ile Val His Ser Met Cys Arg Leu Val Val Glu Ala Ile Pro
370                 375                 380

Asn Asp Glu Gln Val Leu Lys Asp Ile Gln Ala Ile Thr His Asp Glu
385                 390                 395                 400

Gly Phe Val Pro Lys Thr Pro Gln Asp Ile Ala Gln Arg Ile Phe Tyr
                405                 410                 415

Thr Ser Phe Met Gly Thr Glu Asn Ser Ser Lys Glu Thr Arg Ser Arg
                420                 425                 430

Ser Lys Glu Leu Ala Ser Lys Ile Gly Ser Tyr His Val Asp Leu Asn
                435                 440                 445

Met Asp Asn Leu Val Thr Ser Val Ser Leu Phe Glu Val Ala Thr
450                 455                 460

Gly Lys Lys Pro Ile Phe Lys Ile Phe Gly Ser Asn Thr Glu Asn
465                 470                 475                 480

Leu Ala Leu Gln Asn Ile Gln Ala Arg Leu Arg Met Val Leu Ser Tyr
                485                 490                 495

Leu Phe Ala Gln Leu Leu Pro Trp Thr Arg Gly Lys Asn Val Pro Gly
                500                 505                 510

Leu Leu Val Leu Gly Ser Ala Asn Val Asp Glu Cys Leu Arg Gly Tyr
                515                 520                 525

Leu Thr Lys Tyr Asp Cys Ser Ser Ala Asp Ile Asn Pro Ile Gly Gly
                530                 535                 540

Ile Ser Lys Thr Asp Leu Lys Arg Phe Ile Ala Trp Ala Glu Lys Asn
545                 550                 555                 560

Phe Asp Leu Pro Ile Leu His Glu Phe Leu Thr Ala Thr Pro Thr Ala
                565                 570                 575

Glu Leu Glu Pro Ile Thr Lys Asp Tyr Val Gln Ser Asp Glu Ile Asp
                580                 585                 590

Met Gly Met Thr Tyr Asp Glu Leu Ser Arg Phe Gly Thr Leu Arg Lys
                595                 600                 605

Val Asp Lys Cys Gly Pro Leu Ala Met Phe Ile Lys Leu Tyr His Glu
610                 615                 620

Trp Ser Gln Pro Pro Tyr Asn Leu Ser Ala Lys Gln Ile Ala Glu Lys
625                 630                 635                 640

Val Lys Arg Phe Trp Phe Tyr Ala Ile Asn Arg His Lys Met Thr
                645                 650                 655

Thr Met Thr Pro Ala Tyr His Ala Glu Gln Tyr Ser Pro Asp Asp Asn
                660                 665                 670

Arg Phe Asp Leu Arg Pro Phe Leu Ile Asn Pro Arg Phe Pro His Ala
                675                 680                 685

Ser Lys Lys Ile Asp Glu Leu Val Glu Ile Glu Lys Arg Gln His
                690                 695                 700

Glu Ile Asp Ser Ser Asn Lys Ser Val Asp
705                 710
```

<210> SEQ ID NO 18
<211> LENGTH: 716
<212> TYPE: PRT
<213> ORGANISM: Debaryomyces hansenii

<400> SEQUENCE: 18

```
Met Gly His Tyr Ile Thr Leu Ala Thr Cys Asn Leu Asn Gln Trp Ala
1               5                   10                  15

Leu Asp Phe Glu Gly Asn Arg Asp Arg Ile Ile Thr Ser Ile Ile Glu
            20                  25                  30

Ala Lys Lys Leu Gly Ala Thr Leu Arg Val Gly Pro Glu Leu Glu Ile
        35                  40                  45

Cys Gly Tyr Gly Cys Leu Asp His Phe Leu Glu Asn Asp Leu Tyr Asp
    50                  55                  60

His Ser Trp Glu Met Tyr Gly His Ile Leu Thr Asn Pro Asn Thr Gln
65                  70                  75                  80

Asp Ile Leu Leu Asp Val Gly Met Pro Ile Ile His Lys Ser Ile Lys
                85                  90                  95

Tyr Asn Cys Arg Leu Leu Ser Tyr Asn Gly Lys Ile Leu Leu Ile Arg
            100                 105                 110

Pro Lys Leu Tyr Leu Ala Asn Asp Gly Asn Tyr Arg Glu Met Arg Tyr
        115                 120                 125

Phe Thr Pro Trp Asn Arg Pro Lys Tyr Tyr Glu Ser Phe Gln Leu Pro
    130                 135                 140

Lys Asn Ile Ser Ser Val Thr Gly Gln Ser Asn Val Thr Phe Gly Asp
145                 150                 155                 160

Cys Val Ile Gln Thr Leu Glu Thr Thr Leu Gly Ala Glu Thr Cys Glu
                165                 170                 175

Glu Leu Phe Thr Pro Gln Ser Pro His Ile Ser Met Ala Leu Asp Gly
            180                 185                 190

Val Glu Ile Phe Thr Asn Ser Ser Gly Ser His His Glu Leu Arg Lys
        195                 200                 205

Leu Asp Thr Arg Leu Gln Leu Ile Thr Gly Ala Thr Lys Lys Cys Gly
    210                 215                 220

Gly Val Tyr Leu Tyr Ala Asn Gln Lys Gly Cys Asp Gly Asp Arg Leu
225                 230                 235                 240

Tyr Tyr Asp Gly Cys Ala Cys Ile Ile Val Asn Gly Lys Val Val Ala
                245                 250                 255

Gln Ala Ser Gln Phe Ser Leu Arg Asp Val Glu Val Val Ser Ala Thr
            260                 265                 270

Ile Asp Leu Asp Asp Val Arg Ser Tyr Arg Asn Gln Lys Leu Ser Ala
        275                 280                 285

Phe Gln Ser Val Ser Gln Ser Asp Ser Thr Val Tyr His His Ile Pro
    290                 295                 300

Thr Asp Ile Glu Leu Ser Pro Asn Ser Asn Val Phe Asn Pro Asn Val
305                 310                 315                 320

Lys Pro Ser Pro Tyr Arg Asp Ile Arg Tyr His Leu Pro Glu Glu Glu
                325                 330                 335

Ile Ala Leu Gly Pro Ala Cys Trp Leu Trp Asp Tyr Leu Arg Arg Ser
            340                 345                 350

Lys Cys Ala Gly Tyr Phe Leu Pro Leu Ser Gly Gly Ile Asp Ser Cys
        355                 360                 365

Ala Thr Ala Val Ile Val His Leu Met Cys Arg Leu Val Val Lys Ser
    370                 375                 380
```

```
Cys Glu Glu Gly Asp Lys Gln Val Ile Ser Asp Ile Gln Ser Leu Thr
385                 390                 395                 400

His Asp Pro Glu Phe Val Pro Lys Thr Pro Gln Glu Val Ala Gly Arg
            405                 410                 415

Leu Phe Tyr Thr Ser Phe Met Gly Thr Glu Asn Ser Ser Lys Glu Thr
            420                 425                 430

Arg Ser Arg Ala Lys Glu Leu Ser Glu Lys Val Gly Ser His His Ile
435                 440                 445

Asp Met Asn Met Asp Ser Leu Val Ser Ala Val Ser Val Phe Glu
    450                 455                 460

Val Ala Thr Gly Lys Lys Pro Ile Phe Lys Ile Phe Gly Gly Ser Gln
465                 470                 475                 480

Thr Glu Asn Leu Ala Leu Gln Asn Ile Gln Ala Arg Leu Arg Met Val
            485                 490                 495

Leu Ser Tyr Leu Phe Ala Gln Leu Leu Pro Trp Thr Arg Asn Ile Ser
            500                 505                 510

Gly Gly Leu Leu Val Leu Gly Ser Ala Asn Val Asp Glu Cys Leu Arg
            515                 520                 525

Gly Tyr Leu Thr Lys Tyr Asp Cys Ser Ser Ala Asp Ile Asn Pro Ile
530                 535                 540

Gly Gly Ile Ser Lys Thr Asp Leu Lys Arg Phe Ile Asp Trp Ala Asp
545                 550                 555                 560

Lys Asn Phe Glu Leu Pro Ile Leu His Asp Phe Leu Thr Ala Thr Pro
            565                 570                 575

Thr Ala Glu Leu Glu Pro Ile Thr Gln Asn Tyr Val Gln Ser Asp Glu
            580                 585                 590

Val Asp Met Gly Met Thr Tyr Asp Glu Leu Ser Arg Phe Gly Arg Leu
            595                 600                 605

Arg Lys Val Asp Lys Cys Gly Pro Met Ala Met Phe Ile Lys Leu Tyr
610                 615                 620

His Glu Trp Ser Gln Pro Pro Leu Asn Leu Thr Ala Glu Gln Val Ala
625                 630                 635                 640

Glu Lys Val Lys Arg Phe Trp Phe Phe Tyr Ala Ile Asn Arg His Lys
            645                 650                 655

Met Thr Thr Met Thr Pro Ser Tyr His Ala Glu Gln Tyr Ser Pro Asp
            660                 665                 670

Asp Asn Arg Phe Asp Leu Arg Pro Phe Leu Ile Asn Pro Arg Phe Pro
            675                 680                 685

Trp Ala Ser Lys Lys Ile Asp Glu Ala Val Asp Ile Ile Asn Gln Arg
            690                 695                 700

Thr Glu Glu Ile Lys Arg Ala Asn Leu Ser Val Asp
705                 710                 715

<210> SEQ ID NO 19
<211> LENGTH: 749
<212> TYPE: PRT
<213> ORGANISM: Aspergillus oryzae

<400> SEQUENCE: 19

Met Gly His Leu Val Thr Leu Ala Thr Cys Ser Leu Asn Gln Trp Ala
1               5                   10                  15

Leu Asp Phe Glu Gly Asn Cys Glu Arg Ile Ile Glu Ser Ile Arg Gln
            20                  25                  30

Ala Lys Lys Ala Gly Ala Thr Leu Arg Val Gly Pro Glu Leu Glu Ile
        35                  40                  45
```

```
Thr Gly Tyr Gly Val Leu Asp Gly Phe Leu Glu Gly Asp Thr Phe Leu
     50                  55                  60

His Ser Trp Glu Met Leu Ala Arg Ile Ile Asp His Ala Asp Cys Gln
 65                  70                  75                  80

Asp Ile Val Val Asp Val Gly Met Pro Val Arg His Arg Asn Val Arg
                     85                  90                  95

Tyr Asn Cys Arg Val Ile Phe Tyr Asn Arg Lys Ile Ile Leu Ile Arg
                100                 105                 110

Pro Lys Met Trp Leu Ala Asn Asp Gly Asn Tyr Arg Glu Met Arg Tyr
            115                 120                 125

Phe Thr Pro Trp Gln Arg Pro Gln Glu Ile Glu Asp Tyr Tyr Leu Glu
        130                 135                 140

Ser Ile Val Gly Lys Ile Thr Gly Gln Tyr Lys Val Pro Phe Gly Asp
145                 150                 155                 160

Ala Val Ile Ser Thr Arg Asp Thr Cys Leu Gly Leu Glu Thr Cys Glu
                165                 170                 175

Glu Leu Phe Thr Pro Asn Gly Tyr Ala Leu Gln Leu Arg Asn Cys Asp
            180                 185                 190

Tyr His Ala Asn Ile Tyr Val Gly Leu Ile Phe Leu Met Val Leu Pro
        195                 200                 205

Val Trp Pro Ser Leu Gln Asp Arg Pro Leu Thr Ser Pro Ile Gly Val
    210                 215                 220

Glu Ile Ile Ser Asn Ser Ser Gly Ser His His Glu Leu Arg Lys Leu
225                 230                 235                 240

Asp Thr Arg Ile Asn Leu Val Thr Gln Ala Thr Lys Leu Ser Gly Gly
                245                 250                 255

Ile Tyr Leu Tyr Ala Asn Gln Gln Gly Cys Asp Gly Asp Arg Leu Tyr
            260                 265                 270

Tyr Asp Gly Cys Ala Met Ile Val Val Asn Gly Asn Ile Val Ala Gln
        275                 280                 285

Gly Ser Gln Phe Ser Leu Asn Asp Val Glu Val Thr Ala Thr Val
    290                 295                 300

Asp Ile Glu Glu Val Arg Thr Tyr Arg Ser Ser Ala Ser Arg Gly Met
305                 310                 315                 320

Gln Ala Ser Lys Gln Thr Pro Phe Val Arg Leu Asp Leu Asp Met Arg
                325                 330                 335

Leu Ser Arg Gln Asn Glu Glu Ala Asp Pro Gly Leu Ala Pro Ser Glu
            340                 345                 350

Ala Ile Ala Pro Arg Tyr His Ala Pro Glu Glu Val Ala Leu Gly
        355                 360                 365

Pro Ala Cys Trp Leu Trp Asp Tyr Leu Arg Arg Ser Gly Ala Ala Gly
    370                 375                 380

Phe Phe Leu Pro Leu Ser Gly Gly Ile Asp Ser Cys Ala Thr Ala Ile
385                 390                 395                 400

Ile Val His Ser Met Cys Arg Glu Val Ile Lys Ala Val Ser Glu Gly
                405                 410                 415

Asn Glu Gln Val Ile Lys Asp Val Arg Arg Leu Cys Ala Glu Pro Ala
            420                 425                 430

Asp Ser Thr Trp Leu Pro Thr Thr Ser Gln Glu Val Cys Asn Arg Ile
        435                 440                 445

Phe His Thr Ser Tyr Met Gly Thr Gln Asn Ser Ser Lys Glu Thr Arg
    450                 455                 460

Asp Arg Ser Lys Arg Leu Ser Thr Asp Ile Gly Ser Tyr His Val Asp
465                 470                 475                 480
```

-continued

```
Phe Asn Phe Asp Thr Val Val Thr Ser Leu Thr Asn Leu Phe Thr Met
            485                 490                 495
Val Thr Asn Phe Gln Pro Lys Phe Lys Val His Gly Gly Ser Arg Ala
        500                 505                 510
Glu Asn Gln Ala Leu Gln Asn Val Gln Ala Arg Leu Arg Met Val Leu
            515                 520                 525
Ser Tyr Leu Phe Ala Ser Leu Leu Pro Thr Val Arg Gln Arg Pro Gly
        530                 535                 540
Gly Gly Gly Leu Leu Val Leu Ala Ser Ser Asn Val Asp Ala Glu Cys
545                 550                 555                 560
Leu Arg Gly Tyr Leu Thr Lys Tyr Asp Ala Ser Ser Ala Asp Leu Asn
                565                 570                 575
Pro Ile Gly Ser Ile Ser Lys Val Asp Leu Lys Phe Ile Ala Trp
            580                 585                 590
Ser Arg Asp Ser Phe Glu Leu Pro Ile Leu His Glu Phe Leu Asn Ala
        595                 600                 605
Thr Pro Thr Ala Glu Leu Glu Pro Ile Thr Ser Thr Tyr Val Gln Ser
    610                 615                 620
Asp Glu Ala Asp Met Gly Val Thr Tyr Ala Glu Leu Ser Thr Phe Gly
625                 630                 635                 640
Tyr Leu Arg Lys Ile Ala Lys Leu Gly Pro Trp Ser Met Tyr Glu Arg
                645                 650                 655
Leu Leu His Val Trp Gly Asn Glu Tyr Ser Pro Arg Glu Ile Tyr Glu
            660                 665                 670
Lys Thr Arg His Phe Phe Tyr Asn Tyr Ala Ile Asn Arg His Lys Met
        675                 680                 685
Thr Val Leu Thr Pro Ser Tyr His Ala Glu Gln Tyr Ser Pro Asp Asp
    690                 695                 700
Asn Arg His Asp Leu Arg Gln Phe Leu Tyr Pro Ser Phe Thr Trp Ala
705                 710                 715                 720
Tyr Lys Lys Met Glu Asp Ser Val Lys Tyr Trp Glu Ser Lys Gly Trp
                725                 730                 735
Thr Ala Gly Lys Ala Gln Lys Lys Asn Val Lys Ala Asp
            740                 745
```

<210> SEQ ID NO 20
<211> LENGTH: 767
<212> TYPE: PRT
<213> ORGANISM: Ustilago maydis

<400> SEQUENCE: 20

```
Met Gly Leu Pro Val Thr Val Ser Thr Cys Ser Leu Asn Gln Trp Ala
1               5                   10                  15
Leu Asp Phe Asp Gly Asn Arg Asp Arg Ile Leu Glu Ser Ile Arg Leu
            20                  25                  30
Ala Lys Ser Val Gly Ser Arg Leu Arg Val Gly Pro Glu Leu Glu Ile
        35                  40                  45
Pro Gly Tyr Gly Cys Phe Asp His Phe Leu Glu Pro Asp Thr Val Leu
    50                  55                  60
His Ser Trp Gln Val Leu Ala Glu Ile Leu Ser Ser Asp Ala Thr Asn
65                  70                  75                  80
Gly Ile Leu Cys Asp Val Gly Met Pro Val Leu His Arg Ser Thr Leu
                85                  90                  95
Tyr Asn Cys Arg Val Leu Leu Leu Asp Gly Lys Ile Leu His Ile Arg
            100                 105                 110
```

```
Pro Lys Met Trp Leu Ala Asn Asp Gly Asn Tyr Arg Glu Met Arg Tyr
        115                 120                 125

Phe Ser Pro Trp Thr Arg Thr Asn His Thr Asp Ser Phe Pro Leu Pro
    130                 135                 140

Arg Ile Val Ser Ser Ile Thr Asp Gln His Glu Val Pro Phe Gly Asp
145                 150                 155                 160

Ala Val Val Lys Thr Arg Asp Thr Val Leu Gly Val Glu Leu Cys Glu
                165                 170                 175

Glu Leu Phe Thr Pro Asn Ser Pro His Ile Arg Gln Gly Leu Asp Gly
            180                 185                 190

Val Glu Ile Phe Thr Asn Ser Ser Ala Ser His His Glu Leu Arg Lys
        195                 200                 205

Leu Tyr Arg Arg Val Glu Leu Ile Lys Glu Ala Thr Leu Lys Leu Gly
    210                 215                 220

Gly Ile Tyr Leu Tyr Ala Asn Gln Gln Gly Cys Asp Gly Asp Arg Leu
225                 230                 235                 240

Tyr Tyr Asp Gly Cys Pro Leu Ile Ala Val Asn Gly Ser Ile Val Ala
                245                 250                 255

Gln Gly Ser Gln Phe Ser Leu Asp Asp Val Gln Val Val Ser Ala Thr
            260                 265                 270

Val Asp Leu Asp Asp Val Arg Ala His Arg Ser Ala Lys Ser Arg Gly
        275                 280                 285

Met Gln Ala Val Ser His Ser Leu Gly Ser Gly Tyr Pro Arg Ile His
    290                 295                 300

Val Asp Phe Glu Val Gly Glu Ser Glu Glu Tyr Ser Ser Lys Thr Pro
305                 310                 315                 320

Gly Thr Ser Thr Pro Val Ala Val Gly Ser Ala Val Ala Pro Val Asp
                325                 330                 335

Gly Gln Arg Asp Asp Ala Glu Arg Leu Tyr Lys Arg Tyr Leu Thr Pro
            340                 345                 350

Leu Ser Gln Pro Ile Glu Val His Tyr His Ser Pro Glu Gln Glu Ile
        355                 360                 365

Ala Leu Gly Pro Ala Cys Trp Leu Trp Asp Tyr Leu Arg Arg Ser Arg
    370                 375                 380

Thr Gln Gly Tyr Phe Val Pro Leu Ser Gly Gly Ile Asp Ser Cys Ala
385                 390                 395                 400

Thr Ala Thr Ile Val Phe Ser Met Cys Arg Leu Val Ile Ala Ala Ile
                405                 410                 415

Asp Ala Pro Ser Ser Ser Pro Ala Ser Lys Ala Thr Ser Ser Leu
            420                 425                 430

Thr Thr Asp Thr Arg Thr Gln Val Leu Gln Asp Val Arg Ile Cys
        435                 440                 445

Asn Glu Lys Pro Ser Ser Thr Trp Ile Pro Ala Ser Pro Gln Glu Leu
    450                 455                 460

Cys Asn Arg Ile Phe Val Thr Cys Tyr Met Gly Thr Glu Asn Ser Ser
465                 470                 475                 480

Ala Glu Thr Arg Gln Arg Ala Lys Asp Leu Ala Ala Asp Ile Gly Ala
                485                 490                 495

Tyr His Ile Asp Leu Asn Met Asp Ile Val Val Arg Ala Ile Ile Ala
            500                 505                 510

Leu Phe Ser Thr Val Thr Gly Ser Thr Pro Arg Phe Arg Val His Gly
        515                 520                 525

Gly Thr Pro Ala Glu Asn Leu Ala Leu Gln Asn Ile Gln Ala Arg Leu
```

-continued

```
               530                 535                 540
Arg Met Leu Leu Ala Tyr Met Phe Ala Gln Leu Thr Pro Trp Val Arg
545                 550                 555                 560

Gly Ser Trp Gly Gly Leu Leu Val Leu Gly Ser Ala Asn Val Asp Glu
                565                 570                 575

Ser Leu Arg Gly Tyr Leu Thr Lys Tyr Asp Cys Ser Ser Ala Asp Ile
                580                 585                 590

Asn Pro Ile Gly Gly Ile Ser Lys Thr Asp Leu Lys Ala Phe Ile Ala
                595                 600                 605

Tyr Ala Arg Asp Ala Phe Ser Leu Pro Ile Leu His Ser Phe Leu Thr
610                 615                 620

Ala Val Pro Thr Ala Glu Leu Glu Pro Ile Thr Gly Ser Tyr Val Gln
625                 630                 635                 640

Ala Asp Glu Ala Asp Met Gly Met Thr Tyr Asp Glu Leu Ser Val Phe
                645                 650                 655

Gly Arg Leu Arg Lys Asn Leu Lys Cys Gly Pro Tyr Ser Met Phe Asn
                660                 665                 670

Lys Leu Leu Gln Gln Trp Gly Pro Thr Met Gly Pro Glu Arg Val Ala
                675                 680                 685

Glu Lys Val Lys Leu Phe Trp Phe Glu Tyr Ala Arg Asn Arg His Lys
690                 695                 700

Met Thr Thr Leu Thr Pro Ser Tyr His Ala Glu Ser Tyr Ser Pro Asp
705                 710                 715                 720

Asp Asn Arg Phe Asp Leu Arg Pro Phe Leu Tyr Pro Ser Arg Phe Pro
                725                 730                 735

Phe Gln Phe Arg Lys Ile Asp Glu Leu Val Lys Arg Leu Gln Ala Phe
                740                 745                 750

Gln Ala Ile Pro Pro Pro Ser Arg Asp Glu Asn Arg Lys Gln Val
                755                 760                 765
```

<210> SEQ ID NO 21
<211> LENGTH: 706
<212> TYPE: PRT
<213> ORGANISM: Cryptococcus neoformans

<400> SEQUENCE: 21

```
Met His Leu Val Thr Val Ala Thr Cys Gln Leu Arg Gln Trp Ser Leu
1               5                   10                  15

Asp Phe Glu Gly Asn Cys Glu Arg Ile Leu Arg Ser Ile Ala Ile Ala
                20                  25                  30

Lys Ser Arg Gly Ala Thr Leu Arg Val Gly Pro Glu Leu Glu Val Pro
            35                  40                  45

Gly Tyr Gly Cys Asp Thr Met Leu His Ser Trp Glu Val Leu Ala Lys
        50                  55                  60

Ile Leu Gln Ser Glu Glu Ala Lys Gly Ile Val Cys Asp Ile Gly Met
65              70                  75                  80

Pro Leu Glu His Lys Asn Asn Tyr Asn Cys Arg Val Ile Phe
                85                  90                  95

Asn Gly Lys Ile Leu Leu Ile Arg Pro Lys Met Trp Met Ala Asn Asp
                100                 105                 110

Gly Asn Tyr Arg Glu Leu Arg His Phe Thr Pro Trp His Lys His Arg
            115                 120                 125

Gln Val Glu Lys His Ser Leu Pro His Met Ile Arg Ile Val Thr Gly
        130                 135                 140

Gln Thr Tyr Val Pro Phe Gly Asp Ala Val Ile Ala Thr Glu Asp Thr
```

```
                145                 150                 155                 160
Val Ile Gly Val Glu Leu Cys Glu Glu Leu Phe Thr Pro Ala Ser Pro
                    165                 170                 175

His Ile Leu Met Gly Leu Asp Gly Val Glu Ile Phe Thr Asn Ser Ser
            180                 185                 190

Gly Ser His His Glu Leu Arg Lys Leu Asn Arg Arg Val Glu Leu Ile
        195                 200                 205

Lys Glu Ala Thr Met Lys Leu Gly Gly Ile Tyr Leu Tyr Ala Asn Gln
        210                 215                 220

Gln Gly Cys Asp Gly Asp Arg Leu Tyr Tyr Asp Gly Ala Cys Leu Ile
225                 230                 235                 240

Ala Met Asn Gly Gln Ile Leu Ala Gln Gly Pro Gln Phe Ser Leu Ser
                245                 250                 255

Glu Val Glu Val Val Ser Ala Thr Val Asp Leu Arg Ala Val Arg Ala
                260                 265                 270

His Arg Thr Thr Ser Ser Arg Arg Met Gln Ser Ala Gln Ala Glu Ala
            275                 280                 285

Tyr Glu Arg Val Val Ala Asp Thr Arg Leu Asp Gly Gly Glu Gln Ile
        290                 295                 300

Lys Val Gly Leu Arg Glu Thr Lys Gly Ser Met Asp Val Arg Tyr His
305                 310                 315                 320

Thr Pro Glu Glu Glu Ile Ala Leu Gly Pro Ala Cys Trp Leu Trp Asp
                325                 330                 335

Tyr Leu Arg Arg Ser Arg Thr Gln Gly Tyr Phe Leu Pro Leu Ser Gly
                340                 345                 350

Gly Ile Asp Ser Cys Ala Thr Ala Ile Ile Val His Ser Met Cys Arg
            355                 360                 365

Leu Val Val Glu Ala Ala Ala Lys Gly Asp Glu Gln Val Ile Thr Asp
        370                 375                 380

Ala Arg Arg Ile Thr Asn Glu Pro Glu Asp Ser Thr Tyr Ile Pro Glu
385                 390                 395                 400

Asp Pro Arg Glu Phe Ala Gly Arg Ile Phe His Thr Cys Tyr Met Gly
                405                 410                 415

Thr Glu Asn Ser Ser Ser Glu Thr Arg Glu Arg Ala Lys Asn Leu Ala
                420                 425                 430

Asp Ala Ile Gly Ala Tyr His Val Asp Leu Asn Met Asp Thr Ala Val
            435                 440                 445

Ser Ala Val Lys Gly Ile Phe Ser Phe Val Thr Gly Lys Thr Pro Gln
        450                 455                 460

Phe Lys Ala His Gly Gly Thr Asn Ala Glu Asn Leu Ala Leu Gln Asn
465                 470                 475                 480

Ile Gln Ala Arg Leu Arg Met Val Val Ser Tyr Met Phe Ala Gln Leu
                485                 490                 495

Leu Pro Trp Val Arg Gly Lys Asn Gly Gly Leu Leu Val Leu Gly Ser
                500                 505                 510

Ala Asn Val Asp Glu Ser Leu Arg Gly Tyr Phe Thr Lys Tyr Asp Cys
            515                 520                 525

Ser Ser Ala Asp Val Asn Pro Ile Gly Gly Ile Ser Lys Val Asp Leu
        530                 535                 540

Lys Arg Phe Ile Ala Trp Ala Gln Val Lys Phe Asp Leu Pro Ile Leu
545                 550                 555                 560

Tyr Asn Phe Leu His Ala Val Pro Thr Ala Glu Leu Ile Pro Ile Gly
                565                 570                 575
```

```
Pro Asp Asn Ile Ile Gln Ser Asp Glu Ile Glu Met Gly Met Thr Tyr
            580                 585                 590

Asp Glu Leu Ser Val Tyr Gly Arg Leu Arg Lys Val Glu Lys Cys Gly
        595                 600                 605

Pro Phe Ser Met Phe Gly Lys Leu Val Gln Glu Trp Gly Ser Phe Leu
    610                 615                 620

Ser Pro Lys Glu Ile Ala Glu Lys Val Lys His Phe Phe Met Tyr
625                 630                 635                 640

Ala Ile Asn Arg His Lys Met Thr Thr Ile Thr Pro Ser Val His Met
                645                 650                 655

Glu Ser Tyr Ser Pro Asp Asp Asn Arg Phe Asp Leu Arg Pro Phe Leu
            660                 665                 670

Tyr Pro Ser Gln Phe Thr His Gln Phe Arg Lys Ile Asp Glu Leu Ala
        675                 680                 685

Gly Lys Leu Pro Asp Met Ala Gln Lys Pro Lys Val Asp Thr Asn Glu
    690                 695                 700

Val Asp
705

<210> SEQ ID NO 22
<211> LENGTH: 700
<212> TYPE: PRT
<213> ORGANISM: Schizosaccharomyces pombe

<400> SEQUENCE: 22

Met Glu Arg Tyr Val Thr Ile Ala Ser Cys Gln Leu Asn Gln Trp Ala
1               5                   10                  15

Met Asp Phe Glu Gly Asn Arg Leu Arg Ile Ile Asp Ser Ile Lys Glu
            20                  25                  30

Ala Lys Arg Gln Asn Ala Ser Leu Arg Val Gly Pro Glu Leu Glu Val
        35                  40                  45

Thr Gly Tyr Gly Cys Glu Asp His Phe Leu Glu Ser Asp Thr Tyr Tyr
    50                  55                  60

His Ser Trp Glu Met Leu Cys Ser Ile Ile His Asp Pro Asp Cys Gln
65                  70                  75                  80

Asp Ile Leu Leu Asp Ile Gly Met Pro Val Met His Lys Ala Met Arg
                85                  90                  95

His Asn Cys Arg Ile Leu Ala Leu Asn Gly Lys Ile Leu Leu Ile Arg
            100                 105                 110

Pro Lys Ile Trp Leu Cys Asp Asp Gly Asn Phe Arg Glu Ser Arg Trp
        115                 120                 125

Phe Thr Pro Trp Leu Arg Pro Arg Val Val Glu Thr His Tyr Leu Pro
    130                 135                 140

Thr Phe Val Ala Lys Ser Leu Asn Gln Thr Thr Val Pro Ile Gly Asp
145                 150                 155                 160

Ala Ile Leu Gln Cys Asn Glu Thr Val Val Gly Val Glu Thr Cys Glu
                165                 170                 175

Glu Leu Phe Thr Pro Asn Ser Pro His Ile Asp Met Ala Leu Asp Gly
            180                 185                 190

Val Glu Ile Phe Ile Asn Ala Ser Gly Ser His His Glu Leu Arg Lys
        195                 200                 205

Leu Thr Thr Arg Val Asn Leu Ile Gln Asn Ala Thr Glu Lys Cys Gly
    210                 215                 220

Gly Ile Tyr Leu Tyr Ser Asn Gln Arg Gly Cys Asp Gly Gly Arg Leu
225                 230                 235                 240
```

-continued

Tyr Tyr Asp Gly Ser Ser Met Ile Phe Ala Asn Gly Lys Met Leu Ala
            245                 250                 255

Gln Gly His Gln Phe Ser Leu Lys Asp Val Glu Val Ile Ser Ala Thr
            260                 265                 270

Val Asp Val Asp Thr Val Arg Ser Tyr Arg Phe Gln Pro Ser His Gly
            275                 280                 285

Ile Gln Gly Val Thr Arg Pro Ser Tyr Glu Arg Ile His Val Asn Phe
            290                 295                 300

Ser Leu Ser Ser Tyr Gln Gln Asp Tyr Asp Ile Tyr Arg Lys Pro Thr
305                 310                 315                 320

Asp Pro Ile Glu Val Thr Ile Pro Leu Pro Glu Glu Ile Thr Phe
            325                 330                 335

Gly Pro Ala Cys Trp Leu Trp Asp Tyr Leu Arg Arg Ser His Ala Ala
            340                 345                 350

Gly Phe Phe Leu Pro Leu Ser Gly Gly Leu Asp Ser Cys Ser Thr Ala
            355                 360                 365

Val Leu Val Tyr Ser Met Cys Arg Ile Val Cys Lys Ala Met Glu Glu
            370                 375                 380

Asp Asp Ala Gln Val Leu Ser Asp Val Arg Arg Ile Val Gly Asp Pro
385                 390                 395                 400

Ser Tyr Ser Ser Thr Asp Pro Lys Lys Leu Leu Asn His Leu Phe Tyr
            405                 410                 415

Thr Ala Phe Met Gly Ser Glu His Ser Ser Lys Glu Thr Arg Ser Arg
            420                 425                 430

Ala Lys Glu Leu Ser Ser Leu Ile Gly Ser Tyr His Thr Asp Val Asn
            435                 440                 445

Ile Asp Thr Met Thr Ser Ala Val Val Lys Leu Phe Ala Leu Val Thr
450                 455                 460

Gly Lys Thr Pro Gln Phe Arg Ser Asn Gly Gly Thr Asn Ala Glu Asn
465                 470                 475                 480

Leu Ala Leu Gln Asn Ile Gln Ala Arg Ser Arg Met Leu Leu Gly Tyr
            485                 490                 495

Leu Phe Ala Gln Leu Leu Pro Trp Val Arg Gly Tyr Ser Gly Ser Leu
            500                 505                 510

Leu Val Leu Gly Ser Ser Asn Val Asp Glu Cys Leu Arg Gly Tyr Leu
            515                 520                 525

Thr Lys Tyr Asp Cys Ser Ser Ala Asp Ile Asn Pro Ile Gly Gly Ile
            530                 535                 540

Ser Lys Thr Asp Leu Lys Ser Phe Leu Arg Tyr Ala Lys Glu Ala Leu
545                 550                 555                 560

Asp Leu Pro Ile Leu Gln Glu Phe Leu Asp Ala Thr Pro Thr Ala Glu
            565                 570                 575

Leu Glu Pro Thr Thr Glu Ser Tyr Val Gln Ser Asp Glu Ala Asp Met
            580                 585                 590

Gly Met Thr Tyr Ala Glu Leu Ser Val Phe Gly Arg Leu Arg Lys Ile
            595                 600                 605

Ser Lys Cys Gly Pro Tyr Ser Met Phe Thr Gln Leu Met His Gln Trp
            610                 615                 620

Gly Asp Arg Leu Ser Pro Ser Gln Val Ala Glu Lys Val Lys Arg Phe
625                 630                 635                 640

Phe His Tyr Tyr Gly Ile Asn Arg His Lys Met Thr Thr Leu Thr Pro
            645                 650                 655

Ser Tyr His Ala Glu Thr Tyr Gly Val Asp Asp Asn Arg Tyr Asp Leu
            660                 665                 670

```
Arg Gln Phe Leu Tyr Pro Ser Trp Thr Trp Gln Asn Lys Lys Ile Asp
            675                 680                 685

Ala Leu Ala Ser Lys Phe Glu Gln His Gln Arg Lys
690                 695                 700

<210> SEQ ID NO 23
<211> LENGTH: 678
<212> TYPE: PRT
<213> ORGANISM: Aspergillus nidulans

<400> SEQUENCE: 23

Met Gly Arg Leu Ile Thr Leu Ala Thr Cys Ser Leu Asn Gln Trp Ala
1               5                   10                  15

Leu Asp Trp Glu Gly Asn Cys Glu Arg Ile Ile Glu Ser Ile Arg Gln
            20                  25                  30

Ala Lys Ala Ala Gly Ala Thr Leu Arg Val Gly Pro Glu Leu Glu Ile
        35                  40                  45

Thr Gly Tyr Gly Val Leu Asp Gly Phe Leu Glu Gly Asp Thr Phe Leu
    50                  55                  60

His Ser Trp Glu Met Leu Ala Arg Ile Ile Asp His Pro Asp Cys Gln
65                  70                  75                  80

Asp Ile Val Val Asp Val Asp Gly Asn Tyr Arg Glu Met Arg His Phe
                85                  90                  95

Thr Pro Trp Gln Arg Pro Arg Glu Val Glu Asp Tyr Tyr Leu Glu Gln
            100                 105                 110

Ile Val Gly Lys Ile Thr Gly Gln Tyr Lys Val Pro Phe Gly Asp Ala
        115                 120                 125

Val Ile Ser Thr Arg Asp Thr Cys Leu Gly Leu Glu Thr Cys Glu Glu
130                 135                 140

Leu Phe Thr Pro Asn Gly Pro His Ile Pro Tyr Ser Leu Ala Gly Val
145                 150                 155                 160

Glu Ile Ile Ser Asn Ser Ser Gly Ser His His Glu Leu Lys Lys Leu
                165                 170                 175

Asp Thr Arg Val Asn Leu Ile Thr Gln Ala Thr Lys Leu Ser Gly Gly
            180                 185                 190

Ile Tyr Leu Tyr Ala Asn Gln Gln Gly Cys Asp Gly Asp Arg Leu Tyr
        195                 200                 205

Tyr Asp Gly Cys Ala Met Ile Val Ile Asn Gly Asn Ile Val Ala Gln
    210                 215                 220

Gly Ser Gln Phe Ser Leu Asn Asp Val Glu Val Thr Ala Thr Val
225                 230                 235                 240

Asp Ile Glu Glu Val Arg Thr Tyr Arg Ala Ser Thr Ser Arg Asn Met
                245                 250                 255

Gln Ala Ser Arg Gln Pro Pro Phe Val Arg Leu Asp Leu Asp Thr Arg
            260                 265                 270

Leu Ser Arg Ser Asp Glu Asp Ala Asp Pro Gly Ile Ala Pro Ser Glu
        275                 280                 285

Thr Leu Ile Pro Arg Tyr His Ala Pro Glu Glu Ile Ala Leu Gly
    290                 295                 300

Pro Ala Cys Trp Leu Trp Asp Tyr Leu Arg Arg Ser Gly Ala Ala Gly
305                 310                 315                 320

Phe Phe Leu Pro Leu Ser Gly Gly Ile Asp Ser Cys Ala Thr Ala Val
                325                 330                 335

Ile Val His Ser Met Cys Arg Glu Val Ile Lys Ala Val Gln Gln Gly
            340                 345                 350
```

Asn Glu Gln Val Ile Lys Asp Val Arg Arg Leu Cys Ala Glu Pro Ala
            355                 360                 365

Gly Ser Thr Trp Leu Pro Thr Thr Ser Gln Glu Val Cys Asn Phe Met
        370                 375                 380

Gly Thr Gln Asn Ser Ser Lys Glu Thr Arg Asp Arg Ala Lys Glu Leu
385                 390                 395                 400

Ala Ala Glu Ile Gly Ser Tyr His Ile Asp Phe Asn Phe Asp Thr Val
                405                 410                 415

Val Thr Ala Leu Met Asn Leu Phe Thr Val Thr Asn Phe Gln Pro
            420                 425                 430

Arg Phe Lys Val His Gly Gly Ser Arg Ala Glu Asn Gln Ala Leu Gln
            435                 440                 445

Asn Ile Gln Ala Arg Leu Arg Met Val Leu Ser Tyr Leu Phe Ala Ser
            450                 455                 460

Leu Leu Pro Thr Val Arg Gln Arg Pro Gly Gly Gly Leu Leu Val
465                 470                 475                 480

Leu Ala Ser Ser Asn Val Asp Glu Cys Leu Arg Gly Tyr Leu Thr Lys
                485                 490                 495

Tyr Asp Ala Ser Ser Ala Asp Leu Asn Pro Ile Gly Ser Ile Ser Lys
            500                 505                 510

Val Asp Leu Lys Lys Phe Ile Gly His Cys Ala Thr Ser Phe Asp Met
            515                 520                 525

Pro Ile Leu Thr Ser Phe Leu Asn Ala Thr Pro Thr Ala Glu Leu Glu
            530                 535                 540

Pro Ile Thr Ala Thr Tyr Val Gln Ser Asp Glu Ala Asp Met Gly Val
545                 550                 555                 560

Thr Tyr Ala Glu Leu Gly Thr Phe Gly Tyr Leu Arg Lys Val Ser Lys
                565                 570                 575

Leu Gly Pro Trp Ser Met Tyr Glu Arg Leu Leu His Met Trp Gly Asn
            580                 585                 590

Glu Tyr Ser Pro Arg Glu Ile Tyr Glu Lys Thr Arg His Phe Phe Tyr
            595                 600                 605

Asn Tyr Ala Ile Asn Arg His Lys Met Thr Val Ile Thr Pro Ser Tyr
            610                 615                 620

His Ala Glu Gln Tyr Ser Pro Asp Asp Asn Arg His Asp Leu Arg Gln
625                 630                 635                 640

Phe Leu Tyr Pro Pro Phe Thr Trp Ala Tyr Lys Lys Met Glu Glu Ser
                645                 650                 655

Val Lys Tyr Trp Glu Glu Arg Gly Trp Thr Thr Gly Lys Ala Gln Lys
            660                 665                 670

Lys Ser Val Lys Ala Asp
            675

<210> SEQ ID NO 24
<211> LENGTH: 729
<212> TYPE: PRT
<213> ORGANISM: Neurospora crassa

<400> SEQUENCE: 24

Met Gly Gly His Leu Val Thr Val Ala Thr Cys Ser Leu Asn Gln Trp
1               5                   10                  15

Val Leu Asp Trp Glu Gly Asn Leu Gln Arg Ile Val Glu Ser Ile His
            20                  25                  30

Leu Ala Lys Lys Ala Gly Ala Arg Leu Arg Val Gly Pro Glu Leu Glu
        35                  40                  45

```
Ile Cys Gly Tyr Ser Ser Leu Asp His Phe His Glu Leu Asp Val Tyr
 50                  55                  60

Thr His Ser Leu Glu Met Leu Arg Lys Leu Leu Glu Asp Glu Ser Cys
 65                  70                  75                  80

His Asp Ile Leu Ile Asp Val Gly Leu Pro Ile Leu His Arg Asn Ile
                 85                  90                  95

Arg Tyr Asn Ala Arg Ala Ile Leu Leu Asn Gly Lys Ile Leu Leu Ile
            100                 105                 110

Arg Pro Lys Met Trp Leu Ala Asn Asp Gly Asn Tyr Arg Glu Met Arg
        115                 120                 125

His Phe Thr Pro Trp Met Arg Pro Arg Glu Thr Glu Leu Phe His Leu
    130                 135                 140

Pro Lys Ile Leu Gln Glu Ile Gln Gly Glu Thr His Val Leu Phe Gly
145                 150                 155                 160

Asp Ala Val Ile Ser Thr Pro Glu Thr Ala Phe Gly Ala Glu Thr Cys
                165                 170                 175

Glu Glu Leu Phe Thr Pro Lys Ala Pro His Ile Asp Met Ala Leu Asp
            180                 185                 190

Gly Val Glu Ile Ile Thr Asn Ser Gly Ser His Phe Thr Leu Gln
        195                 200                 205

Lys Leu Asp Val Arg Leu Gln Leu Ile Met Glu Ala Thr Arg Lys Ser
210                 215                 220

Gly Gly Val Tyr Leu Tyr Ala Asn Gln Gln Gly Cys Asp Gly Glu Arg
225                 230                 235                 240

Leu Tyr Phe Asp Gly Cys Ala Met Ile Ile Val Asn Gly Asn Ile Val
                245                 250                 255

Ala Gln Gly Ser Gln Phe Ser Leu Asn Asp Val Glu Val Thr Ala
            260                 265                 270

Thr Val Asp Leu Glu Glu Val Arg Ala Tyr Arg Ser Ser Ile Ser Arg
        275                 280                 285

Gly Leu Gln Ala Ala Thr Ser Asn Ala Lys Tyr Gln Arg Ile Gln Thr
    290                 295                 300

Ser Phe Glu Leu Ser Pro Glu Asp Glu Asp Thr Asp Ile Trp Lys Lys
305                 310                 315                 320

Pro Thr Leu Pro Arg Pro Pro Arg Tyr His Ser Val Glu Glu Ile
                325                 330                 335

Ala Leu Cys Gly Gly Cys Tyr Leu Trp Asp Tyr Leu Arg Arg Ser Gly
            340                 345                 350

Thr Ala Gly Tyr Leu Val Pro Leu Ser Gly Gly Ile Asp Ser Cys Ala
        355                 360                 365

Thr Ala Thr Leu Val Phe Ser Met Cys Arg Ile Val Ile Gln Ala Ile
    370                 375                 380

Glu Asp Gly Asn Gln Gln Val Ile Asp Asp Val Arg Cys Ile Cys Lys
385                 390                 395                 400

Tyr Gly Lys Glu Gly Glu Leu Pro Lys Thr Pro Gln Glu Leu Cys Asn
                405                 410                 415

Gln Val Phe Thr Thr Ile Tyr Met Gly Met Ser Lys Gln Ser Ser Ala
            420                 425                 430

Glu Thr Arg Gly Arg Ala Lys Glu Leu Ser Asp Ala Ile Gly Ser Tyr
        435                 440                 445

His Val Asn Leu Asp Ile Asp Asp Val Tyr Glu Ala Gln Lys Lys Leu
    450                 455                 460

Ile Val Gln Thr Thr Asn Phe Glu Pro Arg Phe Lys Val His Gly Gly
```

```
                465                 470                 475                 480
Thr Val Gln Glu Asn Leu Thr Leu Gln Cys Leu Gln Ala Arg Ile Arg
                    485                 490                 495

Met Val Thr Ala Tyr Glu Phe Gly Gln Ile Leu Pro Thr Ala Arg Gly
                500                 505                 510

Arg Pro Gly Gly Gly Ser Leu Leu Val Leu Gly Ser Ala Asn Val Gly
            515                 520                 525

Glu Ser Leu Arg Gly Tyr Leu Thr Lys Tyr Asp Cys Ser Ser Ala Asp
        530                 535                 540

Ile Asn Pro Ile Gly Ser Ile Asp Lys Ala Asp Leu Lys Arg Phe Ile
545                 550                 555                 560

Ala Trp Ala Glu Lys Lys Phe Asp Leu Pro Cys Leu His Gly Phe Leu
                565                 570                 575

Thr Ala Val Pro Thr Ala Glu Leu Glu Pro Ile Thr Gln Glu Tyr Val
                580                 585                 590

Gln Ser Asp Glu Ala Asp Met Gly Met Thr Tyr Ala Glu Leu Thr Val
            595                 600                 605

Phe Gly Arg Leu Arg Lys Leu Asn Lys Leu Gly Pro Tyr Ala Met Phe
        610                 615                 620

Gln Arg Leu Val His Asp Trp Ser Ala Asp Arg Glu Lys Val Glu Gly
625                 630                 635                 640

Asp Glu Ala Pro Phe Tyr Thr Pro Arg Gln Val Ala Glu Lys Val Lys
                645                 650                 655

Arg Phe Phe His Phe Tyr Ala Ile Asn Arg His Lys Met Thr Thr Leu
                660                 665                 670

Thr Pro Ala Leu His Cys Asn Asp Tyr Ser Pro Asp Asp Asn Arg Phe
                675                 680                 685

Asp Leu Arg Pro Phe Leu Tyr Pro Pro Phe Trp Lys Ser Trp Ser Phe
            690                 695                 700

Lys Arg Ile Asp Met Glu Leu Glu Arg Ile Glu Lys Lys Arg Glu Glu
705                 710                 715                 720

Arg Ala Gly Lys Gly Lys Glu Thr Ala
                    725

<210> SEQ ID NO 25
<211> LENGTH: 652
<212> TYPE: PRT
<213> ORGANISM: Cryptococcus neoformans

<400> SEQUENCE: 25

Met Leu His Ser Trp Glu Val Leu Ala Lys Ile Leu Gln Ser Glu Glu
1               5                   10                  15

Ala Lys Gly Ile Val Cys Asp Ile Gly Met Pro Leu Glu His Lys Asn
                20                  25                  30

Asn Asn Tyr Asn Cys Arg Val Ile Ile Phe Asn Gly Lys Ile Leu Leu
            35                  40                  45

Ile Arg Pro Lys Met Trp Met Ala Asn Asp Gly Asn Tyr Arg Glu Leu
        50                  55                  60

Arg His Phe Thr Pro Trp His Lys His Arg Gln Val Glu Lys His Ser
65                  70                  75                  80

Leu Pro His Met Ile Arg Ile Val Thr Gly Gln Thr Tyr Val Pro Phe
                85                  90                  95

Gly Asp Ala Val Ile Ala Thr Glu Asp Thr Val Ile Gly Val Glu Leu
                100                 105                 110

Cys Glu Glu Leu Phe Thr Pro Ala Ser Pro His Ile Leu Met Gly Leu
```

```
                        115                 120                 125
Asp Gly Val Glu Ile Phe Thr Asn Ser Ser Gly Ser His His Glu Leu
    130                 135                 140
Arg Lys Leu Asn Arg Arg Val Glu Leu Ile Lys Glu Ala Thr Met Lys
145                 150                 155                 160
Leu Gly Gly Ile Tyr Leu Tyr Ala Asn Gln Gln Gly Cys Asp Gly Asp
                165                 170                 175
Arg Leu Tyr Tyr Asp Gly Ala Cys Leu Ile Ala Met Asn Gly Gln Ile
            180                 185                 190
Leu Ala Gln Gly Pro Gln Phe Ser Leu Ser Glu Val Glu Val Val Ser
        195                 200                 205
Ala Thr Val Asp Leu Arg Ala Val Arg Ala His Arg Thr Thr Ser Ser
    210                 215                 220
Arg Arg Met Gln Ser Ala Gln Ala Glu Ala Tyr Glu Arg Val Val Ala
225                 230                 235                 240
Asp Thr Arg Leu Asp Gly Gly Glu Gln Ile Lys Val Gly Leu Arg Glu
                245                 250                 255
Thr Lys Gly Ser Met Asp Val Arg Tyr His Thr Pro Glu Glu Glu Ile
            260                 265                 270
Ala Leu Gly Pro Ala Cys Trp Leu Trp Asp Tyr Leu Arg Arg Ser Arg
        275                 280                 285
Thr Gln Gly Tyr Phe Leu Pro Leu Ser Gly Gly Ile Asp Ser Cys Ala
    290                 295                 300
Thr Ala Ile Ile Val His Ser Met Cys Arg Leu Val Val Glu Ala Ala
305                 310                 315                 320
Ala Lys Gly Asp Glu Gln Val Ile Thr Asp Ala Arg Arg Ile Thr Asn
                325                 330                 335
Glu Pro Glu Asp Ser Thr Tyr Ile Pro Glu Asp Pro Arg Glu Phe Ala
            340                 345                 350
Gly Arg Ile Phe His Thr Cys Tyr Met Gly Thr Glu Asn Ser Ser Ser
        355                 360                 365
Glu Thr Arg Glu Arg Ala Lys Asn Leu Ala Asp Ala Ile Gly Ala Tyr
    370                 375                 380
His Val Asp Leu Asn Met Asp Thr Ala Val Ser Ala Val Lys Gly Ile
385                 390                 395                 400
Phe Ser Phe Val Thr Gly Lys Thr Pro Gln Phe Lys Ala His Gly Gly
                405                 410                 415
Thr Asn Ala Glu Asn Leu Ala Leu Gln Asn Ile Gln Ala Arg Leu Arg
            420                 425                 430
Met Val Val Ser Tyr Met Phe Ala Gln Leu Leu Pro Trp Val Arg Gly
        435                 440                 445
Lys Asn Gly Gly Leu Leu Val Leu Gly Ser Ala Asn Val Asp Glu Ser
    450                 455                 460
Leu Arg Gly Tyr Phe Thr Lys Tyr Asp Cys Ser Ser Ala Asp Val Asn
465                 470                 475                 480
Pro Ile Gly Gly Ile Ser Lys Val Asp Leu Lys Arg Phe Ile Ala Trp
                485                 490                 495
Ala Gln Val Lys Phe Asp Leu Pro Ile Leu Tyr Asn Phe Leu His Ala
            500                 505                 510
Val Pro Thr Ala Glu Leu Ile Pro Ile Gly Pro Asp Asn Ile Ile Gln
        515                 520                 525
Ser Asp Glu Ile Glu Met Gly Met Thr Tyr Asp Glu Leu Ser Val Tyr
    530                 535                 540
```

```
Gly Arg Leu Arg Lys Val Glu Lys Cys Gly Pro Phe Ser Met Phe Gly
545                 550                 555                 560

Lys Leu Val Gln Glu Trp Gly Ser Phe Leu Ser Pro Lys Glu Ile Ala
            565                 570                 575

Glu Lys Val Lys His Phe Phe Met Tyr Ala Ile Asn Arg His Lys
            580                 585                 590

Met Thr Thr Ile Thr Pro Ser Val His Met Glu Ser Tyr Ser Pro Asp
            595                 600                 605

Asp Asn Arg Phe Asp Leu Arg Pro Phe Leu Tyr Pro Ser Gln Phe Thr
            610                 615                 620

His Gln Phe Arg Lys Ile Asp Glu Leu Ala Gly Lys Leu Pro Asp Met
625                 630                 635                 640

Ala Gln Lys Pro Lys Val Asp Thr Asn Glu Val Asp
            645                 650

<210> SEQ ID NO 26
<211> LENGTH: 677
<212> TYPE: PRT
<213> ORGANISM: Chaetomium globosum

<400> SEQUENCE: 26

Met Gly His Leu Val Thr Val Ala Thr Cys Ser Leu Asn Gln Trp Val
1               5                   10                  15

Leu Asp Trp Glu Gly Asn Leu Gly Arg Ile Ile Glu Ser Ile His Gln
            20                  25                  30

Ala Lys Ala Ala Gly Ala Arg Leu Arg Val Gly Pro Glu Leu Glu Ile
        35                  40                  45

Cys Gly Tyr Ser Ser Leu Asp His Phe His Glu Leu Asp Val Tyr Thr
50                  55                  60

His Ser Leu Glu Met Leu Ala Gln Leu Leu Gln Asp Lys Ser Thr His
65                  70                  75                  80

Gly Ile Leu Leu Asp Val Gly Val Pro Ile Leu His Arg Asn Leu Arg
                85                  90                  95

Tyr Asn Cys Arg Val Ile Cys Leu Asp Gly Lys Ile Leu Leu Ile Arg
            100                 105                 110

Pro Lys Met Trp Leu Ala Asn Asp Gly Asn Tyr Arg Glu Met Arg His
        115                 120                 125

Phe Thr Pro Trp Met Arg Pro Arg Glu Thr Glu Leu Phe His Leu Pro
    130                 135                 140

Lys Ile Leu Ala Glu Leu Gln Gly Glu Thr His Val Leu Phe Gly Asp
145                 150                 155                 160

Ala Val Ile Ser Thr Pro Glu Thr Ala Phe Gly Ala Glu Thr Cys Glu
                165                 170                 175

Glu Leu Phe Thr Pro Lys Ala Pro His Ile Asp Met Ala Leu Asp Gly
            180                 185                 190

Val Glu Ile Ile Thr Asn Ser Ser Gly Ser His Phe Thr Leu Arg Lys
        195                 200                 205

Leu Asp Thr Arg Leu Gln Leu Ile Met Glu Ala Thr Arg Lys Ser Gly
    210                 215                 220

Gly Val Tyr Leu Tyr Ala Asn Gln Gln Gly Cys Asp Gly Glu Arg Leu
225                 230                 235                 240

Tyr Phe Asp Gly Cys Ala Met Ile Ile Val Asn Gly Asp Val Val Ala
                245                 250                 255

Gln Gly Ser Gln Phe Ser Leu Asn Asp Val Glu Val Val Thr Ala Thr
            260                 265                 270
```

```
Val Asp Leu Glu Glu Val Arg Ser Tyr Arg Ala Ala Ile Ser Arg Gly
        275                 280                 285

Leu Gln Ala Ala Ala Ser Thr Ala Lys Tyr Gln Arg Ile Gln Thr Pro
    290                 295                 300

Phe Glu Leu Ser Ser Glu Asp Gly Asp Ala Asp Val Thr Val Ala Pro
305                 310                 315                 320

Thr Leu Leu Ile Gln Pro Arg Tyr His Ser Val Glu Glu Ile Ala
                325                 330                 335

Leu Ser Gly Gly Cys Tyr Leu Trp Asp Tyr Leu Arg Arg Ser Gly Thr
                340                 345                 350

Ala Gly Tyr Leu Val Pro Leu Ser Gly Ile Asp Ser Cys Ala Thr
                355                 360                 365

Ala Gly Ile Val Tyr Ser Leu Cys Arg Ile Val Met Gly Gly Leu Gly
        370                 375                 380

Glu Gly Asn Lys Gln Val Leu Glu Val Gln Arg Ile Pro Lys Tyr
385                 390                 395                 400

Gly Gly Glu Gly Val Phe Thr Thr Pro Gln Glu Leu Cys Lys Pro
                405                 410                 415

Gly Phe Ser Pro Ile Tyr Met Gly Met Lys Lys Gln Ser Ser Arg Glu
                420                 425                 430

Thr Pro Gln Arg Ala Gln Asp Leu Ser Glu Ala Ile Gly Ser Tyr His
                435                 440                 445

Val Asn Leu Asp Ile Asp Asp Glu Val Gly Gln Met Leu Ser Thr Ala
        450                 455                 460

Arg Gln Arg Pro Gly Gly Ser Leu Leu Val Leu Gly Ser Ala Asn
465                 470                 475                 480

Val Gly Glu Ser Leu Arg Gly Tyr Leu Thr Lys Tyr Asp Cys Ser Ser
                485                 490                 495

Ala Asp Ile Asn Pro Ile Gly Ser Ile Asp Lys Ala Asp Leu Lys Arg
                500                 505                 510

Phe Ile Ala Trp Ala Glu Lys Asn Phe Asp Leu Pro Cys Leu His Glu
        515                 520                 525

Phe Leu Thr Ala Val Pro Thr Ala Glu Leu Glu Pro Ile Thr Glu Asp
        530                 535                 540

Tyr Val Gln Ser Asp Glu Ala Asp Met Gly Met Thr Tyr Gln Glu Leu
545                 550                 555                 560

Thr Ile Phe Gly Arg Leu Arg Lys Leu Asn Lys Leu Gly Pro Phe Gly
                565                 570                 575

Met Phe Gln Arg Leu Val His Asp Trp Ser Ile Asp Arg Val Arg Lys
                580                 585                 590

Pro Asp Asp Asp Ala Pro Tyr Tyr Thr Pro Thr Gln Val Ala Glu Lys
                595                 600                 605

Val Lys Lys Phe Phe His Phe Tyr Ala Ile Asn Arg His Lys Met Thr
        610                 615                 620

Thr Leu Thr Pro Ala Leu His Cys Asn Asp Tyr Ser Pro Asp Asp Asn
625                 630                 635                 640

Arg Phe Asp Leu Arg Pro Phe Leu Tyr Pro Pro Phe Trp Lys Ser Trp
                645                 650                 655

Ser Phe Lys Arg Ile Asp Met Glu Leu Glu Lys Ile Glu Arg Lys Arg
                660                 665                 670

Ala Ser Arg Lys Gln
        675

<210> SEQ ID NO 27
```

<211> LENGTH: 689
<212> TYPE: PRT
<213> ORGANISM: Giberella zeae

<400> SEQUENCE: 27

```
Met Ala Asp Leu Ile Thr Leu Ala Thr Cys Ser Leu Asn Gln Trp Val
1               5                   10                  15

Leu Asp Trp Glu Gly Asn Leu Gly Arg Ile Arg Lys Ser Ile Ile Leu
            20                  25                  30

Ala Lys Glu Ala Gly Ala Thr Leu Arg Thr Gly Pro Glu Leu Glu Ile
        35                  40                  45

Thr Gly Tyr Gly Cys Leu Asp His Phe Leu Glu Ala Asp Val Tyr Asp
    50                  55                  60

His Ser Leu Glu Ser Leu Leu Ala Ile Leu Thr Asp Thr Glu Leu His
65                  70                  75                  80

Gly Ile Leu Ile Asp Val Gly Leu Pro Leu Met His Arg Gly Cys Arg
                85                  90                  95

Tyr Asn Cys Arg Ala Ile Ile Leu Asp Gly Lys Leu Leu Cys Leu Arg
            100                 105                 110

Pro Lys Ile Tyr Leu Ala Asn Asp Gly Asn Phe Arg Glu Asn Arg Phe
        115                 120                 125

Phe Thr Pro Trp Asn Arg Pro Arg Tyr Val Glu Gln Tyr Asn Leu Pro
    130                 135                 140

Pro Ala Leu Gln Lys His Gln Gly Val Arg Gln Val Pro Ile Gly Asp
145                 150                 155                 160

Val Ile Leu Ser Leu Asn Asp Thr Thr Val Ala Ala Glu Thr Cys Glu
                165                 170                 175

Glu Leu Phe Thr Pro Gln Ala Pro His Ile Asn Met Ala Leu Asn Gly
            180                 185                 190

Val Glu Ile Phe Thr Asn Ser Ser Gly Ser His His Thr Leu Arg Lys
        195                 200                 205

Leu Asn Glu Arg Leu Ala Leu Ile Ser Glu Ala Thr Arg Lys Ser Gly
    210                 215                 220

Gly Val Tyr Leu Tyr Ala Asn Gln Ser Gly Ser Asp Gly Asp Arg Leu
225                 230                 235                 240

Leu Tyr Asp Gly Ser Ser Leu Ile Met Val Asn Gly Asn Ile Val Ala
                245                 250                 255

Gln Gly Ser Gln Phe Ser Leu Asp Asp Val Glu Val Ile Thr Ala Thr
            260                 265                 270

Val Asp Leu Glu Glu Val Arg Ala Tyr Arg Phe Ala Pro Ser Arg Asn
        275                 280                 285

Phe Gln Ala Val Gln Ala Pro Val Tyr Glu Arg Ile Glu Val Asp Phe
    290                 295                 300

Ser Leu Gly Val Glu Asp Leu Asp Leu Leu Arg Ala Pro Thr Pro Pro
305                 310                 315                 320

Arg Pro Ala Arg Tyr His Val Pro Glu Glu Ile Ala Leu Val Leu
                325                 330                 335

Val Arg Arg Ser Lys Ala Ser Gly Tyr Leu Val Pro Leu Ser Gly Gly
            340                 345                 350

Ile Asp Ser Cys Ala Thr Ala Thr Ile Val Phe Ser Met Cys Arg Leu
        355                 360                 365

Val Val Ala Ala Ile Lys Ala Gly Asn Glu Glu Val Ile Ala Asp Val
    370                 375                 380

Lys Arg Ile Ala Val Tyr Ser Asp Lys Leu Pro Glu Thr Ala Glu Glu
385                 390                 395                 400
```

```
Phe Cys Asn Gln Ile Phe His Thr Val Tyr Met Gly Met Glu Lys Gln
                405                 410                 415

Ser Ser Lys Glu Thr Arg Gln Arg Ala Lys Asp Leu Ser Ala Arg Ile
            420                 425                 430

Gly Ser Tyr His Thr Asp Met Asn Ile Asp Asp Thr Phe Asn Ala Thr
            435                 440                 445

Lys Asn Leu Leu Thr Gln Ala Thr Gly Phe Glu Pro Lys Phe Lys Val
450                 455                 460

His Gly Gly Ser Ala Thr Glu Asn Leu Ala Leu Gln Asn Ile Gln Ala
465                 470                 475                 480

Arg Ser Arg Met Val Val Ala Tyr Tyr Tyr Ala Gln Met Leu Pro Thr
                485                 490                 495

Val Arg Gln Arg Pro Gly Gly Gly Ser Leu Leu Val Leu Gly Ser Ser
            500                 505                 510

Asn Val Asp Glu Cys Leu Arg Gly Tyr Leu Thr Lys Tyr Asp Cys Ser
            515                 520                 525

Ser Ala Asp Val Asn Pro Ile Gly Ser Val Ser Lys Thr Asp Leu Lys
530                 535                 540

Arg Phe Ile Ala Trp Ser Ala Lys Ser Phe Asn Met Pro Ile Leu Glu
545                 550                 555                 560

Glu Phe Ile His Ala Thr Pro Asp Met Gly Met Thr Tyr Asp Glu Leu
                565                 570                 575

Ser Arg Phe Gly Arg Leu Arg Lys Glu Ser Lys Leu Gly Pro Tyr Gly
            580                 585                 590

Met Phe Leu Arg Leu Leu Glu Glu Trp Gly Glu Gly Lys Met Thr
            595                 600                 605

Pro Arg Asp Val Ala Thr Lys Val Lys Arg Phe His Gly Phe His Tyr
            610                 615                 620

Ile Asn Arg His Lys Gln Ala Val Ala Thr Pro Ala Val His Val Glu
625                 630                 635                 640

Asn Tyr Ser Pro Asp Asp His Arg Phe Asp Leu Arg Pro Leu Val Tyr
                645                 650                 655

Pro Ser Pro Trp Asn Ser Trp Ser Phe Glu Lys Ile Asp Lys Arg Val
            660                 665                 670

Glu Ala Ile Glu Arg Ala Met Glu Lys Lys Lys Thr Glu Ile Ser
            675                 680                 685
Lys

<210> SEQ ID NO 28
<211> LENGTH: 674
<212> TYPE: PRT
<213> ORGANISM: Aspergillus fumigatus

<400> SEQUENCE: 28

Met Leu Ala Arg Ile Ile Asp His Pro Asp Cys Gln Asp Ile Val Val
1               5                   10                  15

Asp Val Gly Met Pro Val Arg His Arg Asn Val Arg Tyr Asn Cys Arg
                20                  25                  30

Val Ile Phe Tyr Asn Arg Lys Ile Ile Leu Ile Arg Pro Lys Met Trp
            35                  40                  45

Leu Ala Asn Gly Ile Leu Phe Ser Leu Ala Val Ile Phe Leu Pro Thr
        50                  55                  60

Ser Val Gln Leu Phe Thr Asn His Val Ala Ala Arg Ser Asp Gly Asn
65                  70                  75                  80
```

-continued

```
Tyr Arg Glu Leu Arg His Phe Ser Pro Trp Gln Arg Pro Arg Glu Ile
                85                  90                  95
Glu Asp Tyr Tyr Leu Glu Gln Ile Val Gly Lys Ile Thr Gly Gln Tyr
            100                 105                 110
Lys Val Pro Phe Gly Asp Ala Val Ile Ser Thr Arg Asp Thr Cys Ile
            115                 120                 125
Gly Leu Glu Thr Cys Glu Glu Leu Phe Thr Pro Asn Gly Pro His Ile
        130                 135                 140
Pro Tyr Gly Leu Ala Gly Val Glu Ile Ile Ser Asn Ser Gly Ser
145                 150                 155                 160
His His Glu Leu Lys Lys Leu Asp Thr Arg Val Asn Leu Ile Thr Gln
                165                 170                 175
Ala Thr Lys Leu Ser Gly Gly Ile Tyr Leu Tyr Ala Asn Gln Gln Gly
            180                 185                 190
Cys Asp Gly Asp Arg Leu Tyr Tyr Asp Gly Cys Ala Met Ile Val Ile
            195                 200                 205
Asn Gly Asn Ile Val Ala Gln Gly Ser Gln Phe Ser Leu Lys Asp Val
        210                 215                 220
Glu Val Ile Thr Ala Thr Val Asp Ile Glu Glu Val Arg His Pro Val
225                 230                 235                 240
Arg Thr Tyr Arg Ala Ser Ser Ser Arg Asn Met Gln Ala Thr Arg Gln
                245                 250                 255
Pro Pro Phe Val Arg Leu Asp Leu Asp Val Arg Leu Ser Arg Leu Asp
            260                 265                 270
Asp Asp Ala Glu Pro Gly Leu Val Pro Ser Pro Ile Ser Ala Lys
            275                 280                 285
Tyr His Ala Pro Glu Glu Ile Ser Leu Gly Pro Ala Cys Trp Leu
        290                 295                 300
Trp Asp Tyr Leu Arg Arg Ser Gly Ala Ala Gly Phe Phe Leu Pro Leu
305                 310                 315                 320
Ser Gly Gly Ile Asp Ser Cys Ala Thr Ala Ile Ile Val His Ser Met
                325                 330                 335
Cys Arg Glu Val Val Lys Ala Val Ser Glu Gly Asn Gln Gln Val Ile
            340                 345                 350
Lys Asp Val Arg Arg Leu Cys Ala Glu Pro Glu Gly Ser Thr Trp Leu
            355                 360                 365
Pro Arg Thr Ser Gln Glu Val Cys Asn Arg Ile Phe His Thr Ser Phe
        370                 375                 380
Met Gly Thr Gln Asn Ser Ser Lys Glu Thr Arg Glu Arg Ala Lys Ala
385                 390                 395                 400
Leu Ser Thr Glu Ile Gly Ser Tyr His Ile Asp Phe Asn Phe Asp Thr
                405                 410                 415
Val Val Thr Ala Ile Thr Asn Leu Phe Thr Val Ile Thr Asn Phe Gln
            420                 425                 430
Pro Arg Phe Lys Val His Gly Gly Thr Gly Ala Glu Asn Ala Ala Leu
            435                 440                 445
Gln Asn Val Gln Ala Arg Leu Arg Met Val Leu Ser Tyr Leu Phe Ala
        450                 455                 460
Ser Leu Leu Pro Thr Val Arg Gln Arg Pro Gly Gly Gly Leu Leu
465                 470                 475                 480
Val Leu Ala Ser Ser Asn Val Asp Asp Leu Lys Lys Phe Ile Ala Trp
                485                 490                 495
Ala Arg Asp Ser Phe Asp Leu Pro Ile Leu His Asp Phe Leu Thr Ala
            500                 505                 510
```

```
Thr Pro Thr Ala Glu Leu Glu Pro Ile Thr Ala Thr Tyr Val Gln Ser
        515                 520                 525

Asp Glu Ala Asp Met Gly Val Thr Tyr Ala Glu Leu Gly Thr Phe Gly
        530                 535                 540

Tyr Leu Arg Lys Val Ala Lys Leu Gly Pro Trp Ser Met Tyr Glu Lys
545                 550                 555                 560

Leu Leu His Val Trp Gly Asn Glu Tyr Ser Pro Arg Glu Ile Tyr Glu
                565                 570                 575

Lys Thr Arg His Phe Phe Tyr His Tyr Ala Ile Asn Arg His Lys Met
            580                 585                 590

Thr Val Leu Thr Pro Ser Tyr His Ala Glu Gln Tyr Ser Pro Glu Asp
        595                 600                 605

Asn Arg His Asp Leu Arg Gln Phe Leu Cys Gln Leu Leu Ser Ser Thr
    610                 615                 620

Asp Gly Leu Leu Ala Arg Val Asn Ala Asp Leu Cys Leu Leu Asp Pro
625                 630                 635                 640

Pro Phe Thr Trp Ala Tyr Lys Lys Met Glu Glu Ser Val Lys Tyr Trp
                645                 650                 655

Glu Ser Lys Gly Trp Thr Ala Gly Lys Ala Gln Lys Lys Ser Val Lys
            660                 665                 670

Ala Asp

<210> SEQ ID NO 29
<211> LENGTH: 1315
<212> TYPE: PRT
<213> ORGANISM: Magnaporthe grisea

<400> SEQUENCE: 29

Met Arg Phe Val Thr Val Ala Ala Ala Thr Leu Pro Ser Val Pro Leu
1               5                   10                  15

Asp Phe Glu Gly Asn Arg Asp Arg Ile Leu Glu Ser Ile Lys Leu Ala
            20                  25                  30

Lys Glu Lys Gly Ala Thr Leu Arg Thr Gly Pro Glu Leu Glu Ile Pro
        35                  40                  45

Gly Tyr Gly Cys Leu Asp His His Leu Glu Gly Asp Thr Glu Leu His
    50                  55                  60

Ser Trp Glu Val Leu Ala Glu Ile Ile Ser Asp Pro Val Cys Lys Asp
65                  70                  75                  80

Met Leu Val Asp Leu Gly Leu Gly Val Lys Thr Arg Asn Val Gln Tyr
                85                  90                  95

Asn Cys Arg Val Leu Cys Thr Tyr Lys Lys Ile Tyr Ala Ile Arg Ala
            100                 105                 110

Lys Gln Ala Leu Ala Gly Asp Gly Leu Tyr Arg Glu Pro Arg His Phe
        115                 120                 125

Thr Ala Trp Val Lys Glu Arg Gln Val Glu Thr His Lys Leu His Lys
    130                 135                 140

Val Val Arg Asp Val Thr Gly Gln Thr Val Pro Ile Gly Asp Phe
145                 150                 155                 160

Ile Leu Glu Thr Pro Asp Thr Ser Val Thr Cys Glu Thr Cys Glu Glu
                165                 170                 175

Leu Phe Val Pro Arg Asn Pro Ser Ile Phe Ser Gly Leu Asn Gly Ala
            180                 185                 190

Glu Ile Ile Leu Asn Ser Ser Ala Ser His Ala Glu Leu Arg Lys Leu
        195                 200                 205
```

-continued

```
Gly Thr Arg Leu Asn Leu Ile Ser Asn Ser Thr Arg Ser Asn Gly Gly
    210                 215                 220
Leu Tyr Val Tyr Ala Asn Ala Ser Gly Ile Asp Gly Glu Ala Arg Met
225                 230                 235                 240
Leu Phe Asp Gly Ser Ser Met Ile Ile Gln Asn Gly Glu Val Leu Ala
                    245                 250                 255
Gln Ser Ser Gln Phe Ser Leu Leu Pro Val Glu Val Thr Val Ala Thr
                260                 265                 270
Val Asp Leu Glu Arg Val Arg Ser Tyr Arg Thr Ser Ala Ser Arg Asn
            275                 280                 285
Val Gln Ala Ala Arg Gln Pro Glu Tyr Pro Arg Ile Asp Cys Asp Ile
290                 295                 300
Glu Leu Ala Arg Pro Ser Glu Glu Ile Phe Arg Ser Asn Lys Val Ile
305                 310                 315                 320
Ala Met Glu Ile Pro Ile Arg Ile Leu Asp Pro Met Glu Glu Ile His
                    325                 330                 335
Met Ala Thr Ser Val Tyr Leu Trp Gln Tyr Leu Val Arg Ser Ser Gly
                340                 345                 350
Ala Gly Phe Phe Leu Ala Leu Ser Gly Gly Leu Asp Ser Ser Ser Val
            355                 360                 365
Ala Leu Phe Val Tyr Gly Met Ala Lys Leu Val Leu Leu Ser Ile Lys
370                 375                 380
Asn Gly Glu Glu Asn Thr Leu Asn Asp Leu Arg Lys Val Thr Gly Ile
385                 390                 395                 400
Asn Asp Tyr Val Pro Glu Ser Pro Glu Glu Ile Val Gly Lys Leu Leu
                    405                 410                 415
His Thr Cys Phe Met Gly Thr Val Asn Ser Ser Asp Glu Thr Arg Ser
                420                 425                 430
Arg Ala Lys Arg Leu Ala Glu Arg Leu Gly Ala Tyr His Thr Asp Ile
            435                 440                 445
Asn Ile Asp Asn Ala Val Gln Ala His Glu Ser Ile Ile Glu Ser Ala
        450                 455                 460
Leu Gly Gly Phe Lys Pro Lys Tyr Ala Val Glu Gly Gly Thr Asn Ser
465                 470                 475                 480
Glu Asn Leu Ala Lys Gln Asn Ile Gln Ala Arg Asn Arg Leu Val Val
                    485                 490                 495
Ser Tyr Glu Leu Ala Gln Leu Ser Thr Gln Ala Arg Gly Leu Pro Arg
                500                 505                 510
Ala Gly Ala Ser Leu Leu Val Leu Gly Ser Gly Asn Val Asp Glu Asn
            515                 520                 525
Leu Arg Gly Tyr Tyr Thr Lys Tyr Asp Ala Ser Ser Ala Asp Leu Ala
530                 535                 540
Pro Leu Gly Ser Ile Ser Lys Asn Asp Ala Lys Asp Phe Gln Arg Trp
545                 550                 555                 560
Ala Arg Asp Asn Trp Asp Leu Ser Ile Met Ser Glu Phe Ile Asp Ala
                    565                 570                 575
Ile Pro Ser Ala Glu Leu Leu Pro Leu Ser Ala Gly Val Gln Ala Asp
                580                 585                 590
Glu Val Glu Met Gly Leu Thr Tyr Ser Glu Leu Ser Asp Phe Gly Ile
            595                 600                 605
Leu Arg Lys Val Asp Lys Leu Gly Pro Trp Ser Ala Tyr Leu Arg Leu
        610                 615                 620
Leu Ser Gln Trp Lys Glu Arg Pro Gly Phe Gly Pro Arg Glu Ile Ala
625                 630                 635                 640
```

```
Glu Lys Val Phe Leu Phe Phe Arg Phe Tyr Ala Ile Asn Arg His Lys
            645                 650                 655

Ala Thr Ile Ile Thr Pro Ser Val His Leu Ser Ala Tyr Asn Pro Asp
            660                 665                 670

Asp Asn Arg His Asp Asn Asn Arg Glu Lys Lys Ser Ile Ala Ser
            675                 680                 685

Ile Trp Gln Ser Gln Ala Phe Ser Ala Thr Gly Asp Leu Pro Thr Leu
            690                 695                 700

Leu Leu Ala Gly Ala Lys Leu Pro Lys Ile Asn Pro Ser Leu Arg Arg
705                 710                 715                 720

Lys Cys Asp Ser Arg Leu Asp Ser Asn Gly Lys Arg Arg Cys Pro Ser
                725                 730                 735

Gly Val Thr Pro Asn Phe Gln Pro Gln Pro Ala His Leu Gln Val Leu
                740                 745                 750

Thr Pro Ser Thr Ser Asn Arg Leu Glu Ile Asp Ala Thr Ser Arg Ala
                755                 760                 765

His Phe Ile Gly Trp Leu Cys Gly Ser Leu Leu Ala Thr Ala Val Ser
            770                 775                 780

Ala Thr Asn Phe Ala Asn Cys Tyr His Leu Ala Phe Glu Glu Phe Arg
785                 790                 795                 800

Asn Gly Thr His Pro Met Arg Asp Ser Phe Phe Trp Lys Glu Lys Asp
                805                 810                 815

Pro Leu Ile Gly Leu Lys Asn Gln Ser Ala Arg Pro Glu Ile Val Leu
                820                 825                 830

Thr Arg Ala Gly Cys Glu His Phe Cys Ser Ile Tyr Pro Gln Tyr Asn
                835                 840                 845

Asn Val Ile Asp Ala Phe Gln Ile Leu Thr Thr Trp Val Leu Pro Ala
            850                 855                 860

Ile Ala Leu Met Ser Gln Leu Pro Tyr Glu Ser Leu Ser Val Arg Trp
865                 870                 875                 880

Arg Lys Asn Leu Ala Ala Phe Gly Asn Trp Val Gly Ala Pro Ala Ala
                885                 890                 895

Ala Met Thr Thr Thr Phe Trp Asn Ile Val Leu Ile His Glu Cys Ser
                900                 905                 910

Val Lys Phe Gly Leu Phe Arg Leu Pro Glu Thr Arg Glu Glu Ile Arg
            915                 920                 925

Asp Ala Leu Phe Ile Leu Ser Cys Val Asn Gln Tyr Glu Tyr Pro Arg
            930                 935                 940

Arg Glu Gln Val Gly Arg Asp Leu Arg Arg Asp Ser Ala Leu Leu Lys
945                 950                 955                 960

Gly Ile Leu Tyr Pro Tyr Phe Lys Asp Gly Ile Ser Glu Arg Gln Arg
            965                 970                 975

Arg Thr Leu Ala Asn Phe Asn Gln His Leu Ala Phe Gly Leu Arg Leu
            980                 985                 990

Gln Arg Arg Lys Gly Val Tyr Pro Ile Phe Ile Ser Ile Gly Trp Phe
        995                 1000                1005

Gly Met Ala Phe Ala Phe Ser Ile Val Ile Ser Phe Ala Ala Leu
        1010                1015                1020

Gly Asp Asn Thr Thr Ala His Ser Leu Ala Leu Gly Leu Leu Leu
        1025                1030                1035

Ser Trp Val Pro Val Met Leu Phe Ala Thr Val Ile Asp Arg Asn
        1040                1045                1050

Pro Thr Ser Ala Thr Arg Cys Ser Glu Leu Ile Gln Arg Trp Leu
```

```
                1055                1060                1065

Phe  Asn  Ile  Asp  Arg  Leu  Leu  Pro  Ala  Thr  Asp  Leu  Ser  Ser  Leu
               1070                1075                1080

Pro  Pro  Lys  Phe  Trp  Gln  Ala  His  His  Gly  Gly  Gln  Lys  His  Ala
               1085                1090                1095

Asp  Thr  Thr  Glu  Glu  Phe  Asp  Ile  Gly  Glu  Tyr  Met  Gly  Gln  Gly
               1100                1105                1110

Arg  Thr  Leu  Arg  Tyr  Cys  Gly  Val  Ala  Asp  Thr  Val  Leu  Asp  Met
               1115                1120                1125

Ile  Lys  Asn  Pro  Ser  Glu  Ala  Thr  Leu  Asp  Val  Pro  Asp  Leu  Ser
               1130                1135                1140

Val  Gly  Lys  Lys  His  Ala  Lys  Phe  Ser  Asp  Arg  Ser  Asp  Glu  Ala
               1145                1150                1155

Thr  Val  Gly  Met  Gly  Gly  Gly  Val  Ala  His  Gln  Pro  Gly  His  Cys
               1160                1165                1170

Asp  His  Gln  Leu  Arg  His  Gly  Leu  His  Gly  Val  Val  Gln  His  Ala
               1175                1180                1185

Asn  Ala  Gly  Ser  Gly  Leu  Ser  Leu  Ala  Ala  Leu  Pro  Leu  Leu  Val
               1190                1195                1200

Ala  Pro  Gly  Ser  Ala  Leu  Val  Ala  Asp  Pro  Gly  Ser  Leu  Ser  Gly
               1205                1210                1215

Ala  Gln  His  Gln  Met  Gln  Ser  Phe  Gly  Gly  Leu  Asn  Ser  Cys  Leu
               1220                1225                1230

Cys  Lys  Thr  Ser  Val  Phe  Gly  Leu  Pro  Pro  Phe  Gly  Arg  Tyr  Met
               1235                1240                1245

Asp  Phe  Glu  Asn  Ala  Glu  Phe  Tyr  Lys  Glu  Tyr  Tyr  Tyr  Val  Glu
               1250                1255                1260

Ala  Phe  Trp  Gly  Ser  Ala  Thr  Gly  Ile  Gly  Gly  Ala  Thr  Met  Ala
               1265                1270                1275

Ile  Ser  Val  Ser  Trp  Leu  Ala  Trp  Lys  Trp  His  Lys  Ser  Ser  Ala
               1280                1285                1290

Leu  Trp  Arg  Val  Thr  Glu  Asp  Thr  Thr  Val  Arg  Val  Glu  Asp  Asp
               1295                1300                1305

Val  Ser  Leu  Asp  Trp  Leu  Thr
               1310                1315

<210> SEQ ID NO 30
<211> LENGTH: 401
<212> TYPE: PRT
<213> ORGANISM: Saccharomyces cereviseae

<400> SEQUENCE: 30

Met  Asp  Pro  Thr  Arg  Ala  Pro  Asp  Phe  Lys  Pro  Ser  Ala  Asp  Glu
 1                 5                  10                  15

Glu  Leu  Ile  Pro  Pro  Asp  Pro  Ser  Lys  Ile  Pro  Lys  Ser  Ile
                20                  25                  30

Pro  Ile  Ile  Pro  Tyr  Val  Leu  Ala  Asp  Ala  Asn  Ser  Ser  Ile  Asp  Ala
                35                  40                  45

Pro  Phe  Asn  Ile  Lys  Arg  Lys  Lys  His  Pro  Lys  His  His  His
                50                  55                  60

His  His  His  Ser  Arg  Lys  Glu  Gly  Asn  Asp  Lys  Lys  Gln  His  Ile
 65                 70                  75                  80

Pro  Leu  Asn  Gln  Asp  Asp  Phe  Gln  Pro  Leu  Ser  Ala  Glu  Val  Ser  Ser
                85                  90                  95

Glu  Asp  Asp  Asp  Ala  Asp  Phe  Arg  Ser  Lys  Glu  Arg  Tyr  Gly  Ser  Asp
```

```
                    100                 105                 110
Ser Thr Thr Glu Ser Glu Thr Arg Gly Val Gln Lys Tyr Gln Ile Ala
            115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
                180                 185                 190

Ser Glu Gln Thr Arg Phe Glu Val Ile Gly Gly Tyr Tyr Ser Pro Val
                195                 200                 205

Ser Asp Asn Tyr Gln Lys Gln Gly Leu Ala Pro Ser Tyr His Arg Val
            210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
                260                 265                 270

Thr Val Thr Gly Glu Lys Ile Gly Val Lys Ile Met Leu Leu Ala Gly
                275                 280                 285

Gly Asp Leu Ile Glu Ser Met Gly Glu Pro Asn Val Trp Ala Asp Ala
            290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Lys Gln Leu Ile Tyr Asn Asp
                340                 345                 350

Ile Ser Ser Thr Lys Val Arg Leu Phe Ile Arg Arg Ala Met Ser Val
            355                 360                 365

Gln Tyr Leu Leu Pro Asn Ser Val Ile Arg Tyr Ile Gln Glu His Arg
            370                 375                 380

Leu Tyr Val Asp Gln Thr Glu Pro Val Lys Gln Val Leu Gly Asn Lys
385                 390                 395                 400

Glu

<210> SEQ ID NO 31
<211> LENGTH: 411
<212> TYPE: PRT
<213> ORGANISM: Candida glabrata

<400> SEQUENCE: 31

Met Asp Pro Thr Arg Asp Pro Asp Phe Lys Pro Arg Asp Pro Asp Ala
1               5                   10                  15

Lys Leu Leu Pro Pro Asp Pro Thr Ser Lys Ile Pro Lys Ser Gly
            20                  25                  30

Pro Ile Thr Pro Tyr Val Leu Ala Asp Tyr Asn Ala Ser Ile Asp Ala
            35                  40                  45

Pro Leu Gln Met Lys Lys Asn Thr Thr His Leu Pro His Ser Gln Gly
        50                  55                  60

Asn His Gln Arg Ile Pro Leu Asn Lys Ser Glu Phe Gln Pro Leu Ser
65                  70                  75                  80
```

```
Thr Thr Gly Ser Ser Glu Glu Asp Phe Glu Leu Asp Asp Glu Asn Met
                85                  90                  95

Asp Ser Asp Ser Gly Ser Lys Arg Glu Ser Leu Gly Gln Leu Ser Gly
            100                 105                 110

His Gly Ile Gly Ile Gly Val His Lys Asn Gln Ile Ala Asp Leu Glu
        115                 120                 125

Glu Val Pro His Gly Ile Val Arg Gln Ala Arg Phe Leu Glu Asp Tyr
    130                 135                 140

Glu Phe Pro Thr His Arg Leu Ala Asn Arg Leu Gln Asp Pro Asn Lys
145                 150                 155                 160

Met Pro Leu Val Ile Val Ala Cys Gly Ser Phe Ser Pro Ile Thr Tyr
                165                 170                 175

Leu His Leu Arg Met Phe Glu Met Ala Leu Asp Ala Ile Ser Glu Met
            180                 185                 190

Thr Arg Phe Glu Val Val Gly Gly Tyr Tyr Ser Pro Val Ser Asp Asn
        195                 200                 205

Tyr Lys Lys Gln Gly Leu Ala Pro Ser Tyr His Arg Val Arg Met Cys
    210                 215                 220

Glu Leu Ala Cys Glu Arg Thr Ser Ser Trp Leu Met Val Asp Ala Trp
225                 230                 235                 240

Glu Ser Leu Gln Pro Ser Tyr Thr Arg Thr Ala Lys Val Leu Asp His
                245                 250                 255

Phe Asn His Glu Ile Asn Val Lys Arg Gly Gly Ile Thr Val His Glu
            260                 265                 270

Lys Lys Arg Asn Ala Asp Asn Ser Gly Tyr His Met Glu Glu His Lys
        275                 280                 285

Arg Gly Val Lys Ile Met Leu Leu Ala Gly Gly Asp Leu Ile Glu Ser
    290                 295                 300

Met Gly Glu Pro Gly Val Trp Ala Asp Glu Asp Leu His His Ile Leu
305                 310                 315                 320

Gly Asn Tyr Gly Cys Leu Ile Val Glu Arg Thr Gly Ser Asp Val Arg
                325                 330                 335

Ser Phe Leu Leu Ser His Asp Ile Met Tyr Glu His Arg Arg Asn Val
            340                 345                 350

Leu Val Ile Lys Gln Leu Ile Tyr Asn Asp Ile Ser Ser Thr Lys Val
        355                 360                 365

Arg Leu Phe Ile Arg Arg Asn Met Ser Val Gln Tyr Leu Leu Pro Asn
370                 375                 380

Ser Val Ile Arg Tyr Ile Gln Glu His Lys Leu Tyr Ile Asn Gln Ser
385                 390                 395                 400

Glu Pro Val Lys Gln Val Leu Ser Gly Lys Glu
                405                 410

<210> SEQ ID NO 32
<211> LENGTH: 400
<212> TYPE: PRT
<213> ORGANISM: Eremothecium gossypii

<400> SEQUENCE: 32

Met Asp Pro Thr Arg Ala Pro Asp Phe Lys Pro Leu Gln Gly Asp Asp
1               5                   10                  15

Lys Pro Glu Pro Pro Leu Ala Pro Asp Ser Glu Ile Pro Glu Asn Gly
            20                  25                  30

Pro Ile Met Pro Phe Val Leu Ala Asp Tyr Asn Thr Ser Ile Asp Ala
        35                  40                  45
```

```
Pro Ile His Pro Lys Ser Tyr Lys Ser Met Lys Arg Asn Ser Ser
         50                  55                  60
Gln Pro Ser Asn Cys Ser Lys Gly Arg Gly Gly Ser Gly Ser Ile Pro
 65                  70                  75                  80
Leu Lys Arg Ser Gly Leu Glu Pro Phe Ser Asn Asp Val Ser Ser Glu
                 85                  90                  95
Ser Glu Cys Gly Glu Glu Asp Glu Gln Gln Gly Glu Ser His Ala Ala
            100                 105                 110
Asp Ala Asn Ser Ser Lys Leu Arg Ser Met Val Gln Asn Ile Ala Asp
        115                 120                 125
Leu Glu Glu Val Pro Cys Gly Ile Ile Arg Gln Ala Arg Ile Leu Glu
130                 135                 140
Asp Tyr Glu Phe Pro Thr His Arg Leu Lys Thr Thr Leu His Asn Ala
145                 150                 155                 160
Asn Lys Leu Pro Leu Val Ile Val Ala Cys Gly Ser Phe Leu Pro Ile
                165                 170                 175
Thr His Leu His Leu Arg Met Phe Glu Met Ala Met Asp Ala Ile Val
            180                 185                 190
Glu Gln Thr Arg Phe Glu Val Val Gly Gly Tyr Tyr Ser Pro Val Ser
        195                 200                 205
Asp Asn Tyr Asn Lys Pro Gly Leu Ala Ser Ala Thr His Arg Val Arg
210                 215                 220
Met Cys Glu Leu Ala Cys Glu Arg Thr Ser Ser Trp Leu Met Val Asp
225                 230                 235                 240
Ala Trp Glu Ser Leu Gln Pro Gln Tyr Thr Arg Thr Ala Lys Val Leu
                245                 250                 255
Asp His Phe Asn Asp Glu Ile Asn Val Lys Arg Gly Gly Ile Lys Thr
            260                 265                 270
Ser Thr Gly Asp Arg Ile Gly Val Lys Ile Met Leu Leu Ala Gly Gly
        275                 280                 285
Asp Leu Ile Glu Ser Met Gly Glu Pro Asn Val Trp Ala Asp Ala Asp
290                 295                 300
Leu His His Ile Leu Gly Asn Tyr Gly Cys Leu Ile Val Glu Arg Thr
305                 310                 315                 320
Gly Ser Asp Val Arg Ser Phe Leu Leu Ser His Asp Ile Met Tyr Glu
                325                 330                 335
His Arg Arg Asn Ile Leu Val Ile Lys Gln Met Ile Tyr Asn Asp Ile
            340                 345                 350
Ser Ser Thr Lys Val Arg Leu Phe Ile Arg Arg Gly Met Ser Val Gln
        355                 360                 365
Tyr Leu Leu Pro Asn Ser Val Ile Arg Tyr Ile Gln Glu Tyr Gly Leu
370                 375                 380
Tyr Val Asn Glu His Glu Pro Val Gln Gln Val Ile Ser Asn Lys Asp
385                 390                 395                 400

<210> SEQ ID NO 33
<211> LENGTH: 449
<212> TYPE: PRT
<213> ORGANISM: Kluyveromyces lactis

<400> SEQUENCE: 33

Met Asp Pro Thr Arg Asp Pro Asn Phe Lys Ser Pro Gln Glu Leu Asp
1               5                  10                  15
Ser Glu Ala Leu Gln Ser Ser Thr Asp Ile Pro Lys Ile Gly Pro Ile
            20                  25                  30
```

```
Ile Pro Tyr Val Leu Ala Asp Tyr Asn Thr Ala Ile Asp Lys Pro Ile
         35                  40                  45

Arg Pro Arg Lys Tyr Lys Lys Asn Ala Ile Lys Arg Lys Leu Ala Ser
 50                  55                  60

Ser Met Thr Ser Thr Ser Asp Asp Ser Asn Glu Gln Gln His Leu Ser
 65                  70                  75                  80

Ala Asn Ser Asn Asn Gly Phe Ile Pro Leu Lys Gln Arg Glu Leu Gln
                 85                  90                  95

Pro Val Ser Ala Glu Thr Ser Gly Asp Ser Glu Ser Glu Ser Glu Ser
            100                 105                 110

Pro Ala Glu Pro Ala Asn Val Asp Leu Asp Ile Asp Pro Asn Pro Glu
            115                 120                 125

Ser Asp Glu Val Met Ala Ser Ala Pro Val Ala His Ala Ser Gly Ser
130                 135                 140

Val Ser Gly Pro Ser Gly Met Ala Ala Ala Ala Ala Ala Ala Ala Ser
145                 150                 155                 160

Leu Asp Gln Glu Ile Thr Ser Arg Ile His Lys Phe Gln Ile Ala Asp
                165                 170                 175

Leu Glu Glu Val Pro His Gly Ile Val Arg Gln Ala Asn Asn Trp Lys
                180                 185                 190

Asp Tyr Gln Phe Pro Ala His Arg Leu Lys Gln Arg Leu Arg Asn Ser
            195                 200                 205

Asn Lys Leu Pro Leu Val Ile Val Ala Cys Gly Ser Phe Ser Pro Ile
            210                 215                 220

Thr Tyr Leu His Leu Arg Met Phe Glu Met Ala Leu Asp Ala Ile Ser
225                 230                 235                 240

Glu Gln Thr Arg Phe Glu Val Ile Gly Gly Tyr Tyr Ser Pro Val Ser
                245                 250                 255

Asp Asn Tyr Lys Lys Pro Gly Leu Ala Pro Ala His His Arg Val Arg
            260                 265                 270

Met Cys Glu Leu Gly Cys Glu Arg Thr Ser Ser Trp Leu Met Val Asp
            275                 280                 285

Ala Trp Glu Ser Leu Gln Pro Thr Tyr Thr Arg Thr Ala Met Val Leu
            290                 295                 300

Asp His Phe Asn Glu Glu Ile Asn Val Lys Arg Lys Gly Val Ile Lys
305                 310                 315                 320

Asn Asp Ala Gly Glu Arg Met Gly Val Lys Ile Met Leu Leu Ala Gly
                325                 330                 335

Gly Asp Leu Ile Glu Ser Met Gly Glu Pro Asn Val Trp Ala Asp Tyr
                340                 345                 350

Asp Leu His His Ile Leu Gly Asn Tyr Gly Cys Leu Ile Val Glu Arg
            355                 360                 365

Thr Gly Ser Asp Val Arg Ser Phe Leu Leu Ser His Asp Ile Met Tyr
370                 375                 380

Glu His Arg Arg Asn Ile Leu Val Ile Lys Gln Leu Ile Tyr Asn Asp
385                 390                 395                 400

Ile Ser Ser Thr Lys Val Arg Leu Phe Ile Arg Arg Met Ser Val
                405                 410                 415

Gln Tyr Leu Leu Pro Asn Ser Val Ile Arg Tyr Ile Gln Glu His Gly
            420                 425                 430

Leu Tyr Val Asn Gln Thr Glu Pro Val Lys Gln Val Ile Gly Asn Lys
            435                 440                 445

Asp
```

<210> SEQ ID NO 34
<211> LENGTH: 400
<212> TYPE: PRT
<213> ORGANISM: Debyaromyces hansenii

<400> SEQUENCE: 34

```
Met Asp Pro Thr Arg Ala Pro Asp Phe Lys Pro Leu Gln Gly Asp
1               5                   10                  15

Lys Pro Glu Pro Pro Leu Ala Pro Asp Ser Glu Ile Pro Glu Asn Gly
                20                  25                  30

Pro Ile Met Pro Phe Val Leu Ala Asp Tyr Asn Thr Ser Ile Asp Ala
            35                  40                  45

Pro Ile His Pro Lys Ser Tyr Lys Lys Ser Met Lys Arg Asn Ser Ser
        50                  55                  60

Gln Pro Ser Asn Cys Ser Lys Gly Arg Gly Gly Ser Gly Ser Ile Pro
65                  70                  75                  80

Leu Lys Arg Ser Gly Leu Glu Pro Phe Ser Asn Asp Val Ser Ser Glu
                85                  90                  95

Ser Glu Cys Gly Glu Glu Asp Glu Gln Gln Gly Glu Ser His Ala Ala
            100                 105                 110

Asp Ala Asn Ser Ser Lys Leu Arg Ser Met Val Gln Asn Ile Ala Asp
        115                 120                 125

Leu Glu Glu Val Pro Cys Gly Ile Ile Arg Gln Ala Arg Ile Leu Glu
130                 135                 140

Asp Tyr Glu Phe Pro Thr His Arg Leu Lys Thr Thr Leu His Asn Ala
145                 150                 155                 160

Asn Lys Leu Pro Leu Val Ile Val Ala Cys Gly Ser Phe Leu Pro Ile
                165                 170                 175

Thr His Leu His Leu Arg Met Phe Glu Met Ala Met Asp Ala Ile Val
            180                 185                 190

Glu Gln Thr Arg Phe Glu Val Val Gly Gly Tyr Tyr Ser Pro Val Ser
        195                 200                 205

Asp Asn Tyr Asn Lys Pro Gly Leu Ala Ser Ala Thr His Arg Val Arg
210                 215                 220

Met Cys Glu Leu Ala Cys Glu Arg Thr Ser Ser Trp Leu Met Val Asp
225                 230                 235                 240

Ala Trp Glu Ser Leu Gln Pro Gln Tyr Thr Arg Thr Ala Lys Val Leu
                245                 250                 255

Asp His Phe Asn Asp Glu Ile Asn Val Lys Arg Gly Gly Ile Lys Thr
            260                 265                 270

Ser Thr Gly Asp Arg Ile Gly Val Lys Ile Met Leu Leu Ala Gly Gly
        275                 280                 285

Asp Leu Ile Glu Ser Met Gly Glu Pro Asn Val Trp Ala Asp Ala Asp
290                 295                 300

Leu His His Ile Leu Gly Asn Tyr Gly Cys Leu Ile Val Glu Arg Thr
305                 310                 315                 320

Gly Ser Asp Val Arg Ser Phe Leu Leu Ser His Asp Ile Met Tyr Glu
                325                 330                 335

His Arg Arg Asn Ile Leu Val Ile Lys Gln Met Ile Tyr Asn Asp Ile
            340                 345                 350

Ser Ser Thr Lys Val Arg Leu Phe Ile Arg Arg Gly Met Ser Val Gln
        355                 360                 365

Tyr Leu Leu Pro Asn Ser Val Ile Arg Tyr Ile Gln Glu Tyr Gly Leu
370                 375                 380
```

```
Tyr Val Asn Glu His Glu Pro Val Gln Gln Val Ile Ser Asn Lys Asp
385                 390                 395                 400
```

<210> SEQ ID NO 35
<211> LENGTH: 401
<212> TYPE: PRT
<213> ORGANISM: Candida albicans

<400> SEQUENCE: 35

```
Met Asp Pro Thr Asn Asp Pro Asn Phe Thr Pro Ser Leu Asn Lys
1               5                   10                  15

Asn Ile Glu Pro Thr Ala Pro Ser Asp Lys Ile Pro Ser Ile Met Pro
                20                  25                  30

Ile Gln Pro Phe Val Leu Glu Glu Leu Gly Glu Gly Val Asp Gly Pro
                35                  40                  45

Val Pro His Pro Ala Ser Ser Ser Arg Pro Thr Pro Thr Thr Ala Arg
            50                  55                  60

Ser Tyr Asp Ala Ser His Ala Ser Asp Thr Glu Ser Lys Tyr His Ser
65                  70                  75                  80

Lys Ile Pro Arg Lys His Thr Glu Leu Ile Ser Ser Ser Ser Ser Asp
                85                  90                  95

Glu Glu Asn Glu Pro Leu Ser Pro Lys Pro Glu Ile Ile Pro Pro Lys
                100                 105                 110

Lys Glu Ile Leu Pro Pro Ser Ile Lys Val Arg Ser Ser Gln Ile Ala
                115                 120                 125

Asp Leu Glu Glu Val Pro His Gly Ile Gln Arg Gln Ala Leu Lys Leu
130                 135                 140

Glu Asp Tyr His Phe Pro Thr His Arg Leu Ala Thr Thr Leu Thr Asp
145                 150                 155                 160

Asp Ser Lys His Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
                180                 185                 190

Thr Glu Gln Thr Arg Phe Glu Val Ile Gly Gly Tyr Tyr Ser Pro Val
                195                 200                 205

Ser Ser Asn Tyr Lys Lys Gln Gly Leu Ala Pro Ala His His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Lys Tyr Thr Arg Thr Ala Leu Val
                245                 250                 255

Leu Asp His Phe Asn Glu Glu Ile Asn Ile Lys Gln Gly Gly Ile Met
                260                 265                 270

Thr Arg Ser Gly Glu Lys Arg Gly Val Lys Ile Met Leu Leu Ala Gly
                275                 280                 285

Gly Asp Leu Ile Glu Ser Met Gly Glu Pro Asp Val Trp Ala Asp Gln
290                 295                 300

Asp Leu His His Ile Leu Gly Lys Tyr Gly Cys Leu Ile Val Glu Arg
305                 310                 315                 320

Thr Gly Ser Asp Val Arg Ser Phe Leu Leu Ser His Asp Ile Leu Tyr
                325                 330                 335

Glu His Arg Lys Asn Ile Leu Val Ile Lys Gln Leu Ile Tyr Asn Asp
                340                 345                 350

Ile Ser Ser Thr Lys Ile Arg Leu Phe Ile Arg Arg Gly Met Ser Val
                355                 360                 365
```

-continued

```
Gln Tyr Leu Leu Pro Asn Ser Val Ile Arg Tyr Ile Gln Gln His Asn
    370                 375                 380

Leu Tyr Gly Asp Ser Glu Pro Val Lys Gln Val Met Ser Asp Arg Ala
385                 390                 395                 400

Asp

<210> SEQ ID NO 36
<211> LENGTH: 470
<212> TYPE: PRT
<213> ORGANISM: Yarrowia lipolytica

<400> SEQUENCE: 36

Met Asp Pro Lys Leu Ala Pro Asn Phe Val Arg Pro Ser Asp Lys Arg
1               5                   10                  15

Pro Thr Ala Tyr Arg Ser Pro Ala Pro Ala Gln Ala Ser Leu Ile Pro
            20                  25                  30

Asn Ile Ala Pro Ile Gln Pro Tyr Val Leu Glu Asp Ser Gln His Glu
        35                  40                  45

Ile Asp Leu Pro Gln Asp Ser Pro Arg Leu Leu Pro Ser Arg Thr Asn
    50                  55                  60

Ser Arg Asp Ser Leu Val Gly Leu Glu Gln Ile Ala Leu Thr Leu Lys
65                  70                  75                  80

His His Ser Lys His Asn Pro Lys Asp Ser Asn Tyr His Pro Ala Pro
                85                  90                  95

Val Asn Ile Pro Arg Ile His Ser Glu Leu Asn Met Ser Asp Ser Ser
            100                 105                 110

Pro Asp Arg Cys Glu Lys Ile Asp Glu Val Asp Leu Glu Val Ser Pro
        115                 120                 125

Asn Glu Ile Gln Thr Asn Phe Ser Lys Phe Ser Leu Gly Asp Gln Ala
    130                 135                 140

Leu Pro Pro Thr Thr Val Glu Glu Ala Met Ala Pro Thr Ser Pro Lys
145                 150                 155                 160

Ser Pro Lys Glu Pro Gln Val His Thr Glu Thr Gly Thr Ala Asp Ser
                165                 170                 175

Ser Ser Arg Thr Pro Pro Tyr Leu Leu Asp Asn Ser Gly Leu Arg Pro
            180                 185                 190

Ile Ile Gln Ser Ala Asp Leu Glu Glu Val Pro Ile Gly Val Ser Arg
        195                 200                 205

Gln Ala Arg Asp Leu Asp His Tyr Lys Phe Pro Thr His Arg Leu Ser
    210                 215                 220

Glu Val Met Ile Glu Thr Lys Ser Pro Leu Val Ile Val Ala Cys
225                 230                 235                 240

Gly Ser Phe Ser Pro Ile Thr Tyr Leu His Leu Arg Met Phe Glu Met
                245                 250                 255

Ala Met Asp Ser Ile Arg Glu Gln Thr Arg Phe Glu Val Ile Gly Gly
            260                 265                 270

Tyr Tyr Ser Pro Val Ser Asp Asn Tyr Asn Lys Pro Gly Leu Ala Pro
        275                 280                 285

Ala His His Arg Val Arg Met Cys Glu Leu Ala Cys Glu Arg Thr Ser
    290                 295                 300

Ser Trp Leu Met Val Asp Ala Trp Glu Ser Leu Gln Pro Thr Tyr Gln
305                 310                 315                 320

Arg Thr Ala Thr Val Leu Asp His Phe Asn Glu Ile Asn Ile Lys
                325                 330                 335
```

```
Arg Gly Gly Ile Lys Thr Val Ser Gly Lys Arg Lys Gly Val Lys Ile
            340                 345                 350

Met Leu Leu Ala Gly Gly Asp Leu Ile Glu Ser Met Gly Glu Pro Asn
            355                 360                 365

Val Trp Glu Glu Arg Asp Leu His His Ile Leu Gly Arg Tyr Gly Cys
        370                 375                 380

Leu Ile Val Glu Arg Thr Gly Ala Asp Val Arg Ser Phe Leu Leu Ser
385                 390                 395                 400

His Asp Ile Met Tyr Glu His Arg Arg Asn Val Leu Val Ile Lys Gln
            405                 410                 415

Leu Ile Tyr Asn Asp Ile Ser Ser Thr Lys Val Arg Leu Phe Ile Arg
        420                 425                 430

Arg Gly Met Ser Val Gln Tyr Leu Ile Pro Asn Ser Val Ile Arg Tyr
            435                 440                 445

Ile Gln Glu His Arg Leu Tyr Val Gly Glu Thr Glu Pro Val Lys Gln
450                 455                 460

Val Leu Tyr Asp Arg Glu
465                 470

<210> SEQ ID NO 37
<211> LENGTH: 365
<212> TYPE: PRT
<213> ORGANISM: Schizosaccharomyces pombe

<400> SEQUENCE: 37

Met Asn Gly Asp Asn Phe Ala Asn Ser Phe Pro Lys Asn Pro Leu Leu
1               5                   10                  15

Ser Arg Asn Ser Ser Ser Ser Asn Val Ile Gln Tyr Ser Asp Glu Phe
            20                  25                  30

Ser Pro Asp Glu Asp Trp Leu Asn Glu His Ala Ala Lys Glu His Glu
        35                  40                  45

Glu Arg Ile Arg Arg Pro Ser Val Asn Arg Ala Trp Gln Lys Asn Ser
    50                  55                  60

Thr Ser Gly Gly Pro Ser Val Ser Leu Glu Lys Arg Glu Ala Asp Val
65                  70                  75                  80

Ala Ser Leu Gly Glu Val Met Asp Leu Glu Glu Val Pro Arg Gly Ile
                85                  90                  95

Thr Arg Gln Ala Arg Gln Leu Asn Glu Tyr Ile Phe Pro Lys His Arg
            100                 105                 110

Phe Arg Asn His Leu Val Asp Glu Gly Lys Ile Pro Leu Val Leu Val
        115                 120                 125

Ala Cys Gly Ser Phe Ser Pro Ile Thr Tyr Leu His Leu Arg Met Phe
130                 135                 140

Glu Met Ala Thr Asp Thr Ile Gln Glu Gln Thr Asn Met Glu Leu Val
145                 150                 155                 160

Ala Gly Tyr Phe Ser Pro Val Asn Asp His Tyr Lys Lys Glu Gly Leu
                165                 170                 175

Ala Pro Ala Tyr His Arg Val Arg Met Cys Glu Leu Ala Cys Glu Arg
            180                 185                 190

Thr Ser Ser Trp Leu Met Val Asp Ala Trp Glu Ser Leu Gln Pro Ser
        195                 200                 205

Tyr Thr Cys Thr Ala Arg Val Leu Asp His Phe Asp Glu Glu Ile Asn
    210                 215                 220

Gln Lys Arg Gly Gly Ile Thr Leu Ser Asp Gly Thr Lys Arg Pro Cys
225                 230                 235                 240
```

-continued

```
Lys Ile Met Leu Leu Ala Gly Asp Leu Ile Ala Ser Met Gly Glu
            245                 250                 255

Pro Gly Val Trp Ser Asp Lys Asp Leu His His Ile Leu Gly Lys Phe
        260                 265                 270

Gly Cys Cys Ile Val Glu Arg Thr Gly Ser Asp Val Trp Ala Phe Leu
        275                 280                 285

Leu Ala His Asp Ile Met Phe Ala Tyr Arg Gly Asn Ile Leu Val Ile
        290                 295                 300

Lys Gln Leu Ile Tyr Asn Asp Ile Ser Ser Thr Lys Val Arg Leu Phe
305                 310                 315                 320

Ile Arg Arg Gly Met Ser Ile Arg Tyr Leu Leu Pro Asn Ser Val Ile
                325                 330                 335

Gln Tyr Ile Glu Arg Tyr Ala Leu Tyr Arg Asp Ala Glu Pro Val Lys
                340                 345                 350

Thr Ile Phe Tyr Gln Ser Pro Phe Val Arg Met Glu Pro
                355                 360                 365

<210> SEQ ID NO 38
<211> LENGTH: 584
<212> TYPE: PRT
<213> ORGANISM: Ustilago maydis

<400> SEQUENCE: 38

Met Pro Arg Met Thr Asp Ser Gln Ala Gly Pro Gly Gly Pro Ser Ser
1               5                   10                  15

Leu Lys Phe Ala Ala Leu Ser Val Gln Ser Phe His Leu Asp Ser Pro
            20                  25                  30

Pro Phe Thr Gly Ala Ala Val Gly Gly Ala Gly Pro Leu Asp Glu Ala
        35                  40                  45

Gly Lys Arg Leu Ala Ser His Asp Ala Asp Pro Ala Tyr His Ser Leu
    50                  55                  60

Asp Ser Gly Tyr Ser Gln His Gln Pro Gln Ser Pro Ala Cys Asn Asp
65                  70                  75                  80

Arg Gln Ser Arg Arg Pro Gly Gly Ser Ser Pro Leu Ser Lys Ala Ile
                85                  90                  95

Ser Val Thr Ser Ser Gly Glu Asp His Asp Pro Tyr Arg Arg Ser Met
            100                 105                 110

Ser Gln Thr Arg Pro Pro Ser Gln Ser Gln Thr Leu Arg Ser Gln Asp
        115                 120                 125

Arg Gln His Asn Thr Asp Val Lys Ser Ser Met Ala Gln Pro Gln Ser
    130                 135                 140

Leu Pro Pro Asn Gly Met Thr Thr Ser Glu Asp Ala Pro Ser Ala Ser
145                 150                 155                 160

Asn His Ser Asp Pro His Arg Ser Asn Asp Asn Gly His Leu Glu
                165                 170                 175

Ser Arg Phe Asp Arg Asp Val Pro His Trp Asp Leu Asp Glu Lys Leu
            180                 185                 190

Ser Ser Arg Gln Ala Ser Ser Ala Ser Leu Ala Thr Leu Ser Pro Asp
        195                 200                 205

Lys Pro Ile Met Arg Leu Ser Ser Thr Glu Thr Ser Ser Ala Val Asp
    210                 215                 220

Arg Pro Gly Thr Arg Arg Ser Asp Asp Phe Gln Thr Gly Ser Asn Arg
225                 230                 235                 240

Glu Thr Leu Ile Ala Pro Asn Pro Ser Ser His Arg Thr Asn Ser Asn
                245                 250                 255
```

```
Ser Thr Ser Asn Ser Arg Thr Leu Ser Phe Ser Ala Val Leu Asp Glu
            260                 265                 270

Arg Pro Ser Tyr Ser Gln Phe Ser Glu Asp Leu Asp Ala Gln Glu Asp
            275                 280                 285

Ala Ala Ser Ser Ala Ala Asp Arg Asp Glu Glu Val Asp Gly Pro Glu
290                 295                 300

Gly Leu Ser Ala Glu Phe Arg Leu Arg Asp Arg Val Pro Gln Gln
305                 310                 315                 320

Gly Gln Thr Gln Glu Asp Tyr Ser Phe Pro Arg His Arg Leu Pro Thr
                325                 330                 335

Arg Met Arg Asp Glu Ser Lys Thr Pro Leu Val Val Ala Cys Gly
            340                 345                 350

Ser Phe Ser Pro Pro Thr Tyr Leu His Met Arg Ile Phe Glu Met Ala
            355                 360                 365

Lys Asp Gln Ile Ile Glu Ser Gly Lys Tyr Glu Leu Leu Ala Gly Tyr
            370                 375                 380

Tyr Ser Pro Val Ser Asp Tyr Tyr Lys Lys Glu Gly Leu Ala Lys Ala
385                 390                 395                 400

Thr His Arg Val Arg Met Cys Glu Leu Ala Val Glu Lys Thr Ser Thr
                405                 410                 415

Trp Leu Met Val Asp Ala Trp Glu Ser Leu Gln Asp Glu Tyr Gln Arg
            420                 425                 430

Thr Ala Val Val Leu Asp His Phe His Asp Glu Ile Asn Gly Ser Ser
                435                 440                 445

Asn Gly Gly Val Leu Leu Gly Asp Gly Thr Arg Lys Asn Val Lys Ile
            450                 455                 460

Met Leu Leu Ala Gly Gly Asp Leu Ile Gln Ser Met Gly Glu Pro Gly
465                 470                 475                 480

Val Trp Ala Thr Ala Asp Leu His His Ile Leu Gly Gln Tyr Gly Cys
                485                 490                 495

Leu Ile Val Glu Arg Thr Gly Ala Asp Val Trp Ser Phe Leu Leu Ser
            500                 505                 510

His Asp Leu Leu Trp Lys Tyr Arg Arg Asn Leu Lys Ile Val Lys Gln
            515                 520                 525

Thr Ile Tyr Asn Asp Ile Ser Ser Ser Lys Ile Arg Leu Phe Val Arg
            530                 535                 540

Arg Gly Gln Ser Ile Lys Tyr Leu Leu Pro Asn Ser Val Ile Gln Tyr
545                 550                 555                 560

Ile Glu Lys Glu Gly Leu Tyr Arg Leu Pro Pro Asp Glu Asp Leu Lys
                565                 570                 575

Ser Asp Ser Glu His Ala Asn Trp
            580

<210> SEQ ID NO 39
<211> LENGTH: 537
<212> TYPE: PRT
<213> ORGANISM: Cryptococcus neoformans

<400> SEQUENCE: 39

Met Thr Arg Val Ser Ile Leu Ser Leu Leu Ser Ser Leu Leu Thr Leu
1               5                   10                  15

Leu Ser Pro Pro Phe Gly Gly Thr Ala Thr Ser Glu Met Pro Asp Val
            20                  25                  30

Pro Ser Leu Ser Leu Glu Pro Gln Gln His Ser Arg Pro Val Leu Ser
        35                  40                  45
```

-continued

```
Thr Asn Pro Ser Ala Arg Gln Gln Gly Pro Ala Arg Thr Ala Ser Asn
     50                  55                  60
Thr Ser Gln Thr Ile Ser Asn Pro Glu Pro Val Ser Ser Gly Thr Arg
 65                  70                  75                  80
Glu Thr Pro Ser Lys Ala Ile Ser Ser Leu Lys Ser Ile Gln Pro Pro
                 85                  90                  95
Thr Pro Pro Val Pro Ile Thr Ser Asp Asp Glu Leu Ser Ser Thr Arg
             100                 105                 110
Ser Arg Arg Leu Ile Ser Gly Tyr Leu Phe Gly Asn Pro Pro Ser Pro
         115                 120                 125
Thr Cys Thr Gly Pro Glu Thr Ser Pro Val Thr Ala Ala Ser His Thr
     130                 135                 140
Ser Thr Ala Glu Glu Ser Arg Asp Pro Met Met Ser Arg Lys Phe Ser
145                 150                 155                 160
Pro Thr Leu Glu Lys Ala Arg Asp Val Glu Asn Arg Met Ala Glu Glu
                165                 170                 175
Leu Asp Ser Pro Pro Leu Thr Asp Ser Gln Ile Asp Pro Arg Asp
                180                 185                 190
Ala Leu Glu Met Asp Ser Thr Pro Pro Pro Ser Leu Glu Ser Pro
         195                 200                 205
Lys Pro Ala Asn Ser Asp Leu Val Ser Met Asn Glu Pro Leu Ser Ser
    210                 215                 220
Asp Val Gly Ala Gly Glu Ala Lys Val Lys Gly Arg Lys Ser Glu Arg
225                 230                 235                 240
Ala Arg Lys Arg Glu Thr Gly Tyr Asp Ala Leu Glu Gly Arg Asn Asp
                245                 250                 255
Gly Glu Ala Asp Leu Asp Leu Asn Ala Pro Gln Ala Glu Gly Gly Gly
            260                 265                 270
Ser Gly Ala Tyr Leu Ala Gly Lys Ala Glu Tyr Arg Phe Pro Arg His
         275                 280                 285
Arg Leu Arg Thr Lys Met His Asp Glu Asn Lys Ile Pro Leu Val Ile
    290                 295                 300
Val Ala Cys Gly Ser Phe Ser Pro Pro Thr Tyr Leu His Leu Arg Met
305                 310                 315                 320
Phe Glu Met Ala Lys Asp Glu Ile Val Glu Ser Gln Thr Tyr Glu Ile
                325                 330                 335
Met Ala Gly Tyr Tyr Ser Pro Val Ser Ser Tyr Tyr Lys Lys Ser Gly
            340                 345                 350
Leu Ala Pro Ala Pro His Arg Val Arg Met Cys Glu Leu Ala Val Glu
         355                 360                 365
His Thr Ser Thr Trp Leu Met Val Asp Pro Trp Glu Ala Gly Gln Pro
    370                 375                 380
Glu Tyr Gln Arg Thr Ala Phe Val Leu Asp His Phe Asp Glu Met Leu
385                 390                 395                 400
Asn Gly Gly Glu His Gly Lys Gly Gly Leu Val Met Arg Asp Gly Thr
                405                 410                 415
Arg Arg Arg Tyr Lys Ile Met Leu Leu Ala Gly Gly Asp Leu Ile Glu
            420                 425                 430
Ser Phe Gly Glu Pro Gly Val Trp Ser Glu Pro Asp Leu His Val Ile
         435                 440                 445
Leu Gly Arg Phe Gly Cys Leu Ile Val Glu Arg Ala Gly Ser Asp Val
    450                 455                 460
Trp Ala Phe Leu Leu Ser His Asp Ile Leu Tyr His His Arg Arg Asn
465                 470                 475                 480
```

Val Val Val Ile Lys Gln Leu Ile Tyr Asn Asp Ile Ser Ser Thr Lys
            485                 490                 495

Val Arg Leu Phe Val Arg Arg Gly Met Ser Ile Lys Tyr Leu Leu Pro
        500                 505                 510

Asn Ser Val Ile Gln Tyr Ile Gln Asp Asn Lys Leu Tyr His Gly Ser
            515                 520                 525

Asp Pro Lys Gly Met Ile Gly Lys His
    530                 535

<210> SEQ ID NO 40
<211> LENGTH: 287
<212> TYPE: PRT
<213> ORGANISM: Aspergillus oryzae

<400> SEQUENCE: 40

Met Thr Asp Ile Thr Gly Gly His Gly Glu Asp Val His Gln Pro Pro
1               5                   10                  15

Ala His Ile Pro Pro Ala Pro Met Glu Asp Tyr Gln Phe Pro Glu Leu
            20                  25                  30

Arg Leu Lys Arg Lys Met Asp Asp Pro Glu Lys Thr Pro Leu Leu Leu
        35                  40                  45

Val Ala Cys Gly Ser Phe Ser Pro Ile Thr Tyr Leu His Leu Arg Met
    50                  55                  60

Phe Glu Met Ala Ala Asp Tyr Val Lys Phe Ser Ser Asn Phe Glu Leu
65                  70                  75                  80

Ile Gly Gly Tyr Leu Ser Pro Val Ser Asp Ala Tyr Arg Lys Ala Gly
                85                  90                  95

Leu Ala Ala Ala Glu His Arg Val Ala Met Cys Gln Leu Ala Val Glu
            100                 105                 110

Gln Thr Ser Asp Trp Leu Met Val Asp Thr Trp Glu Pro Met Gln Lys
        115                 120                 125

Ala Tyr Gln Pro Thr Ala Val Val Leu Asp His Phe Asp His Glu Ile
    130                 135                 140

Asn Thr Val Arg Glu Gly Ile Glu Ala Ala Asp Gly Thr Arg Lys His
145                 150                 155                 160

Val Arg Ile Ala Leu Leu Ala Gly Ala Asp Leu Ile His Thr Met Ser
                165                 170                 175

Thr Pro Gly Val Trp Ser Glu Lys Asp Leu Asp His Ile Leu Gly Lys
            180                 185                 190

Tyr Gly Ser Phe Ile Val Glu Arg Ser Gly Thr Asp Ile Asp Glu Ala
        195                 200                 205

Leu Ala Leu Gln Pro Trp Lys Asp Asn Ile His Val Ile Gln Gln
    210                 215                 220

Leu Ile Gln Asn Asp Val Ser Ser Thr Lys Ile Arg Leu Phe Leu Arg
225                 230                 235                 240

Arg Glu Met Ser Val Arg Tyr Leu Ile Pro Val Pro Val Ile Arg Tyr
                245                 250                 255

Ile Glu Gln His Arg Leu Tyr Gly Asp Asp Asn Thr Thr Ala Asn Ser
            260                 265                 270

Thr Ser Asp Lys Gly Lys Gly Lys Gln Glu Pro Ser Lys Ser Gly
        275                 280                 285

<210> SEQ ID NO 41
<211> LENGTH: 288
<212> TYPE: PRT
<213> ORGANISM: Aspergillus fumigatus

<400> SEQUENCE: 41

Met Thr Asp Met Val Gly Gly Gln Ser Asp Asp Val His Gln Val Pro
1               5                   10                  15

Pro Pro Leu Pro Pro Ala Pro Met Glu Asn Tyr Thr Phe Pro Glu His
            20                  25                  30

Arg Leu Lys Arg Lys Met Asp Asp Pro Glu Lys Thr Pro Leu Leu Leu
            35                  40                  45

Val Ala Cys Gly Ser Phe Ser Pro Ile Thr Tyr Leu His Leu Arg Met
50                  55                  60

Phe Glu Met Ala Ala Asp Tyr Val Lys Phe Ser Thr Asp Phe Glu Leu
65                  70                  75                  80

Ile Gly Gly Tyr Leu Ser Pro Val Ser Asp Ala Tyr Arg Lys Ala Gly
                85                  90                  95

Leu Ala Ser Ala Glu His Arg Val Ala Met Cys Gln Leu Ala Val Asp
                100                 105                 110

Gln Thr Ser Asn Trp Leu Met Val Asp Thr Trp Glu Pro Met Gln Lys
            115                 120                 125

Glu Tyr Gln Pro Thr Ala Val Val Leu Asp His Phe Asp Tyr Glu Ile
130                 135                 140

Asn Val Val Arg Glu Gly Ile Asp Ala Gly Asn Gly Thr Arg Lys Pro
145                 150                 155                 160

Val Arg Val Ala Leu Leu Ala Gly Ala Asp Leu Ile His Thr Met Ser
                165                 170                 175

Thr Pro Gly Val Trp Ser Glu Lys Asp Leu Asp His Ile Leu Gly Lys
            180                 185                 190

Tyr Gly Ser Phe Ile Val Glu Arg Ser Gly Thr Asp Ile Asp Glu Ala
        195                 200                 205

Leu Ala Ala Leu Gln Pro Trp Lys Asp Asn Ile Tyr Val Ile Gln Gln
    210                 215                 220

Leu Ile Gln Asn Asp Val Ser Ser Thr Lys Ile Arg Leu Phe Leu Arg
225                 230                 235                 240

Arg Glu Met Ser Val Arg Tyr Leu Ile Pro Val Pro Val Ile His Tyr
                245                 250                 255

Ile Glu Gln His His Leu Tyr Glu Asp Asp Ser Thr Thr Thr Ala Ser
            260                 265                 270

Ser Ser Ala Asp Lys Gly Lys Glu Pro Ser Gln Pro Gly Lys Ser Gly
        275                 280                 285

<210> SEQ ID NO 42
<211> LENGTH: 285
<212> TYPE: PRT
<213> ORGANISM: Aspergillus nidulans

<400> SEQUENCE: 42

Met Thr Glu Ser Thr Gln Glu Gln Gly Asn Asp Gly Gln Arg Met Pro
1               5                   10                  15

Pro Ala Pro Ala Thr Pro Val Asp Tyr Val Phe Pro Glu Tyr Arg
            20                  25                  30

Leu Lys Arg Val Met Asp Asp Pro Glu Lys Thr Pro Leu Leu Leu Ile
            35                  40                  45

Ala Cys Gly Ser Phe Ser Pro Ile Thr Phe Leu His Leu Arg Met Phe
50                  55                  60

Glu Met Ala Ala Asp Tyr Val Lys Leu Ser Thr Asp Phe Glu Ile Ile
65                  70                  75                  80

```
Gly Gly Tyr Leu Ser Pro Val Ser Asp Ala Tyr Arg Lys Ala Gly Leu
                85                  90                  95

Ala Ser Ala Asn His Arg Ile Ala Met Cys Gln Arg Ala Val Asp Gln
            100                 105                 110

Thr Ser Asp Trp Met Met Val Asp Thr Trp Glu Pro Met His Lys Glu
        115                 120                 125

Tyr Gln Pro Thr Ala Ile Val Leu Asp His Phe Asp Tyr Glu Ile Asn
    130                 135                 140

Thr Val Arg Lys Gly Ile Asp Thr Gly Lys Gly Thr Arg Lys Arg Val
145                 150                 155                 160

Gln Val Val Leu Leu Ala Gly Ala Asp Leu Val His Thr Met Ser Thr
                165                 170                 175

Pro Gly Val Trp Ser Glu Lys Asp Leu Asp His Ile Leu Gly Gln Tyr
            180                 185                 190

Gly Thr Phe Ile Val Glu Arg Ser Gly Thr Asp Ile Asp Glu Ala Leu
        195                 200                 205

Ala Ala Leu Gln Pro Trp Lys Lys Asn Ile His Val Ile Gln Gln Leu
    210                 215                 220

Ile Gln Asn Asp Val Ser Ser Thr Lys Ile Arg Leu Phe Leu Arg Arg
225                 230                 235                 240

Asp Met Ser Val Arg Tyr Leu Ile Pro Asp Pro Val Ile Glu Tyr Ile
                245                 250                 255

Tyr Glu Asn Asn Leu Tyr Met Asp Asp Gly Thr Thr Gln Pro Thr Ala
            260                 265                 270

Asp Lys Gly Lys Thr Arg Glu Pro Ala Pro Ser Asn
        275                 280                 285

<210> SEQ ID NO 43
<211> LENGTH: 276
<212> TYPE: PRT
<213> ORGANISM: Giberella zeae

<400> SEQUENCE: 43

Met Ala Cys Asp Tyr Gln Tyr Val Lys Glu His Thr Arg Glu Asp Tyr
1               5                   10                  15

Val Phe Pro Ser His Arg Phe Gln Arg Ser Cys Ser Pro Asp Lys Thr
                20                  25                  30

Pro Leu Cys Leu Val Ala Cys Gly Ser Phe Ser Pro Ile Thr Phe Leu
            35                  40                  45

His Leu Arg Met Phe Pro Met Ala Arg Asp His Ala Arg Asn Glu Asp
        50                  55                  60

Phe Glu Val Val Ala Gly Val Leu Ser Pro Val Ser Asp Ala Tyr Lys
65                  70                  75                  80

Lys Lys Gly Leu Ala Pro Ala His His Arg Ile Glu Met Cys Arg Leu
                85                  90                  95

Ala Thr Glu Asn Thr Ser Lys Trp Leu Met Val Asp Pro Trp Glu Ala
            100                 105                 110

Glu Ser Pro Thr Tyr Ile Pro Thr Ala Lys Val Leu Asp His Phe Asp
        115                 120                 125

Tyr Glu Ile Asn Glu Val Met Gly Gly Val Glu Cys Thr Asp Gly Thr
    130                 135                 140

Arg Lys Arg Cys Arg Ile Val Leu Leu Ala Gly Leu Asp Leu Ile Gln
145                 150                 155                 160

Thr Met Ser Thr Pro Gly Val Trp Asp Glu Arg Asp Leu Asp His Ile
                165                 170                 175
```

```
Leu Gly Asn Tyr Gly Val Phe Ala Leu Glu Arg Thr Gly Thr Glu Ile
            180                 185                 190

Asp Ser Thr Leu Ala Asn Leu Lys Gln Trp Glu Lys Asn Ile His Ile
        195                 200                 205

Ile Arg Gln Val Val Thr Asn Asp Ile Ser Ser Thr Lys Ile Arg Leu
210                 215                 220

Leu Leu Lys Arg Asn Met Ser Ile Asp Phe Leu Ile Pro Asp Asp Val
225                 230                 235                 240

Ile Ser Tyr Ile Tyr Glu His Asn Leu Tyr Arg Asp Leu Asp Met Pro
                245                 250                 255

Asp Ser Lys Gly Lys Glu Lys Ala Leu Thr Asn Gly Pro Asp Ala Gly
                260                 265                 270

Thr Ser Thr Gly
            275

<210> SEQ ID NO 44
<211> LENGTH: 317
<212> TYPE: PRT
<213> ORGANISM: Neurospora crassa

<400> SEQUENCE: 44

Met Ser Ser Gln Thr Ser Thr Gly Met Ala Thr Pro Val Thr Tyr Pro
1               5                   10                  15

Pro Pro Glu Gln Ala Ser Thr Gly Asn Thr Thr Val Pro Tyr Thr Phe
            20                  25                  30

Pro Gln Ala Lys Leu Lys Leu Gln Gln Thr Gln Pro Gly Arg Thr Pro
        35                  40                  45

Leu Val Leu Val Ala Cys Gly Ser Phe Ser Pro Ile Thr Phe Leu His
50                  55                  60

Leu Arg Met Phe Glu Met Ala Ser Asp Phe Val Arg Phe Asn Thr Asn
65                  70                  75                  80

Phe Glu Val Cys Gly Gly Tyr Leu Ser Pro Val Ser Asp Ala Tyr Lys
                85                  90                  95

Lys Ala Gly Leu Ala Pro Gly His His Arg Val Glu Met Cys Ser Arg
            100                 105                 110

Ala Val Glu His Ser Ser Trp Leu Met Val Asp Pro Phe Glu Thr Val
        115                 120                 125

Asn Cys Asp Glu Asn Gly Glu Pro Ala Tyr Val Pro Thr Ala Arg Val
130                 135                 140

Leu Arg His Phe Asp His Glu Ile Asn Thr Val Leu Gly Gly Ile Glu
145                 150                 155                 160

Gly Thr Asp Gly Val Arg Arg Lys Ala Lys Ile Ala Leu Leu Ala Gly
                165                 170                 175

Ala Asp Leu Val Met Ser Met Gly Glu Pro Gly Leu Trp Ser Pro Val
            180                 185                 190

Asp Leu Gly Val Ile Leu Gly Glu Tyr Gly Ala Phe Ile Ile Glu Arg
        195                 200                 205

Ser Gly Thr Asp Ile Asp Glu Ala Leu Ala Thr Leu Arg Gln Tyr Glu
210                 215                 220

Asp Asn Ile Trp Val Ile Ser Gln Val Ile Gln Asn Asp Ile Ser Ser
225                 230                 235                 240

Thr Lys Val Arg Leu Phe Leu Lys Lys Asp Leu Ser Val Arg Tyr Leu
                245                 250                 255

Ile Pro Asp Pro Val Val Glu Tyr Ile Glu Glu His Gly Leu Phe Gln
            260                 265                 270
```

```
Asp Glu Gln Ser Ser Lys Lys Asn Asn Asp Thr Ser Ser Thr Gly
        275                 280                 285

Gly Lys Asp Lys Glu Lys Glu Lys Pro Thr Thr Ala Asp Gly Thr Ser
290                 295                 300

Thr Pro Ser Ser Thr Glu Glu Thr Thr Gln Gln Ser
305                 310                 315

<210> SEQ ID NO 45
<211> LENGTH: 292
<212> TYPE: PRT
<213> ORGANISM: Magnaporthe grisea

<400> SEQUENCE: 45

Met Ser Asn Ala Thr Ser Pro Thr Pro Gln Phe Pro Pro Thr Thr Pro
1               5                   10                  15

Gly Tyr Thr Phe Pro Val Asp Lys Leu Arg Thr Arg Gln Thr Gln Asn
            20                  25                  30

Glu Arg Thr Pro Leu Val Leu Val Ala Cys Gly Ser Phe Ser Pro Ile
        35                  40                  45

Thr Tyr Leu His Leu Arg Met Phe Glu Met Ala Arg Ala Gly Pro Ala
50                  55                  60

Asp Asn Arg Thr Gly Asp His Cys Ser Leu Asn Thr Asn Phe Glu Val
65                  70                  75                  80

Val Gly Gly Tyr Ile Ser Pro Val Ser Asp Ala Tyr Lys Lys Ala Gly
                85                  90                  95

Leu Ala Pro Ala His His Arg Ile Asn Met Cys Lys Leu Ser Leu Ala
            100                 105                 110

Ser Ser Ser Trp Ile Met Val Asp Glu Tyr Glu Thr Ser Val Arg Asn
        115                 120                 125

Pro Thr Thr Asn Glu Pro Ala Tyr Thr Pro Thr Ala Gln Val Leu Ala
    130                 135                 140

Lys Leu Asp His Glu Ile Asn Thr Val Leu Gly Gly Ile Gln Ser Ala
145                 150                 155                 160

Asp Asp Pro Asn Lys Arg Thr Arg Ala Arg Ile Cys Leu Leu Ala Gly
                165                 170                 175

Gly Asp Leu Val Leu Thr Met Ser Thr Pro Gly Leu Trp Ala Pro Ser
            180                 185                 190

Asp Leu Asp Val Ile Leu Gly Pro Lys Phe Gly Ala Phe Ile Val Glu
        195                 200                 205

Arg Ser Gly Thr Asp Thr Glu Glu Ala Leu Ala Ser Leu Gln Arg Tyr
    210                 215                 220

Lys Asp Asn Ile Trp Val Ile Pro Gln Val Ile Gln Asn Asp Val Ser
225                 230                 235                 240

Ser Thr Lys Ile Arg Leu Phe Leu Lys Lys Asn Leu Ser Ile Arg Tyr
                245                 250                 255

Leu Ile Pro Asp Pro Val Val Arg Tyr Ile Glu His Gly Leu Phe
            260                 265                 270

Asn Gly Glu Phe Ser Gly Ala Ser Ser Ser Lys Glu Ala Glu Pro Ser
        275                 280                 285

Pro Ser Thr Ala
    290

<210> SEQ ID NO 46
<211> LENGTH: 120
<212> TYPE: PRT
<213> ORGANISM: Ustilago maydis
```

-continued

```
<400> SEQUENCE: 46

Met Leu Leu Ala Gly Gly Asp Leu Ile Gln Ser Met Gly Glu Pro Gly
1               5                   10                  15

Val Trp Ala Thr Ala Asp Leu His His Ile Leu Gly Gln Tyr Gly Cys
            20                  25                  30

Leu Ile Val Glu Arg Thr Gly Ala Asp Val Trp Ser Phe Leu Leu Ser
        35                  40                  45

His Asp Leu Leu Trp Lys Tyr Arg Arg Asn Leu Lys Ile Val Lys Gln
50                  55                  60

Thr Ile Tyr Asn Asp Ile Ser Ser Lys Ile Arg Leu Phe Val Arg
65                  70                  75                  80

Arg Gly Gln Ser Ile Lys Tyr Leu Leu Pro Asn Ser Val Ile Gln Tyr
            85                  90                  95

Ile Glu Lys Glu Gly Leu Tyr Arg Leu Pro Pro Asp Glu Asp Leu Lys
        100                 105                 110

Ser Asp Ser Glu His Ala Asn Trp
        115                 120

<210> SEQ ID NO 47
<211> LENGTH: 225
<212> TYPE: PRT
<213> ORGANISM: Chaetomium globosum

<400> SEQUENCE: 47

Met Thr Ala Gly Thr Ile Asn Ser Asp Thr Gln Thr Pro Thr Ala Met
1               5                   10                  15

Gly Pro Ala Val Asp Gly Ala Gln Ala Pro Tyr Asn Phe Pro Thr Gln
            20                  25                  30

Lys Leu Lys Arg Gln Met Thr Gln Pro Gly Lys Thr Pro Leu Val Leu
        35                  40                  45

Val Ala Cys Gly Ser Phe Ser Pro Ile Thr Tyr Leu His Leu Arg Met
    50                  55                  60

Phe Glu Met Ala Gly Asp Phe Val Arg Phe Asn Thr Asp Phe Glu Val
65                  70                  75                  80

Cys Ala Gly Tyr Leu Ser Pro Val Ser Asp Ala Tyr Lys Lys Val Gly
            85                  90                  95

Leu Ala Pro Gly Ser His Arg Val Asn Met Cys Gly Arg Ala Val Glu
        100                 105                 110

Gln Ser Pro Trp Leu Met Val Asp Pro Phe Glu Thr Val Asn Cys Asp
        115                 120                 125

Glu Asn Gly Glu Pro Gln Tyr Val Pro Thr Ala Lys Val Leu Arg His
130                 135                 140

Phe Asp His Glu Ile Asn Thr Val Leu Gly Gly Ile Glu Ala Pro Asp
145                 150                 155                 160

Gly Gln Met Lys Lys Ala Arg Ile Ala Leu Leu Ala Gly Ala Asp Leu
            165                 170                 175

Val Met Ser Met Gly Gly Phe Asp Thr Gly Ser Arg Val Ser Asn Val
        180                 185                 190

Lys Leu Thr Cys Thr Arg Gly Ala Trp Ala Leu Gly Ser Lys Gly Ser
    195                 200                 205

Gly His Asp Pro Arg Val Val Arg Phe His His Arg Ala Leu Gly
        210                 215                 220

Asp
225
```

-continued

```
<210> SEQ ID NO 48
<211> LENGTH: 426
<212> TYPE: PRT
<213> ORGANISM: Saccharomyces cerevisae

<400> SEQUENCE: 48

Met Ser Glu Pro Val Ile Lys Ser Leu Leu Asp Thr Asp Met Tyr Lys
1               5                   10                  15

Ile Thr Met His Ala Ala Val Phe Thr Asn Phe Pro Asp Val Thr Val
            20                  25                  30

Thr Tyr Lys Tyr Thr Asn Arg Ser Ser Gln Leu Thr Phe Asn Lys Glu
        35                  40                  45

Ala Ile Asn Trp Leu Lys Glu Gln Phe Ser Tyr Leu Gly Asn Leu Arg
    50                  55                  60

Phe Thr Glu Glu Ile Glu Tyr Leu Lys Gln Glu Ile Pro Tyr Leu
65                  70                  75                  80

Pro Ser Ala Tyr Ile Lys Tyr Ile Ser Ser Asn Tyr Lys Leu His
            85                  90                  95

Pro Glu Glu Gln Ile Ser Phe Thr Ser Glu Glu Ile Glu Gly Lys Pro
        100                 105                 110

Thr His Tyr Lys Leu Lys Ile Leu Val Ser Gly Ser Trp Lys Asp Thr
    115                 120                 125

Ile Leu Met Arg Ser Leu Thr Val Leu Ile Ser Glu Ala Tyr Leu Ile
130                 135                 140

Val Thr Ser Thr Gly Leu Arg Asn His Arg Gln Ala Glu Lys Lys Ala
145                 150                 155                 160

Glu Thr Leu Phe Asp Asn Gly Ile Arg Phe Arg Ile His Gly Thr Arg
                165                 170                 175

Arg Arg Arg Ser Leu Lys Ala Gln Asp Leu Ile Met Gln Gly Ile Met
            180                 185                 190

Lys Ala Val Asn Gly Asn Pro Asp Arg Asn Lys Ser Leu Leu Leu Gly
        195                 200                 205

Thr Ser Asn Ile Leu Phe Ala Lys Lys Tyr Gly Val Lys Pro Ile Gly
    210                 215                 220

Thr Val Ala His Glu Trp Val Met Gly Val Ala Ser Ile Ser Glu Leu
225                 230                 235                 240

Asp Tyr Leu His Ala Asn Lys Asn Ala Met Asp Cys Trp Ile Asn Thr
                245                 250                 255

Phe Gly Ala Lys Asn Ala Gly Leu Ala Leu Thr Asp Thr Phe Gly Thr
            260                 265                 270

Asp Asp Phe Leu Lys Ser Phe Arg Pro Pro Tyr Ser Asp Ala Tyr Val
        275                 280                 285

Gly Val Arg Gln Asp Ser Gly Asp Pro Val Glu Tyr Thr Lys Lys Ile
    290                 295                 300

Ser His His Tyr His Asp Val Leu Lys Leu Pro Lys Phe Ser Lys Ile
305                 310                 315                 320

Ile Cys Tyr Ser Asp Ser Leu Asn Val Glu Lys Ala Ile Thr Tyr Ser
                325                 330                 335

His Ala Ala Lys Glu Asn Gly Met Leu Ala Thr Phe Gly Ile Gly Thr
            340                 345                 350

Asn Phe Thr Asn Asp Phe Arg Lys Lys Ser Glu Pro Gln Val Lys Ser
        355                 360                 365

Glu Pro Leu Asn Ile Val Ile Lys Leu Leu Glu Val Asn Gly Asn His
    370                 375                 380

Ala Ile Lys Ile Ser Asp Asn Leu Gly Lys Asn Met Gly Asp Pro Ala
```

```
              385                 390                 395                 400
Thr Val Lys Arg Val Lys Glu Glu Leu Gly Tyr Thr Glu Arg Ser Trp
                    405                 410                 415

Ser Gly Asp Asn Glu Ala His Arg Trp Thr
                420                 425

<210> SEQ ID NO 49
<211> LENGTH: 431
<212> TYPE: PRT
<213> ORGANISM: Candida glabrata

<400> SEQUENCE: 49

Met Ser Ser Met Thr Pro Ala Ile Thr Ser Leu Leu Asp Thr Asp Met
1               5                   10                  15

Tyr Lys Ile Thr Met His Ala Ala Val Phe Thr Asn Phe Pro Asp Ala
                20                  25                  30

Arg Val Val Tyr Lys Phe Thr Asn Arg Thr Ala Gln Phe His Phe Asn
            35                  40                  45

Lys Arg Ala Val Asp Trp Ile Lys Glu Gln Phe Arg Leu Leu Gly Asp
    50                  55                  60

Leu Thr Phe Thr His Asp Asp Val Glu Tyr Leu Ala Arg Glu Ile Pro
65                  70                  75                  80

Phe Leu Pro Ala Lys Tyr Leu His Tyr Ile Glu Asn Gly Phe Thr Leu
                85                  90                  95

Lys Pro Asp Glu Gln Ile Glu Leu Asp Cys Gln Glu Ile Lys Gly Lys
            100                 105                 110

Glu Asp Gln Tyr Asp Leu His Ile Leu Val Lys Gly Leu Trp Ile Asp
        115                 120                 125

Thr Ile Leu Tyr Glu Ile Pro Ile Leu Ala Leu Ser Glu Ala Tyr
    130                 135                 140

Phe Lys Phe Val Asp Thr Asp Trp Asp Tyr Glu Asn Gln Leu Ser Asn
145                 150                 155                 160

Ala Lys Glu Lys Ala Leu Arg Leu Phe Glu Asn Asn Leu Ser Phe Ser
                165                 170                 175

Glu Phe Gly Thr Arg Arg Arg Ser Phe Lys Thr Gln Asp Leu Val
            180                 185                 190

Met Glu Gly Ile Met Gln Ala Val Lys Glu Asn Pro Glu Lys Tyr Arg
        195                 200                 205

Pro Leu Leu Leu Gly Thr Ser Asn Ile Leu Phe Ala Lys Lys Tyr Gly
    210                 215                 220

Val Lys Pro Ile Gly Thr Val Ala His Glu Trp Ile Met Gly Ile Ala
225                 230                 235                 240

Ser Ile Thr Gly Asp Tyr Pro Glu Thr Asn Arg Ile Ala Met Asp Tyr
                245                 250                 255

Trp Ile Lys Thr Phe Gly Lys Glu His Ala Gly Leu Ala Leu Thr Asp
            260                 265                 270

Thr Phe Gly Thr Asp Asp Phe Leu Lys Ser Phe Lys Pro Pro Tyr Ser
        275                 280                 285

Asp Tyr Tyr Ile Gly Val Arg Gln Asp Ser Gly Asp Pro Ile Lys Tyr
    290                 295                 300

Thr Glu Lys Ile Ala His His Phe His Asp Val Leu Lys Leu Pro Lys
305                 310                 315                 320

Phe Ser Lys Phe Ile Cys Tyr Ser Asp Ser Leu Asn Ile Asp Lys Ala
                325                 330                 335

Ile Glu Tyr Gly Lys Val Ala Glu Ala His Gly Ile Lys Ser Thr Phe
```

```
                    340                 345                 350
Gly Ile Gly Thr Asn Phe Thr Asn Asp Phe His Lys Lys Ser Asp Pro
            355                 360                 365

Ser Val Lys Ser Ala Pro Leu Asn Ile Val Ile Lys Leu Leu Glu Val
            370                 375                 380

Asn Gly Asn His Ser Ile Lys Ile Ser Asp Asn Ala Gly Lys Asn Met
385                 390                 395                 400

Gly Asp Pro Asp Thr Val Lys Lys Val Lys Glu Gln Leu Gly Tyr Val
            405                 410                 415

Glu Arg Gln Trp Ala Gly Gly Asn Glu Ala His Arg Ser Ala Ala
            420                 425                 430

<210> SEQ ID NO 50
<211> LENGTH: 427
<212> TYPE: PRT
<213> ORGANISM: Kluyveromyces lactis

<400> SEQUENCE: 50

Met Glu Pro Val Ile Thr Ser Phe Leu Asp Thr Asp Met Tyr Lys Leu
1               5                   10                  15

Thr Met His Ala Ala Val Tyr Thr His Phe Lys Asp Val Lys Val Lys
            20                  25                  30

Tyr Lys Tyr Thr Asn Arg Ser Pro Gln Met Thr Phe Asn Lys Glu Ala
            35                  40                  45

Val Glu Trp Leu Lys Gly Gln Phe Leu Leu Leu Ala Asn Ile Arg Leu
            50                  55                  60

Thr Thr Glu Glu Leu Lys Tyr Ile Lys Glu Ala Ile Pro Tyr Leu Pro
65              70                  75                  80

Ala Glu Tyr Leu Glu Phe Ile Ser Asn Gly Gly Phe Glu Val Asn Pro
            85                  90                  95

Lys Asp Glu Ile Lys Phe Glu Ala Arg Glu Ile Glu Gly Pro Gly
            100                 105                 110

His Tyr Glu Leu Asp Ile Ser Ile Glu Gly Leu Trp Ile Lys Thr Ile
            115                 120                 125

Trp Tyr Glu Ile Pro Val Leu Ala Leu Val Ser Glu Ala Tyr Phe Lys
            130                 135                 140

Phe Val Asp Thr Asp Trp Thr Tyr Asp Gly Gln Val Glu Lys Ala Tyr
145                 150                 155                 160

Ala Lys Ala Lys Lys Leu Leu Asp His Asp Ile Val Phe Ser Glu Phe
            165                 170                 175

Gly Thr Arg Arg Arg Ser Phe Lys Thr Gln Asp Leu Val Met Gln
            180                 185                 190

Gly Ile Ile Asn Ala Ala Lys Asp Cys Asp Lys Ser Lys Tyr Val Leu
            195                 200                 205

Gly Thr Ser Asn Val Leu Phe Ala Lys Lys Tyr Asn Val Asn Pro Ile
            210                 215                 220

Gly Thr Val Ala His Glu Trp Met Met Gly Ile Ala Ser Ile Thr Asn
225                 230                 235                 240

Asp Tyr Leu Asn Ala Asn Lys Asn Ala Met Asp Tyr Trp Ile Glu Thr
            245                 250                 255

Phe Gly Met Glu Asn Ala Gly Leu Ala Leu Thr Asp Thr Phe Gly Thr
            260                 265                 270

Asp Ser Phe Leu Lys Ser Phe Tyr Pro Pro Tyr Ser Asp Ala Tyr Ile
            275                 280                 285

Gly Val Arg Gln Asp Ser Gly Asp Pro Ile Leu Tyr Thr Glu Lys Ile
```

```
                290                 295                 300
Ala His His Tyr Asn Asp Val Leu Lys Leu Pro Lys Phe Ser Lys Ile
305                 310                 315                 320

Ile Cys Tyr Ser Asp Ser Leu Asn Pro Asp Arg Ala Ile Glu Tyr Ala
                325                 330                 335

Gln Val Ala His Lys His Gly Leu Lys Ala Thr Phe Gly Ile Gly Thr
                340                 345                 350

Asn Phe Thr Asn Asp Phe Gln Arg Lys Ser Asp Val Ser Val Lys Ser
                355                 360                 365

Glu Pro Leu Asn Ile Val Ile Lys Leu Leu Glu Val Asn Gly Asn His
370                 375                 380

Ala Ile Lys Ile Ser Asp Asn Leu Gly Lys Asn Met Gly Asp Pro Glu
385                 390                 395                 400

Thr Val Arg Arg Val Lys Glu Glu Leu Gly Tyr Val Glu Arg Lys Tyr
                405                 410                 415

Ala Gly Asp Asn Glu Ala His Arg Trp Ala Ala
                420                 425

<210> SEQ ID NO 51
<211> LENGTH: 430
<212> TYPE: PRT
<213> ORGANISM: Eremothecium gossypii

<400> SEQUENCE: 51

Met Thr Ser Glu Glu Ala Ala Ile Lys Ser Leu Leu Asp Thr Asp Met
1               5                   10                  15

Tyr Lys Leu Thr Met His Ala Ala Val Tyr Val Asn Phe Pro Asp Thr
                20                  25                  30

Glu Val Val Tyr Lys Tyr Thr Asn Arg Ser Ala Gly Leu Ser Phe Asn
                35                  40                  45

Lys Ala Ala Ile Val Trp Leu Glu Asp Gln Val Ser Lys Leu Ala Thr
50                  55                  60

Leu Arg Phe Thr Ala Glu Glu Val Ala Tyr Leu Lys Glu Thr Leu Pro
65                  70                  75                  80

Phe Leu Pro Ala Gln Tyr Ile Asp Tyr Ile Ser Ser Pro Glu Cys Arg
                85                  90                  95

Met Asp Pro Ala Thr Gln Val Gln Leu Leu His Glu Gln Arg Glu Gly
                100                 105                 110

Glu Glu Arg Tyr Asp Leu Asn Ile Thr Val Thr Gly Leu Trp Lys Asp
                115                 120                 125

Thr Ile Leu Tyr Glu Ile His Met Leu Ala Leu Ile Ser Glu Ala Tyr
130                 135                 140

Phe Lys Phe Val Asp Thr Asp Trp Val Leu Asp Gly Gln Val Glu Gln
145                 150                 155                 160

Ala Tyr Arg Lys Thr Arg Leu Leu Leu Asp Asn Gly Leu Val Phe Ser
                165                 170                 175

Glu Phe Gly Thr Arg Arg Arg Arg Ser Leu Leu Val Gln Asp Leu Val
                180                 185                 190

Leu Gln Gly Ile Ala Glu Ala Val Ala Asp Ser Gly Thr Gly Asp Thr
                195                 200                 205

Gln Phe Ile Gly Thr Ser Asn Val Tyr Phe Ala Lys Lys Tyr Gly Val
                210                 215                 220

Lys Pro Val Gly Thr Val Ala His Glu Trp Tyr Met Gly Ile Ala Ala
225                 230                 235                 240

Leu Thr Asp Asp Tyr Arg Asn Ala Asn Lys Asn Ala Met Asp Phe Trp
```

```
                  245                 250                 255
Leu Asn Thr Phe Gly Ser Glu Gln Ala Gly Leu Val Leu Thr Asp Thr
                260                 265                 270
Phe Gly Thr Asp Thr Phe Leu Pro Met Phe Arg Pro Pro Tyr Ser Asp
                275                 280                 285
Val Tyr Asp Gly Val Arg Gln Asp Ser Gly Asp Pro Ala Val Phe Thr
                290                 295                 300
Glu Lys Val Ala His His Tyr Leu Asn Val Leu His Tyr Pro Arg Phe
305                 310                 315                 320
Ser Lys Val Ile Cys Tyr Ser Asp Ser Leu Asn Pro Glu Lys Ala Leu
                325                 330                 335
Gln Tyr Ala Glu Val Ala Arg Ala His Gly Met Arg Ala Ser Phe Gly
                340                 345                 350
Ile Gly Thr Asn Phe Thr Asn Asp Phe Arg Arg His Ser Ala Pro Asp
                355                 360                 365
Ala Lys Ser Glu Pro Leu Asn Ile Val Phe Lys Leu Leu Thr Val Asn
                370                 375                 380
Gly Arg Pro Ala Ile Lys Ile Ser Asp Asp Leu Gly Lys Thr Met Gly
385                 390                 395                 400
Asp Pro Glu Lys Val Glu Val Lys Arg Glu Leu Gly Tyr Ile Glu
                405                 410                 415
Arg Thr Trp Glu Gly Ser Asp Glu Ala His Arg Trp Lys Asp
                420                 425                 430

<210> SEQ ID NO 52
<211> LENGTH: 422
<212> TYPE: PRT
<213> ORGANISM: Debaromyces hansenii

<400> SEQUENCE: 52

Met Thr Thr Asp Ile Pro Ile Ile Thr Ser Ile Leu Asp Thr Asp Leu
1               5                   10                  15
Tyr Lys Leu Thr Met His Ala Ala Val Val Lys His Phe Pro Asn Ile
                20                  25                  30
Pro Val Val Tyr Arg Tyr Thr Asn Arg Thr Pro Ser Met Val Leu Asn
                35                  40                  45
Lys Glu Ala Ile Asp Trp Leu Lys Tyr Gln Ile Ser Lys Leu Ser Asp
                50                  55                  60
Leu Arg Val Ser Ser Glu Glu Leu Glu Tyr Leu Arg Lys Ala Leu Pro
65                  70                  75                  80
Gln Met Pro Glu Val Tyr Leu Lys Tyr Leu Glu Thr Phe Gln Leu Phe
                85                  90                  95
Pro Asp Lys Gln Ile Lys Tyr Phe Asn Asp Glu Ser Asn Phe Glu Glu
                100                 105                 110
Phe Glu Ile Glu Met Lys Gly Lys Trp Asp Glu Thr Met Leu Tyr Glu
                115                 120                 125
Ile Pro Leu Leu Ala Leu Ile Ser Glu Ala Tyr Phe Lys Phe Val Asp
                130                 135                 140
Thr Asp Trp Asn Tyr Asp Gly Gln Ala Glu Arg Ala Glu Asp Lys Cys
145                 150                 155                 160
Ala Gln Leu Phe Lys Asn Glu Cys Thr Phe Ser Glu Phe Gly Thr Arg
                165                 170                 175
Arg Arg Arg Ser Phe Lys Thr Gln Asp Leu Val Val Lys Asn Leu Cys
                180                 185                 190
Asp Phe Ala Gly Lys Asn Pro Asp Lys Lys His Phe Leu Gly Thr Ser
```

```
                195                 200                 205
Asn Val Leu Leu Ala Lys Lys Tyr Asn Thr Thr Pro Ile Gly Thr Val
210                 215                 220

Ala His Glu Trp Phe Met Gly Ile Ala Ser Ile Thr Gln Asp Tyr Thr
225                 230                 235                 240

Asn Ala Asn Lys Leu Ala Met Asp Tyr Trp Leu Asp Thr Phe Gly Pro
                245                 250                 255

Glu His Ala Gly Leu Ala Leu Thr Asp Thr Phe Gly Thr Asp Ala Tyr
                260                 265                 270

Leu Lys Val Phe Thr Lys Pro Tyr Thr Asp Tyr Tyr Thr Gly Val Arg
                275                 280                 285

Gln Asp Ser Gly Asp Pro Glu Leu Phe Ala Glu Lys Leu Ala Asp His
290                 295                 300

Tyr Lys Lys Gln Gly Tyr Pro Asp Phe Ser Lys Ile Ile Cys Phe Ser
305                 310                 315                 320

Asp Ser Leu Asn Val Glu Lys Cys Leu Lys Tyr Lys Gln Lys Val Asn
                325                 330                 335

Ser Leu Gly Leu Ile Ala Ser Phe Gly Ile Gly Thr Phe Phe Thr Asn
                340                 345                 350

Asp Phe Ala Ser Val Ser Asp Pro Ser Thr Lys Ser Val Pro Leu Asn
                355                 360                 365

Ile Val Ile Lys Leu Lys Glu Ala Asn Gly Asn Pro Ser Ile Lys Ile
                370                 375                 380

Ser Asp Asn Leu Gly Lys Asn Met Gly Asp Pro Ala Val Val Ser Arg
385                 390                 395                 400

Val Lys Lys Glu Leu Asn Tyr Glu Glu His Ser Trp Ala Gly Asp
                405                 410                 415

Glu Glu Lys Arg Trp Asp
                420

<210> SEQ ID NO 53
<211> LENGTH: 421
<212> TYPE: PRT
<213> ORGANISM: Candida albicans

<400> SEQUENCE: 53

Met Asn Gly Thr Glu Asp Lys Pro Val Ile Lys Ser Phe Leu Asp Thr
1               5                   10                  15

Asp Leu Tyr Lys Leu Phe Met His Ala Ala Val Asn Lys Gln Phe Pro
                20                  25                  30

Asp Val Pro Val Lys Tyr Arg Tyr Thr Asn Arg Thr Pro Gln Leu Lys
            35                  40                  45

Leu Asn Ser Gln Ala Ile Ser Trp Leu Lys Lys Gln Ile Glu Tyr Leu
        50                  55                  60

Gly Asp Leu Arg Phe Ser Ala Glu Glu Ile Leu Tyr Leu His Arg Val
65                  70                  75                  80

Leu Pro Gln Leu Pro Ser Asp Tyr Leu Glu Tyr Leu Ala Asp Phe Lys
                85                  90                  95

Leu Val Pro Ser Ser Gln Ile Lys Tyr Leu Asp Asn Asp Glu Gly Asp
            100                 105                 110

Phe Glu Leu Glu Ile Val Gly Lys Trp Asn Asp Thr Ile Leu Tyr Glu
        115                 120                 125

Ile Pro Leu Leu Ala Leu Val Ser Glu Ala Tyr Phe Lys Phe Val Asp
    130                 135                 140

Thr Asp Trp Asn Tyr Glu Gly Gln Tyr Ala Leu Ala Gln Lys Lys Ala
```

```
                145                 150                 155                 160
Lys Gln Leu Ile Ser Asn Glu Cys Asn Phe Ser Glu Phe Gly Thr Arg
                    165                 170                 175

Arg Arg Arg Ser Tyr Glu Ser Gln Glu Ile Val Ile Lys Ala Ile Lys
                    180                 185                 190

Asp Val Gln Ile Asp Thr Gln Ser Lys Tyr Ile Ala Gly Thr Ser Asn
                    195                 200                 205

Val Tyr Phe Ala Met Lys Tyr Asp Leu Pro Pro Ile Gly Thr Val Ala
    210                 215                 220

His Glu Trp Tyr Met Gly Ile Ala Ser Ile Thr Gln Asp Tyr Val His
225                 230                 235                 240

Ala Asn Lys Leu Ala Met Asp Tyr Trp Ile Asp Thr Phe Gly Ala Lys
                    245                 250                 255

Tyr Ala Gly Leu Ala Leu Thr Asp Thr Phe Gly Thr Asp Asn Tyr Leu
                    260                 265                 270

Thr Met Phe Val Ala Pro Tyr Val Asn Glu Tyr Ser Gly Val Arg Gln
                    275                 280                 285

Asp Ser Gly Asp Pro Glu Leu Tyr Ala Glu Lys Ile Ala Arg His Tyr
                    290                 295                 300

Glu Lys Met Gly Ile Ala Lys Asn Thr Lys Ile Ile Cys Phe Ser Asp
305                 310                 315                 320

Ser Leu Asn Val Glu Lys Cys Leu Lys Tyr Lys Asn Thr Ala Asp Lys
                    325                 330                 335

Leu Gly Leu Ile Ser Thr Phe Gly Ile Gly Thr Phe Phe Thr Asn Asp
                    340                 345                 350

Phe Asn Lys Leu Ser Asn Gly Glu Lys Ser Gln Pro Met Asn Ile Val
                    355                 360                 365

Ile Lys Ile Lys Glu Ala Asn Gly Lys Pro Ala Ile Lys Ile Ser Asp
                    370                 375                 380

Asn Ile Gly Lys Asn Met Gly Asp Gln Ala Thr Val Asp Arg Val Lys
385                 390                 395                 400

Gln Glu Leu Gly Tyr Thr Glu Arg Thr Trp Ser Glu Gly Asp Glu Thr
                    405                 410                 415

His Arg Trp Ser Lys
                420

<210> SEQ ID NO 54
<211> LENGTH: 414
<212> TYPE: PRT
<213> ORGANISM: Yarrowia lipolytica

<400> SEQUENCE: 54

Met Ser Thr Ile Thr Ser Leu Leu Asp Thr Asp Leu Tyr Lys Leu Thr
1               5                   10                  15

Met Gln Ala Ala Val Leu Gln His Phe Pro Ala Ala Gln Ala Thr Phe
                20                  25                  30

Leu Phe Lys Asn Arg Thr Pro Ser Lys Gln Leu Asn Asp Asp Ala Ile
            35                  40                  45

Glu Trp Leu Lys Ser Glu Ile Ala Ala Leu Gly Glu Leu Arg Phe Thr
        50                  55                  60

Glu Asp Glu Ile Val Phe Leu Gln Lys His Val Gly Phe Leu Pro Ala
65                  70                  75                  80

Glu Tyr Phe Glu Tyr Leu Lys Thr Cys Gln Leu Asp Pro Ala Ala Gln
                85                  90                  95

Val Lys Val Thr Val Asn Thr Glu Gly His Leu Glu Ile Glu Val Asn
```

```
                    100                 105                 110
Gly Pro Trp Lys Asp Thr Ile Leu Tyr Glu Ile Pro Leu Leu Ala Leu
            115                 120                 125

Val Ser Glu Ala Tyr Phe Lys Phe Val Asp Lys Asp Trp Ser Tyr Asp
        130                 135                 140

Gly Gln Ser Glu Leu Ala Ala Thr Lys Ala Gln Glu Leu Ile Ala Gln
145                 150                 155                 160

Gly Cys Ala Phe Ser Glu Phe Gly Thr Arg Arg Arg Ser Leu Lys
                165                 170                 175

Thr His Asp Ile Val Ile Ala Gly Ile Leu Glu Gly Leu Lys Ser Ala
            180                 185                 190

Gln Gly Asn Gly Ile Phe Thr Gly Thr Ser Asn Val Tyr Leu Ala Lys
        195                 200                 205

Lys Tyr Asn Leu Lys Pro Ile Gly Thr Val Ala His Glu Trp Met Met
    210                 215                 220

Gly Val Ala Ala Thr Gly Asp Tyr Ser Thr Ala Asn Leu Arg Ala
225                 230                 235                 240

Met Glu Leu Trp Ile Gln Thr Val Gly Asp Ala Asn Ala Gly Val Ala
                245                 250                 255

Leu Thr Asp Thr Phe Gly Thr Glu Ser Phe Leu Leu Asp Phe Asn Lys
            260                 265                 270

Pro Leu Thr Asp Ile Tyr Asn Gly Val Arg Gln Asp Ser Gly Asp Pro
        275                 280                 285

Leu Glu Tyr Thr Lys Leu Leu Gly Asp His Tyr Lys Gln Leu Gly Tyr
    290                 295                 300

Glu Pro Met Ser Lys Val Ile Val Tyr Ser Asp Ser Leu Asp Val Glu
305                 310                 315                 320

Lys Cys Gly Lys Tyr Lys Ala Ala Ala Glu Asn Gly Leu Lys Ala
                325                 330                 335

Ala Phe Gly Val Gly Thr Phe Phe Thr Asn Asp Phe Lys Arg Leu Ser
            340                 345                 350

Asp Gly Gln Lys Ser Thr Pro Leu Asn Ile Val Ile Lys Ile Gln Gln
        355                 360                 365

Leu Asn Gly Gln Ser Cys Ile Lys Leu Ser Asp Asn Leu Ser Lys Asn
    370                 375                 380

Met Gly Asp Pro Glu Thr Val Glu Arg Val Lys Arg Glu Leu Gly Tyr
385                 390                 395                 400

Val Glu Lys Gly Asp Val Ile Asp Glu Ser Lys Arg Trp Asn
                405                 410

<210> SEQ ID NO 55
<211> LENGTH: 490
<212> TYPE: PRT
<213> ORGANISM: Aspergillus fumigatus

<400> SEQUENCE: 55

Met Ser Gln Glu Thr Thr Pro Pro Tyr Pro Glu Gly Ile Phe Ser Leu
1               5                   10                  15

Leu Asp Thr Asp Leu Tyr Lys Leu Thr Met Gln Cys Ala Ile Leu Lys
            20                  25                  30

Tyr Phe Pro Asp Val His Val Thr Tyr Gly Phe Thr Asn Arg Thr Pro
        35                  40                  45

Asp Met Lys Leu Thr Arg Gly Ala Tyr Lys Trp Leu Leu Glu Gln Met
    50                  55                  60

Asp Arg Leu Ala Asn Val Arg Val Thr Asp Glu Glu Ile Ala Phe Leu
```

-continued

```
                65                  70                  75                  80
Lys Lys Gln Cys Pro Tyr Phe Asn His Ala Tyr Leu Arg Tyr Leu Ser
                    85                  90                  95

Thr Phe Gln Leu Lys Pro Ser Glu Gln Ile Asp Ile Lys Phe Arg Pro
                    100                 105                 110

Val Gln Asp Ser Gly Ser Asp Asp Leu Gly Asp Ile Glu Tyr Met
                    115                 120                 125

Val Lys Gly Leu Trp Val Glu Thr Ile Leu Tyr Glu Ile Pro Leu Leu
    130                 135                 140

Ala Leu Thr Ser Gln Ala Tyr Phe Met Phe Thr Asp Lys Asp Trp Asp
145                 150                 155                 160

His Ser Asn Gln Glu Glu Lys Ala Phe Arg Lys Gly Cys Thr Leu Leu
                    165                 170                 175

Glu Asn Gly Cys Ile Phe Ser Glu Phe Gly Ser Arg Arg Arg Arg Asp
                    180                 185                 190

Tyr His Thr Gln Asp Leu Val Met Gln Gly Leu Cys Arg Ala Ala Glu
                    195                 200                 205

Glu Gly Lys Arg Gln Gly Trp Lys Gly Val Phe Ser Gly Thr Ser Asn
    210                 215                 220

Val His Phe Ala Met Arg Tyr Gly Val Thr Pro Ile Gly Thr Val Ala
225                 230                 235                 240

His Glu Trp Phe Met Ala Ile Ala Ala Ile Thr Asp Asp Tyr Glu Asn
                    245                 250                 255

Ala Asn Glu Leu Ala Leu Arg Tyr Trp Leu Gly Cys Phe Gly Glu Gly
                    260                 265                 270

Val Leu Gly Ile Ala Leu Thr Asp Thr Phe Gly Thr Pro Ala Phe Leu
                    275                 280                 285

Asp Ala Phe Arg Lys Pro Ile Pro His His Thr Ser Ala Gly Val Gly
    290                 295                 300

Ala Val Ala Thr Ile Ala Ser Gly Ala Ser Thr Thr Ser Glu Ser Gln
305                 310                 315                 320

Pro Gln Thr Glu Ala Glu Thr Lys Pro Pro Val Thr Ala Pro Leu His
                    325                 330                 335

Glu Asn Asp Ser Gln His Ser Pro Lys Thr Tyr Ala Gln Val Tyr Thr
                    340                 345                 350

Gly Val Arg Gln Asp Ser Gly Asp Pro Thr Tyr Phe Val Lys Met Val
                    355                 360                 365

Arg Asp Phe Tyr Asp Asn Glu Gly Ile Lys Glu Lys Lys Thr Val Val
    370                 375                 380

Phe Ser Asp Ser Leu Asn Ile Glu His Cys Leu Glu Tyr Lys Thr Ile
385                 390                 395                 400

Ala Glu Glu Ala Gly Phe Ala Pro Ile Phe Gly Val Gly Thr Phe Phe
                    405                 410                 415

Thr Asn Asp Phe Thr Asn Lys Ser Asp Gly Lys Ser Lys Pro Leu
                    420                 425                 430

Asn Ile Val Ile Lys Ile Ala Thr Ala Asn Gly Arg Pro Ala Val Lys
                    435                 440                 445

Leu Ser Asp Asn Met Gly Lys Asn Thr Gly Asp Lys Asn Met Val Gln
    450                 455                 460

Glu Val Lys Lys Arg Leu Gly Tyr Ile Glu His Tyr Trp Glu Glu Gly
465                 470                 475                 480

Asp Glu Ser Asn Arg Trp Ala Lys Gln Gly
                    485                 490
```

<210> SEQ ID NO 56
<211> LENGTH: 489
<212> TYPE: PRT
<213> ORGANISM: Aspergillus oryzae

<400> SEQUENCE: 56

```
Met Asp Gln Glu Gly Ser Pro Pro Ile Pro Glu Gly Ile Cys Ser Leu
 1               5                  10                  15

Leu Asp Thr Asp Leu Tyr Lys Leu Thr Met Gln Cys Ala Val Leu Lys
            20                  25                  30

Tyr Phe Pro Asp Thr His Val Thr Tyr Gly Phe Thr Asn Arg Thr Pro
        35                  40                  45

His Met Lys Leu Thr Arg Gly Ala His Lys Trp Leu Leu Lys Gln Met
    50                  55                  60

Asp Arg Leu Ala Asn Ile Arg Ile Thr Glu Glu Ile Lys Phe Leu
65                  70                  75                  80

Lys Thr Arg Cys Pro Tyr Phe Asn Asp Ala Tyr Leu Asp Phe Leu Thr
                85                  90                  95

Thr Phe Lys Leu Lys Pro Ser Glu Gln Ile Glu Ile Lys Phe Thr Pro
            100                 105                 110

Val Asn Asp Thr Gly Ser Asp Ser Asp Thr Gly Asp Val Glu Tyr Leu
        115                 120                 125

Val Lys Gly Leu Trp Val Asp Thr Ile Leu Tyr Glu Ile Pro Leu Leu
    130                 135                 140

Ala Leu Thr Ser Glu Ala Tyr Phe Met Phe Ser Asp Lys Asp Trp Asp
145                 150                 155                 160

Tyr Ser Cys Gln Glu Glu Lys Ala Tyr Arg Lys Gly Cys Thr Leu Leu
                165                 170                 175

Glu Asn Gly Cys Ile Phe Ser Glu Phe Gly Ser Arg Arg Arg Arg Asp
            180                 185                 190

Tyr His Thr His Asp Leu Val Met Val Gly Leu Met Lys Ala Ala Glu
        195                 200                 205

Glu Gly Lys Arg Gln Gly Trp Lys Gly Arg Phe Thr Gly Ser Ser Asn
    210                 215                 220

Val His Phe Ala Met Lys Tyr Gly Val Asp Pro Val Gly Thr Val Ala
225                 230                 235                 240

His Glu Trp Tyr Met Thr Ile Ala Ala Ile Thr Asp Asp Tyr Glu Asn
                245                 250                 255

Ala Asn Glu Leu Ala Leu Arg Tyr Trp Leu Gly Cys Phe Gly Lys Gly
            260                 265                 270

Val Leu Gly Ile Ala Leu Thr Asp Thr Phe Gly Thr Pro Ala Phe Leu
        275                 280                 285

Asp Ala Phe Arg Lys Pro Ile Pro Ala Phe Thr Ser Ala Gly Ala Gly
    290                 295                 300

Ala Val Ser Thr Ser Ala Ser Gly Pro Ala Thr Thr Asn Glu Ser Thr
305                 310                 315                 320

Val Gln Ser Glu Ala Glu Thr Lys Ala Pro Ile Thr Ala Pro Leu Arg
                325                 330                 335

Asp Gly Gly Ala Arg Thr Ser His Glu Thr Tyr Ala Gln Ala Tyr Thr
            340                 345                 350

Gly Val Arg Gln Asp Ser Gly Asp Pro Val Tyr Phe Val Lys Met Val
        355                 360                 365

Arg Asp Phe Tyr Asp Arg Glu Gly Ile Thr Asp Lys Lys Thr Met Val
    370                 375                 380
```

```
Phe Ser Asp Ser Leu Asn Ile Glu His Cys Leu Glu Tyr Lys Val Ile
385                 390                 395                 400

Ala Glu Glu Ala Gly Phe Gln Pro Val Phe Gly Val Gly Thr Phe Phe
            405                 410                 415

Thr Asn Asp Phe Thr Asn Lys Ser Asn Asp Glu Lys Ser Lys Pro Leu
        420                 425                 430

Asn Ile Val Ile Lys Ile Ser Thr Ala Asn Gly His Pro Ala Val Lys
            435                 440                 445

Leu Ser Asp Asn Met Gly Lys Asn Thr Gly Asp Lys Gln Lys Val Gln
    450                 455                 460

Glu Val Lys Lys Lys Leu Gly Tyr Val Glu His Glu Trp Glu Glu Gly
465                 470                 475                 480

Asp Glu Ser Asn Arg Trp Ser Lys Arg
                485

<210> SEQ ID NO 57
<211> LENGTH: 477
<212> TYPE: PRT
<213> ORGANISM: Neurospora crassa

<400> SEQUENCE: 57

Met Asp Phe Asn Ser Ser Leu Pro His Pro Ala Gly Val Ile Ser Phe
1               5                   10                  15

Leu Asp Thr Asp Leu Tyr Lys Leu Thr Met Gln Cys Ala Val Leu Lys
            20                  25                  30

Tyr Phe Lys Asp Val Pro Val Thr Tyr Ser Phe Thr Asn Arg Thr Pro
        35                  40                  45

Glu Lys Lys Leu Ser Arg Glu Ala Phe Val Trp Leu Glu Glu Gln Val
    50                  55                  60

Met Lys Leu Gly Asn Ile Ser Leu Ser Pro Glu Gly Leu Gln Phe Leu
65                  70                  75                  80

Lys Thr His Cys Pro Tyr Leu Thr Glu Glu Tyr Leu Asp Tyr Leu Ser
                85                  90                  95

Glu Phe Arg Leu Arg Pro Arg Glu Gln Val Ala Val Ser Phe Arg Pro
            100                 105                 110

Asp Gly Asp Ser Asp Leu Gly Asp Ile His Tyr Asp Ile Lys Gly Asn
        115                 120                 125

Trp Ala Glu Thr Ile Leu Tyr Glu Ile Pro Leu Leu Ala Leu Thr Ser
    130                 135                 140

Glu Ala Tyr Phe Lys Phe Met Asp Thr Asp Trp Asp Tyr Asp Gly Gln
145                 150                 155                 160

Glu Glu Lys Ala Tyr Glu Lys Gly Met Arg Leu Leu Glu Ala Gly Cys
                165                 170                 175

Val Phe Ser Glu Phe Gly Thr Arg Arg Arg Arg Asp Tyr His Thr Gln
            180                 185                 190

Ala Leu Val Phe Arg Gly Leu Thr Lys Ala Ala Lys Glu Ala Glu Lys
        195                 200                 205

Arg Gly Leu Thr Gly Lys Leu Ser Gly Thr Ser Asn Val His Leu Ala
    210                 215                 220

Met Arg Phe Asn Ile Pro Pro Val Gly Thr Val Ala His Glu Trp Phe
225                 230                 235                 240

Met Gly Asn Ala Ala Ile Leu Gly Asp Tyr Lys Ser Ala Thr Glu Glu
                245                 250                 255

Ala Leu Ser Arg Trp Val Gly Cys Tyr Gly Pro Gly Val Leu Gly Ile
            260                 265                 270
```

```
Ala Leu Thr Asp Thr Phe Gly Thr Pro Glu Phe Leu Arg Ala Phe Ser
            275                 280                 285

Lys Pro Met Ser Ala Ser Gly Glu Pro Val Pro Gln Pro Arg Asp Arg
            290                 295                 300

Lys Ile Ser Thr Ala Asp Ala Phe Ile Ser Ala Lys Asp Phe Ile
305                 310                 315                 320

Lys Asp Leu His Pro Asp Lys Thr Tyr Ala Gln Val Phe Thr Gly Val
                325                 330                 335

Arg Gln Asp Ser Gly Asp Pro Lys Glu Phe Val Lys Leu Met Arg Lys
            340                 345                 350

Phe Tyr Asp Glu Gln Gly Ile Lys Asp Lys Val Ile Val Phe Ser
                355                 360                 365

Asp Ser Leu Asp Ile Asp Arg Cys Leu Glu Tyr Lys Glu Val Ala Glu
370                 375                 380

Ala Ala Gly Phe Gln Pro Thr Phe Gly Val Gly Thr Tyr Phe Thr Asn
385                 390                 395                 400

Asp Phe Val His Lys Ala Thr Gly Lys Lys Ser Thr Pro Leu Asn Ile
                405                 410                 415

Val Ile Lys Leu Ser Ser Ala Ala Gly Asn Pro Ala Val Lys Ile Ser
            420                 425                 430

Asp Asn Val Gly Lys Asn Thr Gly Asp Lys Ala Thr Val Glu Lys Val
            435                 440                 445

Lys Arg Glu Leu Gly Tyr Val Glu Lys Asp Trp Ser Glu Gly Asp Glu
450                 455                 460

Ser Ala Arg Trp Gly His Asp Gly Asp Ala Ala Thr Ala
465                 470                 475

<210> SEQ ID NO 58
<211> LENGTH: 481
<212> TYPE: PRT
<213> ORGANISM: Chaetomium globosum

<400> SEQUENCE: 58

Met Asp Phe Asn Ser Ser Pro Tyr Pro Glu Gly Val Ile Ser Phe
1               5                   10                  15

Leu Asp Thr Asp Leu Tyr Lys Leu Thr Met Gln Cys Ala Val Leu Lys
            20                  25                  30

Tyr Tyr Lys Asn Val Pro Val Thr Tyr Ala Phe Thr Asn Arg Thr Pro
            35                  40                  45

Glu Lys Lys Leu Ser Arg Lys Ala Phe Arg Trp Leu Glu Asp Gln Val
        50                  55                  60

Arg Lys Leu Gly Asn Ile Ser Leu Ser Ala Glu Glu Leu Tyr Tyr Leu
65              70                  75                  80

Lys Glu His Cys Pro Tyr Leu Ser Pro Ala Tyr Leu Glu Phe Leu Ser
                85                  90                  95

Glu Phe Arg Leu Arg Pro Arg Glu Gln Val Val Leu Ser Phe Leu Pro
            100                 105                 110

Thr Gly Glu Asp Thr Gly Ala Glu Ser Asp Ile Gly Asp Leu Asp Ile
        115                 120                 125

Lys Ile Ser Gly Ile Trp Ser Glu Ala Ile Leu Tyr Glu Ile Pro Leu
130                 135                 140

Leu Ser Leu Thr Ser Glu Ala Tyr Phe Lys Phe Met Glu Pro Asp Trp
145                 150                 155                 160

Thr Tyr Glu Gly Gln Glu Asp Gln Ala Phe Glu Lys Gly Met Arg Leu
                165                 170                 175
```

```
Leu Glu Ala Gly Cys Val Phe Ser Glu Phe Gly Thr Arg Arg Arg
            180                 185                 190

Asp Tyr His Thr Gln Ala Leu Val Phe Arg Gly Leu Thr Lys Ala Ser
        195                 200                 205

Lys Glu Ala Glu Lys Arg Gly Leu Ser Gly Lys Leu Ser Gly Thr Ser
210                 215                 220

Asn Val His Leu Ala Met Arg Phe Asn Ile Pro Pro Val Gly Thr Val
225                 230                 235                 240

Ala His Glu Trp Phe Met Gly Ser Ala Ala Ile Val Gly Asp Tyr Arg
                245                 250                 255

Lys Ala Thr Glu Glu Ala Leu Arg His Trp Val Gly Cys Phe Gly Glu
            260                 265                 270

Gly Val Leu Gly Ile Ala Leu Thr Asp Thr Phe Gly Thr Pro Asp Phe
        275                 280                 285

Leu Thr Ala Phe Ser Lys Pro Ile Glu Tyr Leu Glu Pro Pro Ser Pro
    290                 295                 300

Thr Thr Ala Arg Lys Pro Ser Val Ala Asp Ser Phe Ile Ser Thr Ser
305                 310                 315                 320

Pro Ser Val Ala Ser His Gln Lys Pro Asn Lys Thr Tyr Ala Glu Val
                325                 330                 335

Phe Thr Gly Val Arg Gln Asp Ser Gly Asp Pro Lys Thr Phe Val Lys
            340                 345                 350

Ile Ile Gly Lys Phe Tyr Arg Glu Gln Gly Ile Lys Asp Lys Lys Val
        355                 360                 365

Ile Val Phe Ser Asp Ser Leu Asn Ile Asp Arg Cys Leu Glu Tyr Lys
    370                 375                 380

Gln Val Ser Glu Glu Ala Gly Phe Gln Pro Thr Phe Gly Val Gly Thr
385                 390                 395                 400

Phe Leu Thr Asn Asp Phe Val Asn Thr Lys Thr Gly Lys Lys Ser Thr
                405                 410                 415

Pro Leu Asn Ile Val Ile Lys Leu Ser Ser Ala Asp Gly Asn Pro Ala
            420                 425                 430

Ile Lys Ile Ser Asp Asn Ile Gly Lys Asn Thr Gly Asp Lys Ala Thr
        435                 440                 445

Val Glu Lys Val Lys Arg Glu Leu Gly Tyr Val Glu Lys Met Trp Glu
    450                 455                 460

Gly Gly Asp Glu Thr Ala Arg Trp Gly Arg Glu Asp Asp Ala Pro Lys
465                 470                 475                 480

Gln

<210> SEQ ID NO 59
<211> LENGTH: 487
<212> TYPE: PRT
<213> ORGANISM: Aspergillus nidulans

<400> SEQUENCE: 59

Met Gly Glu His Ser Leu Leu Pro Asp Gly Val Phe Ser Leu Leu Asp
1               5                   10                  15

Thr Asp Leu Tyr Lys Leu Thr Met Gln Cys Ala Ile Leu Lys Tyr Phe
                20                  25                  30

Pro Asp Val Gln Val Thr Tyr Gly Phe Thr Asn Arg Thr Pro His Met
            35                  40                  45

Lys Leu Thr Arg Gly Ala Tyr Lys Trp Met Leu Ala Gln Met Asp Lys
        50                  55                  60

Leu Ala Asn Ile Arg Val Thr Glu Asp Glu Ile Ala Phe Leu Lys Arg
```

```
            65                  70                  75                  80
Arg Cys Pro Tyr Phe Asn Thr Ala Tyr Leu Asp Phe Leu Thr Asn Phe
                    85                  90                  95

Arg Leu Lys Pro Ser Glu Gln Ile Asp Ile Asn Phe Thr Pro Val Asn
                100                 105                 110

Asp Thr Gly Ser Asp Ser Asp Phe Gly Asp Ile Asp Tyr Ile Val Lys
            115                 120                 125

Gly Ala Trp Val Asp Thr Ile Leu Tyr Glu Ile Pro Leu Leu Ala Leu
        130                 135                 140

Thr Ser Gln Ala Tyr Phe Met Phe Ser Asp Lys Asp Trp Asn Tyr Glu
145                 150                 155                 160

Cys Gln Glu Gly Lys Ala Tyr Arg Lys Gly Tyr Val Leu Leu Glu Asn
                165                 170                 175

Gly Cys Thr Phe Ser Glu Phe Gly Thr Arg Arg Arg Ser Tyr His
                180                 185                 190

Thr Gln Asp Leu Val Met Gln Gly Leu Cys Arg Ala Ala Arg Glu Gly
            195                 200                 205

Lys Ala Lys Gly Leu Pro Gly Val Phe Thr Gly Ser Ser Asn Val His
        210                 215                 220

Phe Ala Met Lys Tyr Asp Val Asp Pro Val Gly Thr Val Ala His Glu
225                 230                 235                 240

Trp Tyr Met Thr Ile Ala Ala Ile Thr Asp Asp Tyr Glu Asn Ala Asn
                245                 250                 255

Glu Met Ala Leu Lys Tyr Trp Leu Gly Cys Phe Gly Glu Gly Val Leu
                260                 265                 270

Gly Ile Ala Leu Thr Asp Thr Phe Gly Thr Pro Ala Phe Leu Asp Ala
        275                 280                 285

Phe Arg Lys Pro Ile Pro Asp Tyr Thr Ser Ala Gly Thr Gly Ala Val
290                 295                 300

Ser Thr Thr Ala Ser Gly Pro Ser Thr Thr Ala Glu Ser Asn Ile Gln
305                 310                 315                 320

Ser Glu Ala Glu Thr Lys Ala Pro Ile Thr Ala Pro Leu Ser Pro Asp
                325                 330                 335

His Pro Pro Pro Ala Val Lys Thr Tyr Ala Gln Val Tyr Ala Gly Val
                340                 345                 350

Arg Gln Asp Ser Gly Asp Pro Ser Tyr Phe Val Lys Met Ala Arg Asp
            355                 360                 365

Phe Tyr Asp Arg Glu Gly Ile Thr Gly Thr Lys Thr Val Val Phe Ser
        370                 375                 380

Asp Ser Leu Asp Ile Glu His Cys Leu Glu Tyr Lys Val Leu Ala Glu
385                 390                 395                 400

Glu Ala Gly Phe Lys Pro Val Phe Gly Val Gly Thr Phe Phe Thr Asn
                405                 410                 415

Asp Phe Ile Asn Thr Thr Asn Glu Lys Ser Gln Pro Leu Asn Ile
                420                 425                 430

Val Ile Lys Ile Ser Ser Ala Asn Gly Arg Ala Ala Val Lys Leu Ser
            435                 440                 445

Asp Asn Met Gly Lys Asn Thr Gly Asp Lys Thr Val Gln Ala Val
        450                 455                 460

Lys Lys Arg Leu Gly Tyr Val Glu His Glu Trp Glu Glu Gly Asp Glu
465                 470                 475                 480

Arg Asn Arg Trp Ala Arg Lys
                485
```

<210> SEQ ID NO 60
<211> LENGTH: 459
<212> TYPE: PRT
<213> ORGANISM: Gibberella moniliformis

<400> SEQUENCE: 60

```
Met Asp Phe Asn Ser Ser Pro Phe Pro Glu Gly Val Ile Ser Phe
1               5                   10                  15

Leu Asp Thr Asp Leu Tyr Lys Leu Thr Met Gln Cys Ala Val Phe Lys
                20                  25                  30

Phe Phe Lys Asp Val Pro Val Thr Tyr Ala Tyr Thr Asn Arg Thr Pro
            35                  40                  45

Asp Lys Lys Leu Ser Arg Thr Ala Phe Lys Trp Leu Glu Glu Gln Ile
        50                  55                  60

Arg Lys Leu Gly Asn Ile Ser Leu Ser Thr Asp Glu Tyr Leu Phe Leu
65                  70                  75                  80

Lys Lys His Cys Asp Tyr Leu Ser Asp Asp Tyr Leu Asn Phe Leu Lys
                85                  90                  95

Glu Phe Arg Leu Ser Pro Arg Glu Gln Val Val Ala Thr Phe Thr Pro
            100                 105                 110

Val Gly Glu Asp Asn Gly Asp Asp Ser Ile Glu Gly Asp Val Asp Ile
        115                 120                 125

Gln Ile Lys Gly Thr Trp Val Asp Thr Ile Leu Tyr Glu Ile Pro Met
    130                 135                 140

Leu Ala Leu Thr Ser Glu Ala Tyr Phe Lys Phe Met Asp Thr Asp Trp
145                 150                 155                 160

Asn Tyr Glu Gly Gln Glu Lys Gln Ala Phe Glu Lys Gly Leu Lys Leu
                165                 170                 175

Leu Glu Ala Gly Cys Ile Thr Ser Glu Phe Gly Thr Arg Arg Arg Arg
            180                 185                 190

Asp Tyr His Thr Gln Ala Leu Val Phe Arg Gly Leu Val Gln Ala Ser
        195                 200                 205

Lys Glu Ala Glu Lys Lys Gly Phe Pro Gly Lys Leu Ser Gly Thr Ser
    210                 215                 220

Asn Val His Leu Ala Met Arg Phe Asn Ile Pro Pro Val Gly Thr Val
225                 230                 235                 240

Ala His Glu Trp Phe Met Gly Val Ala Ala Ile Ile Gly Asp Tyr Arg
                245                 250                 255

Ser Ala Thr Glu Val Ala Leu Arg His Trp Val Ala Cys Phe Gly Asn
            260                 265                 270

Lys Leu Gly Ile Ala Leu Thr Asp Thr Phe Gly Thr Gln Glu Phe Leu
        275                 280                 285

Arg Ala Phe Thr Gln Pro Val Gln Thr Ile Glu Gly Gly Phe Pro Ala
    290                 295                 300

Glu Thr Phe Lys Lys Ala Asp Gly Thr Met Lys Thr Tyr Ala Glu Thr
305                 310                 315                 320

Phe Ala Gly Ile Arg Gln Asp Ser Gly Asp Pro Ala Glu Tyr Thr Lys
                325                 330                 335

Trp Met Lys Glu Phe Tyr Asp Lys Gln Gly Ile Thr Asp Lys Lys Leu
            340                 345                 350

Ile Val Phe Ser Asp Ser Leu Asn Ile Glu Arg Cys Leu Glu Tyr Lys
        355                 360                 365

Lys Ile Ala Glu Asp Leu Gly Phe Gln Pro Thr Phe Gly Val Gly Thr
    370                 375                 380
```

```
Tyr Leu Thr Asn Asp Phe Val His Leu Thr Thr Gly Lys Lys Ser Val
385                 390                 395                 400

Pro Leu Asn Ile Val Ile Lys Ile Ser Ser Ala Ala Gly Arg Pro Ala
                405                 410                 415

Val Lys Ile Ser Asp Asn Ile Gly Lys Asn Thr Gly Asp Lys Glu Thr
            420                 425                 430

Val Glu Lys Val Lys Gln Glu Leu Gly Tyr Val Glu Arg Glu Trp Lys
        435                 440                 445

Glu Gly Asp Glu Thr Ser Arg Trp Gly Lys Glu
    450                 455

<210> SEQ ID NO 61
<211> LENGTH: 410
<212> TYPE: PRT
<213> ORGANISM: Schizosaccharomyces pombe

<400> SEQUENCE: 61

Met Ser Glu Pro Ala Val Val Ser Ile Leu Asp Thr Asp Leu Tyr Lys
1               5                   10                  15

Leu Thr Met Leu Gln Ala Val Leu Glu His Tyr Pro Asp Ala Gln Val
            20                  25                  30

Ser Tyr Lys Tyr Thr Asn Arg Ser Pro Lys Met Ala Leu Asn Gln Glu
        35                  40                  45

Ala Tyr Asn Trp Leu Arg Glu Gln Ile Arg Gly Leu Arg Asn Leu His
    50                  55                  60

Leu Leu Pro Glu Glu Gln Trp Leu Arg Lys Asn Cys Pro Tyr Leu
65                  70                  75                  80

Lys Glu Ser Phe Tyr Glu Phe Met His Glu Phe Glu Phe Asp Pro Glu
                85                  90                  95

Asn Ser Ile Ser Leu Asn Tyr Asp Ser Glu Thr Lys Asp Leu Ser Ile
            100                 105                 110

Phe Ile His Gly Leu Trp Lys Asn Thr Ile Phe Tyr Glu Ile Pro Leu
        115                 120                 125

Leu Ala Leu Val Ser Glu Ser Tyr Phe Lys Phe Val Asp Lys Asp Trp
130                 135                 140

Ser Pro Glu Gly Gln Phe Glu Lys Ala Tyr Glu Lys Gly Lys Arg Leu
145                 150                 155                 160

Ile Arg Ala Gly Cys Ala Phe Thr Asp Phe Gly Thr Arg Arg Arg
                165                 170                 175

Asp Pro His Thr Gln Glu Ile Val Leu Gln Gly Leu Met Lys Ala Gln
            180                 185                 190

Glu Asp Phe Lys Gly Pro Gly Ser Phe Leu Gly Thr Ser Asn Val Tyr
        195                 200                 205

Phe Ala Ala Lys Tyr Asn Leu Asn Val Ser Gly Thr Val Ala His Glu
210                 215                 220

Trp Tyr Met Gly Ile Ala Ala Ile Thr Gln Asn Tyr Lys Gln Ala Asn
225                 230                 235                 240

Arg Ile Ala Ser Leu Lys Trp Val Gln Thr Phe Gly Thr Ser Leu Leu
                245                 250                 255

Ile Ala Leu Thr Asp Thr Phe Ser Thr Asp Val Phe Leu Lys Ser Phe
            260                 265                 270

Thr Ala Asn Ser Ala Asp Asp Leu Ala Asn Val Phe His Gly Val Arg
        275                 280                 285

Gln Asp Ser Gly Cys Ala Glu Glu Tyr Ile Glu Lys Val Val Lys His
290                 295                 300
```

```
Tyr Lys Ser Ile Gly Val Asp Pro Ser Thr Lys Val Ile Val His Ser
305                 310                 315                 320

Asp Ala Leu Asn Val Asp Arg Cys Ile Glu Leu Tyr Lys Tyr Cys Glu
                325                 330                 335

Lys Cys Gly Ile Lys Ser Ala Phe Gly Ile Gly Thr Asn Leu Thr Ser
                340                 345                 350

Asp Phe Gln Lys Val Ser Asn Pro Ser Glu Val Ser Lys Pro Met Asn
                355                 360                 365

Ile Val Ile Lys Leu Phe Ser Ala Glu Gly Thr Lys Ala Val Lys Ile
370                 375                 380

Ser Asp Asp Ile Met Lys Asn Thr Gly Asp Arg Asp Ala Val Ile Gln
385                 390                 395                 400

Ala Lys His Gln Leu Cys Leu Pro Ile Ala
                405                 410

<210> SEQ ID NO 62
<211> LENGTH: 1971
<212> TYPE: PRT
<213> ORGANISM: Magnaporthe grisea

<400> SEQUENCE: 62

Met Asp Phe Asn Ser Asp Ser Pro Phe Pro Glu Gly Val Ile Ser Phe
1               5                   10                  15

Leu Asp Thr Asp Leu Tyr Lys Leu Thr Met Gln Cys Ala Val Leu Lys
                20                  25                  30

Tyr Tyr Ser Asn Thr Ser Val Thr Tyr Ser Phe Thr Asn Arg Thr Pro
                35                  40                  45

Glu Lys Arg Leu Ser Arg Lys Ala Tyr Gln Trp Leu Gln Asp Gln Ile
50                  55                  60

Arg Asn Glu Glu Tyr Arg Phe Leu Lys Asp Asn Cys Pro Tyr Leu Gly
65                  70                  75                  80

Thr Gln Tyr Leu Glu Phe Leu Gln Asn Phe Arg Leu Asn Pro Arg Asp
                85                  90                  95

Gln Val Ile Val Ser Phe Ala Pro Val Gly Lys His Glu Gly Ala Asp
                100                 105                 110

Ser Asp Val Gly Asp Ile Asp Ile Gln Ile Ser Gly Lys Trp Val Asp
                115                 120                 125

Thr Ile Leu Tyr Glu Ile Pro Ile Leu Ala Leu Thr Ser Glu Ala Tyr
130                 135                 140

Phe Arg Phe Met Asp Thr Asp Trp Asp Tyr Gln Gly Gln Glu Glu Leu
145                 150                 155                 160

Ala Tyr Glu Lys Gly Lys Arg Ile Leu Glu Ala Gly Cys Ile Leu Ser
                165                 170                 175

Glu Phe Gly Thr Arg Arg Arg Asp Tyr His Thr Gln Ala Leu Val
                180                 185                 190

Phe Arg Gly Leu Val Lys Ala Ser Lys Glu Ala Gln Lys Arg Gly Leu
                195                 200                 205

Ser Gly Lys Leu Ser Gly Thr Ser Asn Val His Leu Ala Met Arg Phe
210                 215                 220

Asn Met Ala Pro Val Gly Thr Val Ala His Glu Trp Phe Met Gly Ile
225                 230                 235                 240

Ala Ala Ile Ile Gly Asp Tyr Arg Ser Ala Ser Glu Glu Ala Leu Ala
                245                 250                 255

Arg Trp Val Gly Ala Phe Gly Pro Gly Val Leu Ala Ile Ala Leu Thr
                260                 265                 270
```

-continued

```
Asp Thr Phe Gly Thr Pro Glu Phe Leu Lys Ser Phe Ser Arg Pro Val
        275                 280                 285

Arg Trp Leu Glu Glu Ala His Ser Ala Ala Ala Gly Asn Glu Ser Lys
290                 295                 300

Thr Tyr Ala Gln Val Phe Ala Gly Val Arg Gln Asp Ser Gly Asp Pro
305                 310                 315                 320

Thr Thr Phe Val Lys Arg Met Arg Glu Phe Tyr Asp Gln Gln Arg Ile
                325                 330                 335

Lys Glu Lys Lys Thr Ile Val Phe Ser Asp Ser Leu Asp Ile Asp Arg
            340                 345                 350

Cys Leu Val Tyr Lys Gln Val Ser Glu Ala Ala Gly Phe Gln Pro Thr
        355                 360                 365

Phe Gly Val Gly Thr Phe Leu Thr Asn Asp Phe Val Gly Lys Ser Thr
370                 375                 380

Gly Lys Lys Ser Thr Pro Leu Asn Ile Val Ile Lys Leu Ser Ser Ala
385                 390                 395                 400

Asp Gly Lys Pro Ala Val Lys Leu Ser Asp Asn Ile Gly Lys Asn Thr
                405                 410                 415

Gly Asp Ala Asn Thr Val Glu Lys Val Lys Arg Glu Ile Gly Tyr Glu
            420                 425                 430

Glu Lys Asp Trp Glu Gly Gly Asp Glu Thr Ser Arg Leu Asn Gly Asn
        435                 440                 445

Arg Tyr Asp Arg Gly Ala His Ala Leu Met Asp Leu Ser Asp Pro Ala
450                 455                 460

Ala Thr Ser Arg Ser Arg Ser Val Val Tyr Phe Phe Lys Ser Gly Thr
465                 470                 475                 480

Thr Leu Ser Glu Ile Pro Glu Ser Pro Pro Gly Arg Ser Gly Pro Met
                485                 490                 495

Asn Ser Gln Arg Ser His Gly Gly Ala Phe Asp Arg Glu Arg Asp
            500                 505                 510

Pro Arg Glu Arg Asp Leu Asp Glu His Arg His Arg Pro Leu Thr Gln
        515                 520                 525

Glu Glu Ala Ala Asn Arg Asp Arg Glu Arg Asp Ile Asp Arg Glu Arg
530                 535                 540

Glu Arg Glu His Ala Asp Arg Gln Gln Pro Arg Glu Ala Tyr Pro Pro
545                 550                 555                 560

Gly Ala Pro Leu His Ser Thr Ala Gly Ser Ile Pro Ile His Gln Pro
                565                 570                 575

Val Ala Ser Arg Ile Ala Gly Val Ile His Ser Pro Gly Gly Leu Leu
            580                 585                 590

Gly Ala His Asn Gly Ala Pro Gly Gly Leu Pro Leu Gly Ala Pro Thr
        595                 600                 605

Thr Gln Leu Ala Gly Phe Gly Gly Pro Ile His Ser Asp Pro Ala Arg
610                 615                 620

Gln Met Pro Pro Gln Pro Asn Gln Asn Ser Thr Gly Gly Gln Gln
625                 630                 635                 640

His Gln Met Phe Ala Pro Ile Pro Gln Gln Ala Gly Gly Pro Asn Gly
                645                 650                 655

Ser Leu Gly Pro Gly Gly Ser Pro Gly Ser Val Phe Gly Gly Pro Leu
            660                 665                 670

Gln Thr Glu Asn Gly Arg Ala Pro Val Gln Gln Ala Pro Pro Ala
        675                 680                 685

Val Val Pro Pro Ala Gln Thr Ser Ser Ala Ala Gly Leu Ser Gln Gln
690                 695                 700
```

```
Gly Ser Gln Pro Ile Leu Asn Asp Ala Leu Ser Tyr Leu Asp Gln Val
705                 710                 715                 720

Lys Ala Gln Phe His Glu Gln Pro Asp Val Tyr Asn Arg Phe Leu Asp
                725                 730                 735

Ile Met Lys Asp Phe Lys Ser Gln Thr Ile Asp Thr Pro Gly Val Ile
            740                 745                 750

Asn Arg Val Ser Asp Leu Phe Ala Gly His Pro Asn Leu Ile Gln Gly
        755                 760                 765

Phe Asn Thr Phe Leu Pro Pro Gly Tyr Arg Ile Glu Cys Gly Leu Asp
    770                 775                 780

Asn Asn Pro Asn Ser Ile Arg Val Thr Thr Pro Ser Gly Ser Thr Val
785                 790                 795                 800

His Ser Ile Gly Ala Gly Arg Gly Ala Leu Pro Pro Val Asp Gly Ser
                805                 810                 815

Ala Gly Pro Pro Gly Gln Asn Ala Gln Tyr Leu Gly Pro Asn Ser Arg
                820                 825                 830

Pro Gly Asn Trp Gln Gln Ser Val Gln His Ser Ile Glu Ser Pro Glu
            835                 840                 845

Ala Gln Phe Ser Ala Pro Ala Gln Pro Gly Pro Gly Pro Phe Gly Pro
        850                 855                 860

Val Gly Ala Pro Gly Ala Gln Phe Asp Gly His Ser Pro Ala His Gln
865                 870                 875                 880

Gln Arg Val Val Ser Ser Gly Gln Gln Pro Ala Gly Pro Gly Ser Gly
                885                 890                 895

Leu Val Ala Gly Pro Gly Ser Ala Met Pro Gly Pro Met Ala Arg Asn
                900                 905                 910

Val Gln Thr Pro Thr Pro Gly Ala Gln Pro Ala Ser Leu Asn Gly Ser
            915                 920                 925

Ser Ser Gln Gln Gly Gly Gln Arg Gly Pro Val Glu Phe Asn His Ala
        930                 935                 940

Ile Ser Tyr Val Asn Lys Ile Lys Asn Arg Phe Gln Asp Lys Pro Glu
945                 950                 955                 960

Ile Tyr Lys Gln Phe Leu Glu Ile Leu Gln Thr Tyr Gln Arg Glu Gln
                965                 970                 975

Lys Pro Ile Gln Glu Val Tyr Ala Gln Val Thr Thr Leu Phe His Thr
            980                 985                 990

Ala Pro Asp Leu Leu Glu Asp Phe Lys Gln Phe Leu Pro Glu Ser Ala
        995                 1000                1005

Ala Gln Thr Arg Thr Phe Gly Gln Arg Pro Ala Glu Asp Gly Gly
        1010                1015                1020

Leu Leu Asn His Ile Asn Gln Met Pro Gln Ala Thr Asn Pro Ala
    1025                1030                1035

Arg Glu Gly Pro Lys Met Pro Pro Val Gly Asn Phe Ala Val Pro
    1040                1045                1050

Val Ser Ala Ser Lys Asp Asn Lys Lys Arg Pro Arg Ile Glu Lys
    1055                1060                1065

Pro Pro Ala Ala Thr Pro Gln Ala Gln Gln Ser Pro Ala Val Gly
    1070                1075                1080

Ser Ala Ser Ile Asn Ser Ala Asn Lys Arg Thr Lys Thr Thr His
    1085                1090                1095

Lys Pro Ser Gly Asp Gly Pro Ser Ile Glu Pro Ser Leu Thr Pro
    1100                1105                1110

Ile Val Pro Glu Pro Met Ser Pro Ser Ala Ser Thr Ser Val Ser
```

```
                        1115                1120                1125

Gln Glu Lys Ala Leu Asn Tyr Leu Glu Arg Ile Lys Lys His Ile
1130                1135                1140

Gly Asn Arg Thr Thr Leu His Glu Phe Phe Lys Leu Ile Asn Leu
1145                1150                1155

Tyr Thr Gln Gly Leu Ile Asp Lys Asn Val Leu Val Gln Lys Ala
1160                1165                1170

Gln Met Ile Ile Gly Ala Asn Val Glu Leu Met Thr Trp Phe Lys
1175                1180                1185

Asn Phe Val Arg Tyr Thr Gly Asp Asp Glu Leu Val Glu Asn Lys
1190                1195                1200

Pro Glu Pro Pro Thr Gly Arg Val Ser Leu Ser Asn Cys Arg Gly
1205                1210                1215

Tyr Gly Pro Ser Tyr Arg Leu Leu Arg Lys Arg Glu Arg Leu Lys
1220                1225                1230

Pro Cys Ser Gly Arg Asp Glu Leu Cys Asn Ser Val Leu Asn Asp
1235                1240                1245

Glu Trp Ala Ser His Pro Thr Trp Ala Ser Glu Asp Ser Gly Phe
1250                1255                1260

Val Ala His Arg Lys Asn Ala Phe Glu Glu Gly Leu His Arg Ile
1265                1270                1275

Glu Glu Glu Arg His Asp Tyr Asp Phe Phe Ile Glu Ala Asn Gln
1280                1285                1290

Lys Cys Ile Gln Leu Leu Glu Pro Ile Ala Gln Gln Met Leu Thr
1295                1300                1305

Leu Asn Pro Ala Asp Arg Gln Asn Phe Arg Met Pro Ser Gly Leu
1310                1315                1320

Gly Gly Gln Ser Thr Ser Ile Tyr Lys Arg Val Leu Lys Lys Val
1325                1330                1335

Tyr Gly Ala Asp Lys Gly Ala Glu Val Val Asn Asp Met Phe Gln
1340                1345                1350

His Pro Phe Thr Val Val Pro Ile Val Met Ala Arg Leu Lys Gln
1355                1360                1365

Lys Asp Glu Glu Trp Arg Phe Ser Gln Arg Glu Trp Glu Lys Val
1370                1375                1380

Trp Gln Ser Gln Thr Lys Ala Met His Leu Lys Ser Leu Asp His
1385                1390                1395

Gln Gly Ile Gln Val Lys Gly Asn Asp Lys Arg Thr Leu Ser Ala
1400                1405                1410

Lys His Leu Val Asp Leu Ile Lys Thr Lys His Glu Glu Gln Lys
1415                1420                1425

Arg Gln Arg Val Asn Lys Gly Lys Ala Pro Arg Val Gln His Leu
1430                1435                1440

Trp Ser Phe Thr Asp Gln Gly Val Leu Leu Asp Leu Leu Arg Phe
1445                1450                1455

Met Val Leu Tyr Ala Met Asn Ser Gly Gln His Gly Ser Ser Glu
1460                1465                1470

Lys Asp Arg Ile Leu Glu Phe Phe Glu Asn Ser Val Pro Gln Phe
1475                1480                1485

Phe Gly Ile Leu Pro Glu Gln Val Arg Gln His Leu Gly Asp Ile
1490                1495                1500

Asp Arg Asp Ala Gly Glu Glu Glu Ala Asp Asp Asn Thr Pro Ala
1505                1510                1515
```

-continued

```
Glu Leu Thr Asn Gly Arg Ser Arg Arg Asn Gly Lys Lys Ser Asp
    1520                1525                1530

Leu Leu Arg Gly Leu Leu Asp Pro Gly Arg Asn Gly Ser Lys Thr
    1535                1540                1545

Arg Ser Gln Pro Glu Glu Ser Asn Thr Ser Ala Ser Lys Glu Thr
    1550                1555                1560

Thr Pro Asp Gln Gly Ser Thr Asn Glu Glu Glu Met Ala Asp Ala
    1565                1570                1575

Pro Asp Asp Gly Ser Ala Thr Ala Glu Asn Ala Asn Asn Glu Arg
    1580                1585                1590

Trp Leu Gln Asn Pro Pro Lys Ala Thr Val Leu Ser Gly Tyr Asn
    1595                1600                1605

Pro Leu Ser Asp Gly Asp Ser Glu Leu Lys Ala Asp Gly Leu Phe
    1610                1615                1620

Pro Arg Pro Trp Tyr Asn Phe Phe Cys Asn Gln Thr Ile Phe Val
    1625                1630                1635

Phe Phe Ser Val Phe Gln Thr Leu Tyr Lys Arg Leu Lys Thr Val
    1640                1645                1650

Lys Glu Ser Arg Glu Ser Val Leu Glu Glu Ile Arg Arg Glu Arg
    1655                1660                1665

Ala Asp Lys Pro Ala Lys Gln Leu Gly Leu Val His Asp Glu Met
    1670                1675                1680

Asn Tyr Phe Asp Gly Asp Pro Glu Thr Phe Trp Pro Arg Thr Val
    1685                1690                1695

Glu Leu Ile Glu Asp Phe Ile Thr Gly Glu Ile Asp Glu Ser Arg
    1700                1705                1710

Cys Gln Asp Val Leu Arg His Tyr Tyr Leu Gln Cys Gly Trp Thr
    1715                1720                1725

Leu Tyr Thr Ile Gln Asp Leu Leu Lys Thr Leu Cys Arg Gln Ala
    1730                1735                1740

Leu Val Cys Asn Asn Ser Asp Asn Lys Glu Lys Thr Pro Asp Leu
    1745                1750                1755

Val Gln Gln Phe Leu Thr Ala Lys Ser Gln Glu Glu Thr Ser Tyr
    1760                1765                1770

Gln Val Glu Ile Ser Ala Arg Lys Phe Ala Glu Lys Cys Ile Lys
    1775                1780                1785

Asp Gly Glu Met Phe Met Ile Thr Trp Ala Pro Ser Ser Asn Glu
    1790                1795                1800

Ala Thr Val Arg Trp Leu Pro Lys Glu Asp Thr Thr Phe His Ala
    1805                1810                1815

Glu Glu Met Glu Pro Thr Asp Arg Trp Lys Tyr Tyr Ile Ala Ser
    1820                1825                1830

Tyr Met Arg Val Asp Pro Thr Glu Gly Val Pro Lys Leu Arg Leu
    1835                1840                1845

Gln Lys Thr Val Leu Ala Arg Asn Leu Pro Ser Ser Asp Ser Asp
    1850                1855                1860

Ser Asp Asp Gly Ala Val Pro Lys Pro Leu Ser Tyr Ser Glu Gly
    1865                1870                1875

Leu Gly Leu Arg Ile Cys Val Asn Ser Ser Lys Ile Val Tyr Glu
    1880                1885                1890

Lys Glu Thr Ser Glu Tyr Thr Ile Tyr Asn Met Thr Ser Leu Ser
    1895                1900                1905

Glu Glu Arg Arg Ala Phe Asp Arg Asp Arg Arg Ala Gln Leu Phe
    1910                1915                1920
```

```
Arg Glu Lys Leu Ile Met Asn Asn Ala Trp Met Lys Asp Leu Ser
    1925                1930                1935

Gln Val Glu Val Gln Gly Met Asn Glu Asp Phe Gln Arg Trp Ala
    1940                1945                1950

Lys Asp Gly Ile Val Pro Gly Thr Ser Ser Thr Gly Gly Ala Gly
    1955                1960                1965

Ser Ser Ala
    1970

<210> SEQ ID NO 63
<211> LENGTH: 453
<212> TYPE: PRT
<213> ORGANISM: Cryptococcus neoformans

<400> SEQUENCE: 63

Met Pro Asp Lys Leu His Leu Pro Ile Asp Asp Val Gln Ile Pro Phe
1               5                   10                  15

Ser Ile Leu Asp Thr Asp Leu Tyr Lys Leu Thr Met Gln Asn Ala Val
            20                  25                  30

Leu His His Phe Ser Asp Ala His Val Val Ile Lys Phe Thr Asn Arg
        35                  40                  45

Ser Pro Gln Met Leu Phe Ser Lys Glu Cys Phe Asp Trp Val Gln Gln
    50                  55                  60

Arg Val Asn Asp Leu Ser Lys Leu Lys Leu Thr Ser Glu Glu Arg Lys
65                  70                  75                  80

Glu Leu Ser Lys Ala Cys Pro Tyr Phe Ser Ser Tyr Leu Asp Tyr
                85                  90                  95

Leu Ser Asn Met Gln Leu Asp Pro Val Lys Gln Val Lys Leu Thr Phe
            100                 105                 110

Ile Pro Gln Gly Ser Asn Glu Lys Gly Glu Lys Met Gly Glu Ile Gly
        115                 120                 125

Cys Val Ile Glu Gly Pro Trp Lys Asp Thr Met Leu Tyr Glu Val Pro
    130                 135                 140

Val Met Ala Ile Leu Ser Glu Gly Tyr Phe Lys Phe Val Asp Thr Asp
145                 150                 155                 160

Trp Asp Tyr Asp Gly Gln Phe Glu Leu Ala Lys Lys Ala Leu Asp
                165                 170                 175

Leu Leu Asn Pro Pro Ala Pro Thr Thr Ser Leu Ser Phe Ser Glu Phe
            180                 185                 190

Gly Thr Arg Arg Arg Arg Ser Phe Lys Ala Gln Asp Ile Ile Met Arg
        195                 200                 205

Gly Leu Ile Ala Gly His Glu Glu Tyr Lys Ser Lys Gly Gly Ser Gln
    210                 215                 220

Gly Ile Leu Ser Gly Thr Ser Asn Val Tyr Leu Ala Leu Lys Tyr Gly
225                 230                 235                 240

Leu Asn Pro Val Gly Thr Ile Ala His Glu Trp Ile Met Ala Val Gly
                245                 250                 255

Ala Thr Tyr Gly Tyr Arg Gly Ala Asn Gly Arg Ala Met Asp Met Trp
            260                 265                 270

Glu Glu Val Tyr Pro Pro Gly Thr Lys Phe Ser Ser Pro Leu Thr Met
        275                 280                 285

Leu Thr Asp Thr Tyr Thr Ala Ala Ile Phe Phe Lys Asp Phe Ile Ser
    290                 295                 300

Asp Pro Ala Arg Ala Leu Arg Trp Ala Val Leu Arg Gln Asp Ser Gly
305                 310                 315                 320
```

```
Asp Ala Phe Lys Phe Val Glu Asp Ala Lys Glu Ala Trp Arg Thr Ile
            325                 330                 335

Glu Asp Lys Ala Gly Ile Lys Arg Asp Val Gly Pro Asn Gly Glu Glu
            340                 345                 350

Glu Val Ala Lys Gly Lys Lys Val Ile Phe Ser Asp Gly Leu Asp Val
            355                 360                 365

Glu Lys Ala Ile Lys Leu Gln Gln Gly Cys Asp Lys Ala Gly Met Ala
        370                 375                 380

Ala Ser Phe Gly Ile Gly Thr Asp Leu Thr Asn Asp Phe Arg Lys Ala
385                 390                 395                 400

Ser Asp Pro Ser Gln Lys Ser Lys Ala Leu Asn Met Val Ile Lys Leu
            405                 410                 415

Asn Lys Ile Asn Gly Lys Asp Cys Ile Lys Leu Ser Asp Asp Lys Gly
            420                 425                 430

Lys His Thr Gly Ser Leu Glu Glu Val Arg Lys Ala Gln Gln Glu Leu
            435                 440                 445

Gly Ile Asp Lys Asn
            450

<210> SEQ ID NO 64
<211> LENGTH: 718
<212> TYPE: PRT
<213> ORGANISM: Cryptococcus neoformans

<400> SEQUENCE: 64

Met Glu Glu Pro Ser Ser Pro Arg Lys Pro Ser Pro Ser Ser Pro Pro
1               5                   10                  15

Ser Ser Ser Ser Ser Pro Ala Gly Ser Leu Asp Leu Pro Ser Leu Gln
            20                  25                  30

Pro Leu Ser His Asp His Pro Leu Leu Thr Ala Pro Thr Phe Asp Pro
            35                  40                  45

Asp Ala Phe Leu Leu Ser Arg Ile His Ile Pro Leu Glu Glu Leu Arg
        50                  55                  60

Gly Glu Leu Arg Glu Tyr Leu Gly Glu Leu Arg Glu Glu Leu Val Lys
65              70                  75                  80

Leu Ile Asn Glu Asp Tyr Glu Glu Phe Leu Ser Leu Gly Ile Gly Leu
            85                  90                  95

Arg Gly Glu Glu Glu Arg Leu Lys Arg Leu Glu Gly Pro Leu Gln Gly
            100                 105                 110

Val Arg Lys Glu Ile Val Ser Val Arg Asp Val Leu Ala Glu His Gln
            115                 120                 125

Ala Lys Leu Gln Glu Lys Leu Asp Glu Arg Ala Ala Leu Arg Glu Glu
        130                 135                 140

Lys Ala Leu Leu Asp Leu Leu Gln Arg Leu Phe Asp Thr Leu Ala Lys
145                 150                 155                 160

Ala Glu Ala Leu Leu Asp Leu Pro His Thr Asp Glu Leu Glu Thr Ser
            165                 170                 175

Lys Leu Val Thr Arg Val Ala Gly Glu Tyr Ser Gln Ile Val Tyr Leu
            180                 185                 190

Met Asn Lys Ala Arg Thr Glu Glu Cys Ala Ile Val Asn Val Val Glu
            195                 200                 205

Glu Arg Ile Lys Asn Ile Lys Ser Arg Leu Ser Lys Asp Leu Ser Thr
        210                 215                 220

Val Leu Leu Ser Glu Leu Glu Asn Leu Asn Ala Thr Gly Leu Lys Gln
225                 230                 235                 240
```

```
Cys Leu Lys Thr Tyr Glu Leu Ile Glu Gly Trp Glu Ala Glu Glu
                245                 250                 255

Val Val Arg Lys Val Phe Arg Glu Tyr Cys Arg Asn Thr Ile Ser Ser
                260                 265                 270

Ser Ala Leu Ser Leu Pro Thr Ser Pro Thr Ala Pro Gln Thr Pro His
                275                 280                 285

Gln Leu Arg Asn Pro Leu Asp Val Pro Arg Leu Pro Ala Ser Tyr Asn
                290                 295                 300

Thr Pro Leu Ala Leu Leu Phe Asn Arg Val Leu Ala Gln Val Ala Ser
305                 310                 315                 320

Tyr Gln Pro Leu Leu Asp Ala Ser Lys Glu Val Ser Glu Lys Phe Asp
                325                 330                 335

Phe Phe Ala Arg Val Phe Trp Pro Glu Ile Gly Asp Thr Ile Ile Glu
                340                 345                 350

Arg Leu Gly Ser Val Ile Phe Ala Ala Gly Arg Pro Asp Asp Leu His
                355                 360                 365

Lys Tyr Tyr Thr Thr Ser His Lys Phe Leu Asp Leu Leu Glu Thr Ile
                370                 375                 380

Ala Pro Ser Ala His Asn Val Leu Ala Met Arg Ser Ser Pro Ser Tyr
385                 390                 395                 400

Thr Ala Phe Glu Arg Arg Trp Gln Leu Pro Val Tyr Phe Gln Leu Arg
                405                 410                 415

Trp Lys Glu Ile Val Ser Ser Leu Glu Gln Ser Leu Ala Gly Gln Pro
                420                 425                 430

Ser Tyr Thr Ser Thr Ser Asp His Lys Gly Ser Lys Trp Val Leu Val
                435                 440                 445

Gln Ser Gly Ala Val Trp Lys Ala Leu Glu Ser Cys Trp Lys Glu Asp
                450                 455                 460

Val Tyr Ile Ser Glu Leu Ala Pro Arg Phe Trp Arg Leu Ser Leu Gln
465                 470                 475                 480

Ile Ser Ser Arg Tyr Gly Thr Tyr Leu Lys Ser Thr Val Asp Ser Tyr
                485                 490                 495

Val Ile Thr Glu Glu Asp Asn Ser Gln Glu Asp Ala Ala Leu Arg Phe
                500                 505                 510

Ala Ser Ala Ala Val Val Asp Leu Glu Asn Leu Ala Ala Lys Val Lys
                515                 520                 525

Asp Leu Asp Val Val Lys Glu Leu Asn Leu Gly Glu His Leu Thr Leu
                530                 535                 540

Pro Thr Thr Gln Tyr Thr Ser Lys Ile Leu Ser Ile Leu Thr Arg Arg
545                 550                 555                 560

Cys Thr Asp Pro Leu Lys Leu Ile Arg Ser Ile Ala Ser Gln Phe Arg
                565                 570                 575

Ser Ser Pro Thr Pro Ser Thr Pro Ser Ser Thr Arg Gln Pro Ser Tyr
                580                 585                 590

Phe Val Pro Ser Val Phe Lys Pro Leu His Ser Leu Leu Ser Ser Gln
                595                 600                 605

Pro Gln Leu Lys Glu Arg Tyr Gln Gln Asp Phe Ser Arg Gln Ile Ala
                610                 615                 620

Asp Ala Val Phe Val Asn Tyr Ala Ser Thr Leu Ala Ser Val Lys Lys
625                 630                 635                 640

Thr Glu Asp Leu Leu Arg Lys His Arg Lys Ser Lys Lys Ser Gly Ile
                645                 650                 655

Thr Ser Phe Phe Gly Gly Gly Gly His Asp Gly Gly Ser Gly Glu Lys
```

```
                660                 665                 670
Glu Glu Glu Arg Phe Thr Asn Gln Met Lys Val Asp Ile Asp Ala Leu
                675                 680                 685
Lys Glu Asp Ala Lys Gly Leu Gly Val Asp Pro Glu Ser Met Asn Ser
            690                 695                 700
Trp Asn Glu Leu Leu Ala Val Val Asn Lys Pro Asp Glu Ala
705                 710                 715

<210> SEQ ID NO 65
<211> LENGTH: 612
<212> TYPE: PRT
<213> ORGANISM: Ustilago maydis

<400> SEQUENCE: 65

Met Cys Ala Ala Pro Ser Thr Ser Ala Pro Val Ala Lys His Ala Ser
1               5                   10                  15
Asp Ala Ser Pro Ile Arg Ser Ile Leu Asp Thr Asp Leu Tyr Lys Leu
            20                  25                  30
Thr Met Gln Gln Ala Val Leu Arg His Tyr Pro His Thr Arg Val Ala
        35                  40                  45
Tyr Lys Phe Thr Asn Arg Ser Ala Ala Thr Met Lys Phe Thr Arg Gln
    50                  55                  60
Ala Met Asp Arg Ile Arg Asn His Ile Asp Asn Leu Val His Leu Ser
65                  70                  75                  80
Leu Ser Ala Gln Glu Arg Ala Trp Leu Glu Arg Ser Cys Pro Tyr Leu
                85                  90                  95
Gly Lys Asp Tyr Leu Asp Tyr Leu Glu Ala Phe Arg Phe Gln Pro Lys
            100                 105                 110
Gln Gln Val Gln Leu Arg Phe Leu Pro Thr Gly Glu Asp Gly Trp Gly
        115                 120                 125
His Leu Asp Leu Asn Val Ser Gly Val Trp Ser Asp Val Ile Phe Tyr
    130                 135                 140
Glu Val Pro Leu Met Ala Ile Val Ser Glu Val Tyr Phe Ser Thr Ile
145                 150                 155                 160
Asp Thr Asp Trp Ser Leu Gln Asp Gln Tyr Gln Gln Ala Phe Asp Lys
                165                 170                 175
Ala Cys Arg Leu Thr Ser Asn Gly Ile Arg Tyr Ser Glu Phe Gly Thr
            180                 185                 190
Arg Arg Arg Arg Ser Tyr Gln Thr His Arg Ile Val Leu Gln Gly Leu
        195                 200                 205
Met Ala Gly Asp Leu Ser Ala Ser Ser Gly Cys Ser Ser Gly Lys Leu
    210                 215                 220
Leu Gly Thr Ser Asn Val His Phe Ala Gln Gln Phe Asp Leu Val Pro
225                 230                 235                 240
Ile Gly Thr Val Ala His Glu Trp Thr Met Ala Ile Ala Ala Leu Gln
                245                 250                 255
Gly Tyr Ala His Ser Asn Leu Lys Ala Leu Gln Leu Trp Asp Ala Val
            260                 265                 270
Tyr Ser Ala Pro Asp Phe Val Ala Asn Ser Ala Thr His Asp Leu Thr
        275                 280                 285
Ile Ala Leu Thr Asp Thr Phe Ser Thr Asn Val Phe Trp Asn Asp Leu
    290                 295                 300
Leu Asp Asn Pro Ser Gly Ile Glu Ile Ala Arg Arg Trp Arg Gly Leu
305                 310                 315                 320
Arg Gln Asp Ser Gly Asp Ser Lys Ala Phe Ala Gln Lys Ala Leu Asp
```

```
                    325                 330                 335
Ala Tyr Arg Ser Ile Gly Val Asp Pro Lys Ser Lys Val Val Ile Tyr
            340                 345                 350

Ser Asp Gly Leu Asp Val Asp Arg Cys Leu Glu Leu Ala Ala Tyr Ser
            355                 360                 365

Asn His Ile Gly Ile Gly Ala Ala Phe Gly Ile Gly Thr Ser Phe Thr
            370                 375                 380

Asn Asp Phe Ile Gln Leu Ser Thr Ala Gln Lys Ser Lys Pro Leu Asn
385                 390                 395                 400

Ile Val Ile Lys Leu Asp Ser Val Glu His Arg Arg Val Val Lys Ile
                405                 410                 415

Ser Asp Asp Leu Thr Lys Asn Thr Gly Asp Pro Thr Glu Val Leu Ala
            420                 425                 430

Val Lys Arg Arg Phe Gly Ile Pro Thr Pro Ser Ser Ala Thr Pro Ala
            435                 440                 445

Asp Ala Ser Val Ile Asn His Leu Asp Pro Gly Ala Pro Pro Asn Pro
            450                 455                 460

Ser Ser His Ala His Leu Gly Thr Asp Asp Ala Thr Met Thr Gln Val
465                 470                 475                 480

Ser Pro Leu Asp Gln Arg Asn Val Ala Ala Gly Val Glu Leu Thr Pro
                485                 490                 495

Pro Asn Glu Pro Arg Arg Leu Leu Ser Ala Arg Ser Thr Ser Lys Leu
            500                 505                 510

Ser Ser Pro Lys Asn Val Ala Ser Ser Cys Ala Trp Ser Asn Cys Ala
            515                 520                 525

Leu Ala Ser Lys Leu Val Ser Ser Ile Pro Ala Ala Leu Ile Ala Gly
            530                 535                 540

Val Ile Glu Arg Ala Arg Glu Gly Asp Cys Asp Cys Glu Pro Asp Ala
545                 550                 555                 560

Pro Arg Glu Met Cys Leu Ala Leu Asn Ala Ala Asn Gly Asp Asp Ala
                565                 570                 575

Gly Ala Thr Ala Pro Ile Ala Gly Leu Asn Ser Glu Ile Gly Val Pro
            580                 585                 590

Gly Val Pro Gly Val Pro Gly Glu Pro Ile Arg Leu Leu Leu Cys Ala
            595                 600                 605

Asn Pro Leu Leu
        610

<210> SEQ ID NO 66
<211> LENGTH: 395
<212> TYPE: PRT
<213> ORGANISM: Saccharomyces cereviseae

<400> SEQUENCE: 66

Met Asp Pro Thr Lys Ala Pro Asp Phe Lys Pro Pro Gln Pro Asn Glu
1               5                   10                  15

Glu Leu Gln Pro Pro Asp Pro Thr His Thr Ile Pro Lys Ser Gly
            20                  25                  30

Pro Ile Val Pro Tyr Val Leu Ala Asp Tyr Asn Ser Ile Asp Ala
            35                  40                  45

Pro Phe Asn Leu Asp Ile Tyr Lys Thr Leu Ser Ser Arg Lys Lys Asn
            50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Ser Glu Glu Glu Ser Glu Gly
```

-continued

```
                    85                  90                  95
Gln Ser Asn Gly Ile Asp Ala Thr Leu Gln Asp Val Thr Met Thr Gly
                100                 105                 110

Asn Leu Gly Val Leu Lys Ser Gln Ile Ala Asp Leu Glu Glu Val Pro
            115                 120                 125

His Thr Ile Val Arg Gln Ala Arg Thr Ile Glu Asp Tyr Glu Phe Pro
            130                 135                 140

Val His Arg Leu Thr Lys Lys Leu Gln Asp Pro Glu Lys Leu Pro Leu
145                 150                 155                 160

Ile Ile Val Ala Cys Gly Ser Phe Ser Pro Ile Thr Tyr Leu His Leu
                165                 170                 175

Arg Met Phe Glu Met Ala Leu Asp Asp Ile Asn Glu Gln Thr Arg Phe
                180                 185                 190

Glu Val Val Gly Gly Tyr Phe Ser Pro Val Ser Asp Asn Tyr Gln Lys
            195                 200                 205

Arg Gly Leu Ala Pro Ala Tyr His Arg Val Arg Met Cys Glu Leu Ala
            210                 215                 220

Cys Glu Arg Thr Ser Ser Trp Leu Met Val Asp Ala Trp Glu Ser Leu
225                 230                 235                 240

Gln Ser Ser Tyr Thr Arg Thr Ala Lys Val Leu Asp His Phe Asn His
                245                 250                 255

Glu Ile Asn Ile Lys Arg Gly Gly Ile Met Thr Val Asp Gly Glu Lys
                260                 265                 270

Met Gly Val Lys Ile Met Leu Leu Ala Gly Gly Asp Leu Ile Glu Ser
            275                 280                 285

Met Gly Glu Pro His Val Trp Ala Asp Ser Asp Leu His His Ile Leu
            290                 295                 300

Gly Asn Tyr Gly Cys Leu Ile Val Glu Arg Thr Gly Ser Asp Val Arg
305                 310                 315                 320

Ser Phe Leu Leu Ser His Asp Ile Met Tyr Glu His Arg Arg Asn Ile
                325                 330                 335

Leu Ile Ile Lys Gln Leu Ile Tyr Asn Asp Ile Ser Ser Thr Lys Val
            340                 345                 350

Arg Leu Phe Ile Arg Arg Gly Met Ser Val Gln Tyr Leu Leu Pro Asn
            355                 360                 365

Ser Val Ile Arg Tyr Ile Gln Glu Tyr Asn Leu Tyr Ile Asn Gln Ser
            370                 375                 380

Glu Pro Val Lys Gln Val Leu Asp Ser Lys Glu
385                 390                 395
```

STRESS RESISTANT PLANTS

CROSS-REFERENCE TO RELATED APPLICATIONS

This application is the U.S. National Stage filing of International Application No. PCT/EP2007/002433, filed Mar. 16, 2007, which claims priority to EP 06075671.5, filed Mar. 21, 2006; U.S. Provisional Patent Application No. 60/784,179, filed Mar. 21, 2006; and EP 06075700.2, filed Mar. 22, 2006, the disclosures of each of which are hereby incorporated by reference.

Methods are provided for increasing the stress resistance in plants and plant cells whereby enzymes involved in the NAD salvage synthesis pathway and/or the NAD de novo synthesis pathway originating from fungal organisms or yeasts, other than *Saccharomyces cereviseae*, are expressed in plants.

BACKGROUND ART

Tolerance of plants to adverse growing conditions, including drought, high light intensities, high temperatures, nutrient limitations, saline growing conditions and the like, is a very desired property for crop plants, in view of the never-ending quest to ultimately increase the actual yield of these plants.

Various ways of achieving that goal of improving what is commonly known as the stress resistance or stress tolerance of plants have been described. Since different abiotic stress conditions frequently result in the generation of harmful reactive oxygen species ("ROS") such as superoxides or hydrogen peroxides, initial attempts to improve stress resistance in plants focused on prevention of the generation of the ROS or the removal thereof. Examples of these approaches are overexpression of ROS scavenging enzymes such as catalases, peroxidases, superoxide dismutases etc. or even increasing the amount of ROS scavenging molecules such as ascorbic acid, glutathione etc. These approaches and other attempts to engineer stress tolerant plants are reviewed e.g. in Wang et al. 2003, Planta 218:1-14.

Stress tolerance in plant cells and plants can also be achieved by reducing the activity or the level of the endogenous poly-ADP-ribose polymerases (ParP) or poly(ADP-ribose) glycohydrolases (ParG) as described in WO00/04173 and PCT/EP2004/003995, respectively. It is thought that in this way, fatal NAD and ATP depletion in plant cells subject to stress conditions, resulting in traumatic cell death, can be avoided or sufficiently postponed for the stressed cells to survive and acclimate to the stress conditions.

Uchimiya et al. (2002) et al. describe the isolation of a rice gene denoted YK1, as well as use of a chimeric YK1 gene to increase the tolerance of transgenic rice plants harboring that gene to rice blast and several abiotic stresses such as NaCl, UV-C, submergence, and hydrogen peroxide. (Uchimiya et al., 2002, Molecular breeding 9: 25-31).

Uchimiya et al. further published a poster abstract describing that overexpression of a NAD dependent reductase gene (YK1) in rice cells also promoted the level of NAD(P)(H) through up-regulating NAD synthetase activities, and concluded that this modification in turn generated a pool of redox substances needed for ROS stress resistance (Uchimiya et al. 2003 Keystone symposium on Plant biology: Functions and control of cell death, Snowbird Utah Apr. 10-15, 2003).

NAD synthetase from yeast has been well characterized and is the last enzyme in both the NAD de novo synthesis pathway and the NAD salvage. In the de novo pathway, quinolate is the precursor for NAD synthesis and is generated as a product of tryptophan degradation. In the salvage pathway, nicotinamide (which is a degradation product of NAD, generated through the action of various enzymes such as PARP, NAD-dependent deacetylases or other NAD glycohydrolases) is the precursor molecule. In a first step, nicotinamide is deamidated to nicotinic acid by a nicotinamidase. The nicotinic acid is transferred to 5-phosphoribosyl-1-pyrophosphate by the enzyme nicotinate phosphoribosyl transferase to yield nicotinic acid mononucleotide. This compound is shared between the de novo and the salvage pathway. Hence, further conversion of this compound by NAD+ pyrophosphorylase and NAD synthetase is achieved as in the de novo pathway.

In yeast, overexpression of PNC1 (encoding nicotinamidase) has been correlated with life span extension by calorie restriction and low-intensity stress (Anderson et al., 2003 Nature 423: p181-185; Gallo et al., 2004, Molecular and Cellular Biology 24: 1301-1312).

WO2004/016726 describes methods and compositions for modulating the life span of eukaryotic and prokaryotic cells and for protecting cells against certain stresses. One method comprises modulating the flux of the NAD+ salvage pathway in the cell, e.g. by modulating the level or activity of one or more proteins selected from the group consisting of PNC1, NMA1, NPT1 and NMA2.

Little is known about the respective enzymes of the NAD biosynthesis pathways in plants. Hunt et al., 2004 describe the use of the available genomic information from Arabidopsis to identify the plant homologues of these enzymes (Hunt et al., 2004, New Phytologist163(1); 31-44). The identified DNA sequences have the following Accession numbers: for nicotinamidase: At5g23220; At5g23230 and At3g16190; for nicotinate phosphoribosyltransferase: At4g36940, At2g23420, for nicotinic acid mononucleotide adenyltransferase: At5g55810 and for NAD synthetase: At1g55090 (all nucleotide sequences are incorporated herein by reference).

PCT/EP 2005/010168 describes methods for increasing the stress resistance in plants and plant cells whereby enzymes involved in the NAD salvage synthesis pathway and/or the NAD de novo synthesis pathway are expressed in plants.

Alternative methods for increasing stress tolerance in plants are still required and the embodiments described hereinafter, including the claims, provide such methods and means.

SUMMARY OF THE INVENTION

In one embodiment of the invention, a method is provided for obtaining a plant with increased stress resistance comprising introducing a chimeric gene into a cells of a plant to obtain transgenic cells whereby the chimeric gene comprises the following operably linked DNA fragments:
   i. A plant-expressible promoter;
   ii. A DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase
   iii. A 3'end region involved in transcription termination and polyadenylation,
followed by regenerating the transgenic cells to obtain a population of transgenic plants; and selecting a plant from the population of transgenic plants which exhibits increased stress resistance or selecting a plant which exhibits a reduced level of reactive oxygen species or maintains a high level of NADH under stress conditions when compared to a similar non-transgenic plant wherein said method is characterized in that the amino acid sequence of the plant-functional enzyme encoded by the DNA region comprises one of the following: the amino acid sequence of accession number XP_444840 (*Candida glabrata*), the amino acid sequence of accession number XP_456073 (*Kluyveromyces lactis*), the amino acid sequence of accession number NP_986013 (*Eremothecium gossypii*), the amino acid sequence of accession number XP_888958 (*Candida albicans*), the amino acid sequence of accession number XP500320 (*Yarrowia lipolytica*), the amino acid sequence of accession number XP389372 (*Giberella zeae*), the amino acid sequence of accession number XP_749509 (*Aspergillus fumigatus*), the amino acid sequence of accession number XP_712112 (*Candida albicans*), the amino acid sequence of accession number BAE56421 (*Aspergillus oryzae*), the amino acid sequence of accession number XP_567125 (*Cryptococcus neofomans*), the amino acid sequence of accession number XP_964547 (*Neurospora crassa*), the amino acid sequence of accession number XP_712135 (*Candida albicans*), the amino acid sequence of accession number XP_448179 (*Candida glabrata*), the amino acid sequence of accession number XP_453643 (*Kluyveromyces lactis*), the amino acid sequence of accession number NP_987024 (*Eremothecium gossypii*), the amino acid sequence of accession number XP_500272 (*Yarrowia lipolytica*), the amino acid sequence of accession number XP_722371 (*Candida albicans*), the amino acid sequence of accession number XP_456405 (*Debaromyces hansenii*), the amino acid sequence of accession number BAE61562 (*Aspergillus oryzae*), the amino acid sequence of accession number XP_759702 (*Ustilago maydis*), the amino acid sequence of accession number EAL18D79 (*Cryptococcus neoformans*), the amino acid sequence of accession number NP_587771 (*Schizosaccharomyces pombe*), the amino acid sequence of accession number XP_681472 (*Aspergillus nidulans*), the amino acid sequence of accession number XP_959191 (*Neurospora crassa*), the amino acid sequence of accession number XP_567726 (*Cryptococcus neoformans*), the amino acid sequence of accession number EAQ90706 (*Chaetomium globosum*), the amino acid sequence of accession number XP_387574 (*Giberella zeae*), the amino acid sequence of accession number XP_748008 (*Aspergillus fumigatus*), the amino acid sequence of accession number XP_361704 (*Magnaporthe grisea*), the amino acid sequence of accession number Q06178, the amino acid sequence of accession number XP_444815 (*Candida glabrata*), the amino acid sequence of accession number NP_986687 ((*Eremothecium gossypii*), the amino acid sequence of accession number XP_453005 (*Kluyveromyces lactis*), the amino acid sequence of accession number XP_458184(*Debaromyces hansenii*), the amino acid sequence of accession number XP_718656 (*Candida albicans*), the amino acid sequence of accession number XP_504391 (*Yarrowia lipolytica*), the amino acid sequence of accession number NP_592856 (*Schizosaccharomyces pombe*), the amino acid sequence of accession number XP_762639 (*Ustilago maydis*), the amino acid sequence of accession number XP_571297 (*Cryptococcus neoformans*), the amino acid sequence of accession number BAE57070 (*Aspergillus oryzae*), the amino acid sequence of accession number XP_750776 (*Aspergillus fumigatus*), the amino acid sequence of accession number XP_659349 (*Aspergillus nidulans*), the amino acid sequence of accession number XP_389652 (*Giberelia zeae*), the amino acid sequence of accession number XP_957634 (*Neurospora crassa*), the amino acid sequence of accession number XP_363364 (*Magnaporthe grisea*), the amino acid sequence of accession number XP_758179 (*Ustilago maydis*), the amino acid sequence of accession number EAQ85219 ((*Chaetomium globosum*), the amino acid sequence of accession number CAA85352 (*Saccharomyces cerevisae*), the amino acid sequence of accession number XP_448893 (*Candida glabrata*), the amino acid sequence of accession number XP_453357 (*Kluyveromyces lactis*), the amino acid sequence of accession number NP_983562 (*Eremothecium gossypii*), the amino acid sequence of accession number XP_462577 (*Debaromyces hansenii*), the amino acid sequence of accession number XP_889008 (*Candida albicans*), the amino acid sequence of accession number XP_500338 (*Yarrowia lipolytica*), the amino acid sequence of accession number XP_746744 (*Aspergillus fumigatus*), the amino acid sequence of accession number BAE64333 (*Aspergillus oryzae*), the amino acid sequence of accession number XP_965789 (*Neurospora crassa*), the amino acid sequence of accession number EAQ93453 (*Chaetomium globosum*), the amino acid sequence of accession number XP_682385 (*Aspergillus nidulans*), the amino acid sequence of accession number AAN74808 (*Gibberella moniliformis*), the amino acid sequence of accession number Q9UTK3, the amino acid sequence of accession number XP_361075 (*Magnaporthe grisea*), the amino acid sequence of accession number EAL18922 (*Cryptococcus neoformans*), the amino acid sequence of accession number XP_568039 (*Cryptococcus neoformans*), the amino acid sequence of accession number XP_760597 (*Ustilago maydis*), the amino acid sequence of accession number NP_011524, the amino acid sequence of accession number XP_444815 (*Candida glabrata*), the amino acid sequence of accession number NP_986687 ((*Eremothecium gossypii*), the amino acid sequence of accession number XP_453005 (*Kluyveromyces lactis*), the amino acid sequence of accession number XP_458184 (*Debaromyces hansenii*), the amino acid sequence of accession number XP_718656 (*Candida albicans*), the amino acid sequence of accession number XP_504391 (*Yarrowia lipolytica*), the amino acid sequence of accession number NP_592856 (*Schizosaccharomyces pombe*), the amino acid sequence of accession number XP_762639 (*Ustilago maydis*), the amino acid sequence of accession number XP_571297 (*Cryptococcus neoformans*), the amino acid sequence of accession number BAE57070 (*Aspergillus oryzae*), the amino acid sequence of accession number XP_750776 (*Aspergillus fumigatus*), the amino acid sequence of accession number XP_659349 (*Aspergillus nidulans*), the amino acid sequence of accession number XP_389652 (*Giberella zeae*), the amino acid sequence of accession number XP_957634 (*Neurospora crassa*), the amino acid sequence of accession number XP_363364 (*Magnaporthe grisea*), the amino acid sequence of accession number XP_758179 (*Ustilago maydis*) or the amino acid sequence of accession number EAQ85219 (*Chaetomium globosum*).

In another embodiment, the invention relates to the chimeric genes as described herein, plant cells comprising these chimeric genes, and plants consisting essentially of plant cells comprising these chimeric genes, and seeds of such plants. These plants and plant cells may be characterized in that they have a lower level of reactive oxygen species under stress conditions than a similar plant not comprising such a chimeric gene.

In yet another embodiment, the invention relates to the use of the described chimeric genes to increase the stress resistance of a plant or to decrease the level of reactive oxygen species in a plant or a plant cell under stress conditions.

The invention further provides the use of one of the mentioned DNA sequence encoding a plant functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase which are from fungal or yeast-like origin to increase the stress resistance of a plant or to decrease the level of reactive oxygen species or maintain the level of NADH in a plant or a plant cell under stress conditions.

DETAILED DESCRIPTION

The current invention is based on the finding that DNA sequences encoding plant-functional enzymes from the NAD salvage pathway in yeasts could be used to obtain transgenic plants which were more resistant to stress, particularly abiotic stress, than plants not comprising these DNA sequences. The transgenic plants also exhibited a significantly reduced level of reactive oxygen species ("ROS") and maintained a high level of NADH, when put under stress conditions, compared to control plants Thus in one embodiment of the invention, a method is provided to obtain a plant with increased stress resistance, whereby the method comprises the steps of
  introducing a stress resistant chimeric gene as herein described into cells of a plant to obtain cells comprising the stress resistant chimeric gene;
  regenerating these cells comprising the stress resistant chimeric gene to obtain a population of plants comprising the stress resistant chimeric gene; and
  selecting a plant from the population of these plants which exhibits increased stress resistance and/or decreased ROS level under stress conditions and/or maintains a high level of NADH, when compared to a similar non-transgenic plant.

The stress resistant chimeric gene thereby comprises a plant-expressible promoter operably linked to a DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase from fungal or yeast like origin and a 3'end region involved in transcription termination and polyadenylation.

As used herein, "a plant-functional enzyme of the nicotinamide adenine dinucleotide salvage synthesis pathway" is an enzyme which when introduced into plants, linked to appropriate control elements such as plant expressible promoter and terminator region, can be transcribed and translated to yield a enzyme of the NAD salvage synthesis pathway functional in plant cells. Included are the enzymes (and encoding genes) from the NAD salvage synthesis, which are obtained from a yeast or fungus different from *Saccharomyces cerevisae*.

The latter proteins are very suitable for the methods according to the invention, since these are less likely to be subject to the enzymatic feedback regulation etc. to which similar plant-derived enzymes may be subject.

Enzymes involved in the NAD salvage synthesis pathway comprise the following
  Nicotinamidase (EC 3.5.1.19) catalyzing the hydrolysis of the amide group of nicotinamide, thereby releasing nicotinate and NH3. The enzyme is also known as nicotinamide deaminase, nicotinamide amidase, YNDase or nicotinamide amidohydrolase
  Nicotinate phophoribosyltransferase (EC 2.4.2.11) also known as niacin ribonucleotidase, nicotinic acid mononucleotide glycohydrolase; nicotinic acid mononucleotide pyrophosphorylase; nicotinic acid phosphoribosyltransferase catalyzing the following reaction

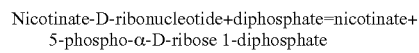

Nicotinate-D-ribonucleotide+diphosphate=nicotinate+ 5-phospho-α-D-ribose 1-diphosphate Nicotinate-nucleotide adenylyltransferase, (EC 2.7.7.18) also known as deamido-NAD+pyrophosphorylase; nicotinate mononucleotide adenylyltransferase; deamindonicotinamide adenine dinucleotide pyrophsophorylase; NaMT-ATase; nicotinic acid mononucleotide adenylyltransferase catalyzing the following reaction

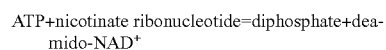

ATP+nicotinate ribonucleotide=diphosphate+deamido-NAD⁺

NAD-synthase (EC 6.3.1.5) also known as NAD synthetase; NAD+synthase; nicotinamide adenine dinucleotide synthetase; diphosphopyridine nucleotide synthetase, catalyzing the following reaction

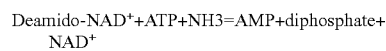

Deamido-NAD⁺+ATP+NH3=AMP+diphosphate+ NAD⁺

In one embodiment of the invention, the coding regions encoding the different enzymes of the NAD salvage pathway comprise a nucleotide sequence encoding proteins with the amino acid sequences as set forth hereinafter.

Suitable nucleotide sequences encoding a nicotinamidase similar to PNC1 from *Saccharomyces cerevisiae* but from fungal or yeast-like origin include a nucleotide sequence encoding a nicotineamidase comprising an amino acid sequence selected from:
  the amino acid sequence of accession number XP_444840 (*Candida glabrata*)
  the amino acid sequence of accession number XP_456073 (*Kluyveromyces lactis*)
  the amino acid sequence of accession number NP_986013 (*Eremothecium gossypii*)
  the amino acid sequence of accession number XP_888958 (*Candida albicans*)
  the amino acid sequence of accession number XP500320 (*Yarrowia lipolytica*)
  the amino acid sequence of accession number XP389372 (*Giberella zeae*)
  the amino acid sequence of accession number XP_749509 (*Aspergillus fumigatus*)
  the amino acid sequence of accession number XP_712112 (*Candida albicans*)
  the amino acid sequence of accession number BAE56421 (*Aspergillus oryzae*)
  the amino acid sequence of accession number XP_567125 (*Cryptococcus neofomans*)
  the amino acid sequence of accession number XP_964547 (*Neurospora crassa*)
  the amino acid sequence of accession number XP_712135 (*Candida albicans*)

Suitable nucleotide sequences encoding an NAD(+) synthetase similar to Qns1 from *Saccharomyces cerevisiae* but from fungal origin include a nucleotide sequence encoding a NAD(+) synthetase comprising an amino acid sequence selected from:
  the amino acid sequence of accession number XP_448179 (*Candida glabrata*)
  the amino acid sequence of accession number XP_453643 (*Kluyveromyces lactis*)
  the amino acid sequence of accession number NP_987024 (*Eremothecium gossypii*)
  the amino acid sequence of accession number XP_500272 (*Yarrowia lipolytica*)

the amino acid sequence of accession number XP_722371 (*Candida albicans*)
the amino acid sequence of accession number XP_456405 (*Debaromyces hansenii*)
the amino acid sequence of accession number BAE61562 (*Aspergillus oryzae*)
the amino acid sequence of accession number XP_759702 (*Ustilago maydis*)
the amino acid sequence of accession number EAL18079 (*Cryptococcus neoformans*)
the amino acid sequence of accession number NP_587771 (*Schizosaccharomyces pombe*)
the amino acid sequence of accession number XP_681472 (*Aspergillus nidulans*)
the amino acid sequence of accession number XP_959191 (*Neurospora crassa*)
the amino acid sequence of accession number XP_567726 (*Cryptococcus neoformans*)
the amino acid sequence of accession number EAQ90706 (*Chaetomium globosum*)
the amino acid sequence of accession number XP_387574 (*Giberella zeae*)
the amino acid sequence of accession number XP_748008 (*Aspergillus fumigatus*)
the amino acid sequence of accession number XP_361704 (*Magnaporthe grisea*)

Suitable nucleotide sequences encoding an Nicotinic acid mononucleotide adenylyltransferase similar to NMA1 from *Saccharomyces cerevisiae* but from fungal origin include a nucleotide sequence encoding a acid mononucleotide adenylyltransferase comprising an amino acid sequence selected from:
the amino acid sequence of accession number Q06178
the amino acid sequence of accession number XP_444815 (*Candida glabrata*)
the amino acid sequence of accession number NP_986687 ((*Eremothecium gossypii*)
the amino acid sequence of accession number XP_453005 (*Kluyveromyces lactis*)
the amino acid sequence of accession number XP_458184 (*Debaromyces hansenii*)
the amino acid sequence of accession number XP_718656 (*Candida albicans*)
the amino acid sequence of accession number XP_504391 (*Yarrowia lipolytica*)
the amino acid sequence of accession number NP_592856 (*Schizosaccharomyces pombe*)
the amino acid sequence of accession number XP_762639 (*Ustilago maydis*)
the amino acid sequence of accession number XP_571297 (*Cryptococcus neoformans*)
the amino acid sequence of accession number BAE57070 (*Aspergillus oryzae*)
the amino acid sequence of accession number XP_750776 (*Aspergillus fumigatus*)
the amino acid sequence of accession number XP_659349 (*Aspergillus nidulans*)
the amino acid sequence of accession number XP_389652 (*Giberella zeae*)
the amino acid sequence of accession number XP_957634 (*Neurospora crassa*)
the amino acid sequence of accession number XP_363364 (*Magnaporthe grisea*)
the amino acid sequence of accession number XP_758179 (*Ustilago maydis*)
the amino acid sequence of accession number EAQ85219 ((*Chaetomium globosum*)

Suitable nucleotide sequences encoding a nicotinate phosphoribosyltransferase similar to NPT1 from *Saccharomyces cerevisiae* but from fungal or yeast-like origin include a nucleotide sequence encoding nicotinate phosphoribosyltransferase comprising an amino acid sequence selected from:
the amino acid sequence of accession number CAA85352 (*Saccharomyces cerevisiae*)
the amino acid sequence of accession number XP_448893 (*Candida glabrata*)
the amino acid sequence of accession number XP-453357 (*Kluyveromyces lactis*)
the amino acid sequence of accession number NP_983562 (*Eremothecium gossypii*)
the amino acid sequence of accession number XP_462577 (*Debaromyces hansenii*)
the amino acid sequence of accession number XP_889008 (*Candida albicans*)
the amino acid sequence of accession number XP_500338 (*Yarrowia lipolytica*)
the amino acid sequence of accession number XP_746744 (*Aspergillus fumigatus*)
the amino acid sequence of accession number BAE64333 (*Aspergillus oryzae*)
the amino acid sequence of accession number XP_965789 (*Neurospora crassa*)
the amino acid sequence of accession number EAQ93453 (*Chaetomium globosum*)
the amino acid sequence of accession number XP_682385 (*Aspergillus nidulans*)
the amino acid sequence of accession number AAN74808 (*Gibberella moniliformis*)
the amino acid sequence of accession number Q9UTK3
the amino acid sequence of accession number XP_361075 (*Magnaporthe grisea*)
the amino acid sequence of accession number EAL18922 (*Cryptococcus neoformans*)
the amino acid sequence of accession number XP_568039 (*Cryptococcus neoformans*)
the amino acid sequence of accession number XP_760597 (*Ustilago maydis*)

Suitable nucleotide sequences encoding an Nicotinic acid mononucleotide adenylyltransferase similar to NMA2 from *Saccharomyces cerevisiae* but from fungal or yeast like origin include a nucleotide sequence encoding a acid mononucleotide adenylyltransferase comprising an amino acid sequence selected from:
the amino acid sequence of accession number NP_011524
the amino acid sequence of accession number XP_444815 (*Candida glabrata*)
the amino acid sequence of accession number NP_986687 ((*Eremothecium gossypii*)
the amino acid sequence of accession number XP_453005 (*Kluyveromyces lactis*)
the amino acid sequence of accession number XP_458184 (*Debaromyces hansenii*)
the amino acid sequence of accession number XP_718656 (*Candida albicans*)
the amino acid sequence of accession number XP_504391 (*Yarrowia lipolytica*)
the amino acid sequence of accession number NP_592856 (*Schizosaccharomyces pombe*)
the amino acid sequence of accession number XP_762639 (*Ustilago maydis*)
the amino acid sequence of accession number XP_571297 (*Cryptococcus neoformans*)

the amino acid sequence of accession number BAE57070 (*Aspergillus oryzae*)

the amino acid sequence of accession number XP_750776 (*Aspergillus fumigatus*)

the amino acid sequence of accession number XP_659349 (*Aspergillus nidulans*)

the amino acid sequence of accession number XP_389652 (*Giberella zeae*)

the amino acid sequence of accession number XP_957634 (*Neurospora crassa*)

the amino acid sequence of accession number XP_363364 (*Magnaporthe grisea*)

the amino acid sequence of accession number XP_758179 (*Ustilago maydis*)

the amino acid sequence of accession number EAQ85219 ((*Chaetomium globosum*)

All amino acid sequences referred to by their accession numbers are herein incorporated by reference.

However, it will be clear that variants of these sequences, including insertions, deletions and substitutions thereof may be also be used to the same effect. Variants of the described sequence will have a sequence identity which is preferably at least about 80%, or 85 or 90% or 95% with identified sequences of enzymes from the NAD salvage pathway. Preferably, these variants will be functional proteins with the same enzymatic activity as the enzymes from the NAD salvage pathway. For the purpose of this invention, the "sequence identity" of two related nucleotide or amino acid sequences, expressed as a percentage, refers to the number of positions in the two optimally aligned sequences which have identical residues. (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Homologous nucleotide sequence from other fungi or yeast-like organisms may also be identified and isolated by hybridization under stringent conditions using as probes identified nucleotide sequences encoding enzymes from the NAD salvage pathway.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et al, Molecular Cloning: A Laboratory Manual, Second Edition, Cold Spring Harbor, N.Y. (1989), particularly chapter 11.

The methods of the invention can be used to obtain plants tolerant to different kinds of stress-inducing conditions, particularly abiotic stress conditions including submergence, high light conditions, high UV radiation levels, increased hydrogen peroxide levels, drought conditions, high or low temperatures, increased salinity conditions. The methods of the invention can also be used to reduce the level of ROS in the cells of plants growing under adverse conditions, particularly abiotic stress conditions including submergence, high light conditions, high UV radiation levels, increased hydrogen peroxide levels, drought conditions, high or low temperatures, increased salinity conditions etc. The level of ROS or the level of NADH can be determined using the methods known in the art, including those described in Example 3.

Using the methods described herein, plants may be obtained wherein the level of ROS is equal to or lower than in control plants under non-stressed conditions, such as but not limited to low light. In these plants, under non-stressed conditions, the level of ROS may range from 50% to 100% of the level of control plants under low light conditions, more particularly from about 60% to about 85%. The level of the ROS in these plants under stress conditions is about 50% to 80% of the level of ROS in control plants under stress conditions, corresponding to about 60 to 80% of the level of ROS in control plants under non-stressed conditions. Similarly, the NADH level in these plants is equal to or higher than in control plants under non-stressed conditions, such as but not limited to low light. In these plants, under non-stressed conditions, the level of NADH may range from 100% to 160% of the level of NADH in control plants under low light conditions, more particularly from about 120% to about 140%. The level of NADH in these plants under stress conditions is about 200 to 300% of the level of NADH in control plants under stress conditions, corresponding to about 100 to 160% of the level of ROS in control plants under non-stressed conditions.

Methods to obtain transgenic plants are not deemed critical for the current invention and any transformation method and regeneration suitable for a particular plant species can be used. Such methods are well known in the art and include Agrobacterium-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

It will be clear that the different stress resistant chimeric genes described herein, with DNA regions encoding different enzymes from the NAD salvage pathway can be combined within one plant cell or plant, to further enhance the stress tolerance of the plants comprising the chimeric genes. Thus, in one embodiment of the invention, plant cells and plants are provided which comprise at least two stress resistant chimeric genes each comprising a different coding region.

The transgenic plant cells and plant lines according to the invention may further comprise chimeric genes which will reduce the expression of endogenous PARP and/or PARG genes as described in WO 00/04173 and PCT/EP2004/003995 These further chimeric genes may be introduced e.g. by crossing the transgenic plant lines of the current invention with transgenic plants containing PARP and/or PARG gene expression reducing chimeric genes. Transgenic plant cells or plant lines may also be obtained by introducing or transforming the chimeric genes of the invention into transgenic plant cells comprising the PARP or PARG gene expression reducing chimeric genes or vice versa.

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al., 1988 *Mol. Gen. Genet.* 212, 182-190), the subterranean clover virus promoter No 4 or No 7 (WO9606932), or T-DNA gene promoters but also tissue-specific or organ-specific promoters including but not limited to seed-specific promoters (e.g., WO089/03887), organ-primordia specific promoters (An et al., 1996, *The Plant Cell* 8, 15-30), stem-specific promoters (Keller et al., 1988, *EMBO J.* 7, 3625-3633), leaf specific promoters (Hudspeth et al., 1989, *Plant Mol Biol* 12, 579-589), mesophyl-specific promoters (such as the light-inducible Rubisco promoters), root-specific promoters (Keller et al., 1989, *Genes Devel.* 3, 1639-1646), tuber-specific promoters (Keil et al., 1989, *EMBO J.* 8, 1323-1330), vascular tissue specific promoters (Peleman et al., 1989, *Gene* 84, 359-369), stamen-selective promoters (WO 89/10396, WO 92/13956), dehiscence zone specific promoters (WO 97/13865) and the like.

The chimeric genes of the inventions may also be equipped with a nuclear localization signal ("NLS") functional in plants, operably linked to the DNA region encoding an enzyme of the NAD salvage pathway such as the SV40 NLS.

Having read this document, a person skilled in the art will immediately realize that similar effects with regard to increased stress resistance can be obtained whenever natural variants of plants are obtained wherein the endogenous genes coding for NAD salvage pathway enzymes are more active or expressed at a higher level. Such variant plants can be obtained by subjecting a population of plants to mutagenesis, such as, but not limited to EMS mutagenesis, followed by a screening for an increased activity of any one of the NAD salvage pathway enzymes, or a combination thereof.

It will also be immediately clear that a population of different varieties or cultivars can be screened for increased tolerance to the above mentioned stress conditions in general or particular selected abiotic stresses, followed by a correlation of the increased tolerance to stress conditions with the presence of a particular allele of any of the endogenous genes encoding an enzyme of the NAD salvage pathway enzyme. Such alleles can than be introduced into a plant of interest by crossing, if the species are sexually compatible, or they may be identified using conventional techniques as described herein (including hybridization or PCR amplification) and introduced using recombinant DNA technology. Introduction of particularly desired alleles using breeding techniques may be followed using molecular markers specific for the alleles of interest.

The methods and means described herein are believed to be suitable for all plant cells and plants, both dicotyledonous and monocotyledonous plant cells and plants including but not limited to cotton, Brassica vegetables, oilseed rape, wheat, corn or maize, barley, sunflowers, rice, oats, sugarcane, soybean, vegetables (including chicory, lettuce, tomato), tobacco, potato, sugarbeet, papaya, pineapple, mango, *Arabidopsis thaliana*, but also plants used in horticulture, floriculture or forestry.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The following non-limiting Examples describe the construction of chimeric genes to increase stress resistance in plant cells and plants and the use of such genes.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the specification reference is made to the following entries in the Sequence listing:

SEQ ID No. 1: XP_444840 (*Candida glabrata*)
SEQ ID No. 2: XP_456073 (*Kluyveromyces lactis*)
SEQ ID No. 3: NP_986013 (*Eremothecium gossypii*)
SEQ ID No. 4: XP_888958 (*Candida albicans*)
SEQ ID No. 5: XP500320 (*Yarrowia lipolytica*)
SEQ ID No. 6: XP389372 (*Giberella zeae*)
SEQ ID No. 7: XP_749509 (*Aspergillus fumigatus*)
SEQ ID No. 8: XP_712112 (*Candida albicans*)
SEQ ID No. 9: BAE56421 (*Aspergillus oryzae*)
SEQ ID No. 10: XP_567125 (*Cryptococcus neofomans*)
SEQ ID No. 11 XP_964547 (*Neurospora crassa*)
SEQ ID No. 12: XP_712135 (*Candida albicans*)
SEQ ID No. 13: XP_448179 (*Candida glabrata*)
SEQ ID No. 14: XP_453643 (*Kluyveromyces lactis*)
SEQ ID No. 15: NP_987024 (*Eremothecium gossypii*)
SEQ ID No. 16: XP_500272 (*Yarrowia lipolytica*)
SEQ ID No. 17: XP_722371 (*Candida albicans*)
SEQ ID No. 18: XP_456405 (*Debaromyces hansenii*)
SEQ ID No. 19: BAE61562 (*Aspergillus oryzae*)
SEQ ID No. 20: XP_759702 (*Ustilago maydis*)
SEQ ID No. 21: EAL18079 (*Cryptococcus neoformans*)
SEQ ID No. 22: NP_587771 (*Schizosaccharomyces pombe*)
SEQ ID No. 23: XP_681472 (*Aspergillus nidulans*)
SEQ ID No. 24: XP_959191 (*Neurospora crassa*)
SEQ ID No. 25: XP_567726 (*Cryptococcus neoformans*)
SEQ ID No. 26: EAQ90706 (*Chaetomium globosum*)
SEQ ID No. 27: XP_387574 (*Giberella zeae*)
SEQ ID No. 28: XP_748008 (*Aspergillus fumigatus*)
SEQ ID No. 29: XP_361704 (*Magnaporthe grisea*)
SEQ ID No. 30: Q06178
SEQ ID No. 31: XP_444815 (*Candida glabrata*)
SEQ ID No. 32: NP_986687 ((*Eremothecium gossypii*)
SEQ ID No. 33: XP_453005 (*Kluyveromyces lactis*)

SEQ ID No. 34. XP_458184 (*Debaromyces hansenii*)
SEQ ID No. 35: XP_718656 (*Candida albicans*)
SEQ ID No. 36: XP_504391 (*Yarrowia lipolytica*)
SEQ ID No. 37: NP_592856 (*Schizosaccharomyces pombe*)
SEQ ID No. 38: XP_762639 (*Ustilago maydis*)
SEQ ID No. 39: XP_571297 (*Cryptococcus neoformans*)
SEQ ID No. 40: BAE57070 (*Aspergillus oryzae*)
SEQ ID No. 41: XP_750776 (*Aspergillus fumigatus*)
SEQ ID No. 42: XP_659349 (*Aspergillus nidulans*)
SEQ ID No. 43: XP_389652 (*Giberella zeae*)
SEQ ID No. 44: XP_957634 (*Neurospora crassa*)
SEQ ID No. 45: XP_363364 (*Magnaporthe grisea*)
SEQ ID No. 46: XP_758179 (*Ustilago maydis*)
SEQ ID No. 47: EAQ85219 ((*Chaetomium globosum*)
SEQ ID No. 48: CAA85352 (*Saccharomyces cerevisae*)
SEQ ID No. 49: XP_448893 (*Candida glabrata*)
SEQ ID No. 50: XP_453357 (*Kluyveromyces lactis*)
SEQ ID No. 51: NP_983562 (*Eremothecium gossypii*)
SEQ ID No. 52: XP_462577 (*Debaromyces hansenii*)
SEQ ID No. 53: XP_889008 (*Candida albicans*)
SEQ ID No. 54: XP_500338 (*Yarrowia lipolytica*)
SEQ ID No. 55: XP_746744 (*Aspergillus fumigatus*)
SEQ ID No. 56: BAE64333 (*Aspergillus oryzae*)
SEQ ID No. 57: XP_965789 (*Neurospora crassa*)
SEQ ID No. 58: EAQ93453 (*Chaetomium globosum*)
SEQ ID No. 59: XP_682385 (*Aspergillus nidulans*)
SEQ ID No. 60: AAN74808 (*Gibberella moniliformis*)
SEQ ID No. 61: Q9UTK3
SEQ ID No. 62: XP_361075 (*Magnaporthe grisea*)
SEQ ID No. 63: EAL18922 (*Cryptococcus neoformans*)
SEQ ID No. 64: XP_568039 (*Cryptococcus neoformans*)
SEQ ID No. 65: XP_760597 (*Ustilago maydis*)
SEQ ID No. 66: NP_011524

All amino acid sequences referred to by their accession numbers are herein incorporated by reference.

EXAMPLES

Example 1

Assembly of Stress Resistant Chimeric Genes and Introduction into Plants

To increase the stress resistance in plants, a chimeric gene is constructed using conventional techniques comprising the following DNA fragments in order:

- A promoter region from Cauliflower Mosaic Virus (CaMV 35S);
- A DNA fragment of about 60 bp corresponding to the untranslated leader Cab22L;
- A DNA fragment as mentioned herein elsewhere encoding a NAD salvage pathway enzyme from fungal or yeast-like origin, different from PNC1, NMA1, NMA2 or NPT1 from *Saccharomyces cereviseae*.
- A fragment of the 3' untranslated end from the 35 S transcript of CaMV (3' 35S)

This chimeric gene is introduced in a T-DNA vector, between the left and right border sequences from the T-DNA, together with a selectable marker gene.

The T-DNA vectors are introduced into Agrobacterium strains comprising a helper Ti-plasmid using conventional methods. The chimeric genes are introduced into plants using a conventional transformation method. Transgenic plants exhibit a higher stress resistance than their counterpart plants without transgenes.

The invention claimed is:

1. A method for obtaining a plant with increased stress resistance, said method comprising
   a. introducing a chimeric gene into a cell of a plant to obtain a transgenic cell, said chimeric gene comprising the following operably linked DNA fragments:
      i. a plant-expressible promoter;
      ii. a DNA region coding for a plant-functional nicotinamidase enzyme having at least 95% identity to SEQ ID NO: 1;
      iii. a 3' end region involved in transcription termination and polyadenylation;
   b. regenerating said transgenic cell to obtain a transgenic plant;
   c. making a population of transgenic plants comprising the chimeric gene; and
   d. selecting a plant from said population of transgenic plants which exhibits increased oxidative stress resistance or a reduced level of reactive oxygen species, or that maintains a high level of NADH under stress conditions when compared to a similar non-transgenic plant.

2. A chimeric gene comprising the following operably linked DNA fragments:
   i. a plant-expressible promoter;
   ii. a DNA region coding for a plant-functional nicotinamidase enzyme having at least 95% identity to SEQ ID NO: 1; and
   iii. a 3' end region involved in transcription termination and polyadenylation.

3. A transgenic plant cell comprising the chimeric gene of claim 2, wherein said transgenic plant cell expresses the plant-functional nicotinamidase enzyme having at least 95% identity to SEQ ID NO: 1.

4. A transgenic plant comprising the plant cell of claim 3, wherein said transgenic plant expresses the plant-functional nicotinamidase enzyme having at least 95% identity to SEQ ID NO: 1.

5. The transgenic plant of claim 4, wherein said plant has a lower level of reactive oxygen species under stress conditions than a similar plant not comprising the chimeric gene.

6. A seed comprising a chimeric gene comprising the following operably linked DNA fragments:
   i. a plant-expressible promoter;
   ii. a DNA region coding for a plant-functional nicotinamidase enzyme having at least 95% identity to SEQ ID NO: 1; and
   iii. a 3' end region involved in transcription termination and polyadenylation.

7. A method to decrease the level of reactive oxygen species in a plant or a plant cell under stress conditions or to maintain the level of NAD in a plant or plant cell under stress conditions, said method comprising the step of transforming said plant or plant cell with the chimeric gene of claim 2, wherein the transformation leads to the expression of a plant functional nicotinamidase enzyme having at least 95% identity to SEQ ID NO: 1.

* * * * *